(12) United States Patent
Punnonen et al.

(10) Patent No.: US 7,390,619 B1
(45) Date of Patent: Jun. 24, 2008

(54) OPTIMIZATION OF IMMUNOMODULATORY PROPERTIES OF GENETIC VACCINES

(75) Inventors: Juha Punnonen, Belmont, CA (US); Willem P. C. Stemmer, Los Gatos, CA (US); Robert Gerald Whalen, Foster City, CA (US); Russell J. Howard, Los Altos Hills, CA (US)

(73) Assignee: Maxygen, Inc., Redwood City, CA (US)

( * ) Notice: Subject to any disclaimer, the term of this patent is extended or adjusted under 35 U.S.C. 154(b) by 1282 days.

(21) Appl. No.: 09/724,869

(22) Filed: Nov. 28, 2000

Related U.S. Application Data

(63) Continuation of application No. 09/248,716, filed on Feb. 10, 1999.

(60) Provisional application No. 60/074,294, filed on Feb. 11, 1998.

(51) Int. Cl.
  *C12Q 1/68* (2006.01)
  *G01N 33/574* (2006.01)
(52) U.S. Cl. ............... 435/6; 435/7.1; 435/5; 435/4; 435/DIG. 3; 435/DIG. 2; 536/23.1
(58) Field of Classification Search ................. 435/6, 435/7.1, 4, DIG. 2; 536/23.4, 23.1, 23.53
  See application file for complete search history.

(56) References Cited

U.S. PATENT DOCUMENTS

| | | | |
|---|---|---|---|
| 5,252,714 A | 10/1993 | Harris et al. |
| 5,264,563 A | 11/1993 | Huse |
| 5,338,665 A | 8/1994 | Schatz et al. |
| 5,348,867 A | 9/1994 | Georgiou et al. |
| 5,470,725 A | 11/1995 | Borriss et al. |
| 5,512,463 A | 4/1996 | Stemmer |
| 5,514,588 A | 5/1996 | Varadaraj et al. |
| 5,523,388 A | 6/1996 | Huse |
| 5,571,698 A | 11/1996 | Ladner et al. |
| 5,589,466 A | 12/1996 | Felgner et al. |
| 5,593,972 A | 1/1997 | Weiner et al. |
| 5,605,793 A | 2/1997 | Stemmer et al. |
| 5,691,170 A | 11/1997 | Gritz et al. |
| 5,698,426 A | 12/1997 | Huse |
| 5,703,057 A | 12/1997 | Johnston et al. |
| 5,718,883 A | 2/1998 | Harlan et al. |
| 5,723,323 A | 3/1998 | Kauffman et al. |
| 5,738,852 A | 4/1998 | Robinson et al. |
| 5,763,192 A | 6/1998 | Kauffman et al. |
| 5,763,239 A | 6/1998 | Short et al. |
| 5,770,434 A | 6/1998 | Huse |
| 5,783,386 A | 7/1998 | Jacobs, Jr. et al. |
| 5,789,228 A | 8/1998 | Lam et al. |
| 5,808,022 A | 9/1998 | Huse |
| 5,811,238 A * | 9/1998 | Stemmer et al. ............... 435/6 |
| 5,814,473 A | 9/1998 | Warren et al. |
| 5,814,476 A | 9/1998 | Kauffman et al. |
| 5,817,483 A | 10/1998 | Kauffman et al. |
| 5,824,469 A | 10/1998 | Horwitz et al. |
| 5,824,514 A | 10/1998 | Kauffman et al. |
| 5,830,696 A | 11/1998 | Short |
| 5,830,721 A | 11/1998 | Stemmer et al. |
| 5,834,252 A | 11/1998 | Stemmer et al. |
| 5,837,458 A | 11/1998 | Minshull et al. |
| 5,858,776 A | 1/1999 | Ostrand-Rosenberg et al. |
| 5,861,310 A | 1/1999 | Freeman et al. |
| 5,866,344 A | 2/1999 | Georgiou |
| 5,866,363 A | 2/1999 | Pieczenik |
| 5,871,974 A | 2/1999 | Huse |
| 5,876,997 A | 3/1999 | Kretz |
| 5,882,883 A | 3/1999 | Egel-Mitani et al. |
| 5,925,749 A | 7/1999 | Mathur et al. |
| 5,928,905 A | 7/1999 | Stemmer et al. |
| 5,939,250 A | 8/1999 | Short |
| 5,939,300 A | 8/1999 | Robertson et al. |
| 5,942,430 A | 8/1999 | Robertson et al. |
| 5,948,666 A | 9/1999 | Callen et al. |
| 5,955,358 A | 9/1999 | Huse |
| 5,958,672 A | 9/1999 | Short |
| 5,958,751 A | 9/1999 | Murphy et al. |
| 5,962,258 A | 10/1999 | Mathur et al. |
| 5,962,283 A | 10/1999 | Warren et al. |
| 5,965,408 A | 10/1999 | Short |
| 5,976,862 A | 11/1999 | Kauffman et al. |

(Continued)

FOREIGN PATENT DOCUMENTS

EP   0 125 228 A1   6/1988

(Continued)

OTHER PUBLICATIONS

Torigoe et al , Peptide Chemistry, (1996), vol. date 1995, 33rd, 405-408.*

(Continued)

*Primary Examiner*—T. D. Wessendorf
(74) *Attorney, Agent, or Firm*—Margaret A. Powers; Norman J. Kruse

(57) ABSTRACT

This invention provides methods for obtaining molecules that can modulate an immune response, and immunomodulatory molecules obtained using the methods. The molecules find use, for example, in the tailoring of an immune response induced by a genetic vaccine for a desired purpose.

4 Claims, 22 Drawing Sheets

U.S. PATENT DOCUMENTS

| | | | |
|---|---|---|---|
| 5,985,285 A | 11/1999 | Titball et al. | |
| 5,985,646 A | 11/1999 | Murphy et al. | |
| 5,989,553 A | 11/1999 | Johnston et al. | |
| 6,001,574 A | 12/1999 | Short et al. | |
| 6,004,788 A | 12/1999 | Short | |
| 6,030,779 A | 2/2000 | Short | |
| 6,043,030 A | 3/2000 | Beach et al. | |
| 6,054,267 A | 4/2000 | Short | |
| 6,054,312 A | 4/2000 | Larocca et al. | |
| 6,057,103 A | 5/2000 | Short | |
| 6,071,716 A | 6/2000 | Freeman et al. | |
| 6,084,067 A | 7/2000 | Freeman et al. | |
| 6,087,341 A | 7/2000 | Khavari et al. | |
| 6,096,548 A | 8/2000 | Stemmer | |
| 6,117,679 A | 9/2000 | Stemmer | |
| 6,132,970 A | 10/2000 | Stemmer | |
| 6,149,905 A | 11/2000 | Ostrand-Rosenberg et al. | |
| 6,153,410 A | 11/2000 | Arnold et al. | |
| 6,156,511 A | 12/2000 | Schatz et al. | |
| 6,159,687 A | 12/2000 | Vind | |
| 6,159,688 A | 12/2000 | Borchert et al. | |
| 6,165,718 A | 12/2000 | Borchert et al. | |
| 6,165,793 A | 12/2000 | Stemmer | |
| 6,168,919 B1 | 1/2001 | Short | |
| 6,171,820 B1 | 1/2001 | Short et al. | |
| 6,174,673 B1 | 1/2001 | Short et al. | |
| 6,177,263 B1 | 1/2001 | Arnold et al. | |
| 6,180,406 B1 | 1/2001 | Stemmer et al. | |
| 6,194,183 B1 | 2/2001 | Markvardsen et al. | |
| 6,238,884 B1 | 5/2001 | Short et al. | |
| 6,251,674 B1 | 6/2001 | Tobin et al. | |
| 6,261,561 B1 | 7/2001 | Stewart, Jr. et al. | |
| 6,287,861 B1 | 9/2001 | Stemmer et al. | |
| 6,368,861 B1 | 4/2002 | Crameri et al. | |
| 6,376,246 B1 | 4/2002 | Crameri et al. | |
| 6,406,855 B1 | 6/2002 | Patten et al. | |
| 6,429,286 B1 * | 8/2002 | Sugimura | 530/326 |
| 6,613,514 B2 | 9/2003 | Patten et al. | |
| 2002/0182727 A1 * | 12/2002 | Freeman et al. | 435/325 |

FOREIGN PATENT DOCUMENTS

| | | |
|---|---|---|
| EP | 0 752008 B2 | 2/1995 |
| EP | 0 725081 A1 | 8/1996 |
| EP | 0554809 B1 | 12/1998 |
| EP | 0563296 B1 | 3/1999 |
| EP | 0911396 A2 | 4/1999 |
| EP | 0911396 A3 | 5/1999 |
| EP | 0934999 A1 | 8/1999 |
| EP | 0876509 B1 | 9/2001 |
| WO | WO 90/14424 | 11/1990 |
| WO | WO 90/14443 | 11/1990 |
| WO | WO 91/07979 | 6/1991 |
| WO | WO 91/19818 A1 | 12/1991 |
| WO | WO 92/01047 A1 | 1/1992 |
| WO | WO 92/03461 | 3/1992 |
| WO | WO 92/06176 | 4/1992 |
| WO | WO 92/06204 | 4/1992 |
| WO | WO 92/11272 | 7/1992 |
| WO | WO 92/18619 A1 | 10/1992 |
| WO | WO 93/06214 | 4/1993 |
| WO | WO 93/10214 | 5/1993 |
| WO | WO 94/01567 A1 | 1/1994 |
| WO | WO 94/06421 | 3/1994 |
| WO | WO 94/06911 | 3/1994 |
| WO | WO 94/11496 | 5/1994 |
| WO | WO 94/18330 A1 | 8/1994 |
| WO | WO 94/23738 A1 | 10/1994 |
| WO | WO 94/24267 | 10/1994 |
| WO | WO 94/26787 A1 | 11/1994 |
| WO | WO 94/254608 | 11/1994 |
| WO | WO 95/16027 A1 | 6/1995 |
| WO | WO 95/22625 | 8/1995 |
| WO | WO 95/23859 | 9/1995 |
| WO | WO 95/26718 | 10/1995 |
| WO | WO 96/11279 A1 | 4/1996 |
| WO | WO 96/13250 A1 | 5/1996 |
| WO | WO 96/23882 | 8/1996 |
| WO | WO 96/31613 | 10/1996 |
| WO | WO 96/33207 | 10/1996 |
| WO | WO 96/37624 | 11/1996 |
| WO | WO 97/04077 | 2/1997 |
| WO | WO 97/07128 A1 | 2/1997 |
| WO | WO 97/07205 | 2/1997 |
| WO | WO 97/11605 A1 | 4/1997 |
| WO | WO 97/20078 | 6/1997 |
| WO | WO 97/25410 | 7/1997 |
| WO | WO 97/32987 A1 | 9/1997 |
| WO | WO 97/35957 A1 | 10/1997 |
| WO | WO 97/35966 | 10/1997 |
| WO | WO 97/44361 | 11/1997 |
| WO | WO 97/48416 | 12/1997 |
| WO | WO 97/48717 | 12/1997 |
| WO | WO 97/48794 | 12/1997 |
| WO | WO 98/00526 | 1/1998 |
| WO | WO 98/01581 | 1/1998 |
| WO | WO 98/05764 | 2/1998 |
| WO | WO 98/05765 | 2/1998 |
| WO | WO 98/13485 | 4/1998 |
| WO | WO 98/13487 | 4/1998 |
| WO | WO 98/24799 | 6/1998 |
| WO | WO 98/27230 | 6/1998 |
| WO | WO 98/28416 | 7/1998 |
| WO | WO 98/31816 | 7/1998 |
| WO | WO 98/31837 | 7/1998 |
| WO | WO 98/36080 | 8/1998 |
| WO | WO 98/41622 | 9/1998 |
| WO | WO 98/41623 | 9/1998 |
| WO | WO 98/41653 | 9/1998 |
| WO | WO 98/42727 | 10/1998 |
| WO | WO 98/42832 | 10/1998 |
| WO | WO 98/45444 | 10/1998 |
| WO | WO 98/48034 | 10/1998 |
| WO | WO 98/49286 | 11/1998 |
| WO | WO 98/58085 | 12/1998 |
| WO | WO 99/07837 | 2/1999 |
| WO | WO 99/08539 | 2/1999 |
| WO | WO 99/10472 | 3/1999 |
| WO | WO 99/10539 | 3/1999 |
| WO | WO 99/19506 | 4/1999 |
| WO | WO 99/19518 | 4/1999 |
| WO | WO 99/21979 | 5/1999 |
| WO | WO 99/23107 | 5/1999 |
| WO | WO 99/23236 | 5/1999 |
| WO | WO 99/29902 | 6/1999 |
| WO | WO 99/41366 | 8/1999 |
| WO | WO 99/41368 | 8/1999 |
| WO | WO 99/41369 | 8/1999 |
| WO | WO 99/41383 | 8/1999 |
| WO | WO 99/41402 | 8/1999 |
| WO | WO 99/45154 | 9/1999 |
| WO | WO 99/57128 | 11/1999 |
| WO | WO 99/65927 | 12/1999 |
| WO | WO 00/16984 | 3/2000 |
| WO | WO 00/18778 | 4/2000 |
| WO | WO 00/42560 | 7/2000 |
| WO | WO 00/42561 | 7/2000 |
| WO | WO 00/46344 | 8/2000 |
| WO | WO 00/53744 | 9/2000 |
| WO | WO 00/58517 | 10/2000 |

WO 01/00234 1/2001

OTHER PUBLICATIONS

Fargeas, C.A., et al., "Identification of Residues in the V Domain of CD80 (B7-1) Implicated in Functional Interactions with CD28 and CTLA-4," Journal of Experimental Medicine 182(3):667-675 (1995).

Freeman, G.J. et al., "Cloning of B7-2: A CTLA-4 Counter-Receptor That Costimulates Human T Cell Proliferation," Science 262:909-911 (1993).

Guo, Y., et al., "Mutational Analysis and an Alternatively Spliced Product of B7 Defines Its CD28/CTLA-4 binding Site on Immunoglobulin C-like Comain," Journal of Experimental Medicine 181(4):1345-1355 (1995).

He, X-S. et al., "Costimulatory protein B7-1, enhances the cytotoxic T cell response and antibody response to hepatitis B surface antigen," Proc. Natl. Acad. Sci. USA 93:7274-7278 (1996).

Kim, J.J. et al., "Engineering DNA Vaccines via Co-delivery of Co-Stimulatory Molecule Genes," Vaccine 16(19):1828-1835 (1998).

Kuchroo, V.K. et al., "B7-1 and B7-2 Costimulatory Molecules Activate Differentially the Th1/Th2 Developmental Pathways: Application to Autoimmune Disease Therapy," Cell 80:707-718 (1995).

Metzler, W., et al., "Solution Structure of Human CTLA-4 and Delineation of a CD80/CD86 Binding Site Conserved in CD28," Nature Structural Biology 4(7):527-531 (Jul. 1997).

Parsons, K.R., et al., "Cloning of Cattle CD80," Immunogenetics 49(3):231-234 (1999).

Peach, R.J., et al., "Both Extracellular Immunoglobulin-like Domains of CD80 Contain Residues Critical for Binding T Cell Surface Receptors CTLA-4 and CD28," Journal of Biological Chemistry 270(36):21181-21187 (1995).

Rennert, P. et al., "The IgV domain of human B7-2 (CD86) is sufficient to co-stimulate T lymphocytes and induce cytokine secretion," International Immunology 9(6):805-813 (1997).

Wu, Y., "CTLA-4-B7 Interaction is Sufficient to Costimulate T Cell Clonal Expansion," J. Exp. Med. 185(7):1327-1335 (1997).

Affholter et al. (1998) "Directed evolution of proteins and pathways by DNA shuffling." Book of Abstracts, 216th ACS National Meeting, Boston, Aug. 23-27, BIOT-042.

Agren et al. (1997) "Genetically Engineered Nontoxic Vaccine Adjuvant That Combines B Cell Targeting with Immunomodulation by Cholera Toxin A1 Subunit." J. Immunol 158:3936.

Ahmed (1995) J Bacteriology 177(14):3904-3910.

Ahn et al. (1996) "Human cytomegalovirus inhibits antigen presentation by a sequential multistep process." Proc. Natl. Acad, Sci USA 93:10990.

Aizaki et al. (1998) "Full-Length Complementary DNA of Hepatitus C Virus Genome From an Infectious Blood Sample." Hepatology 27:621-627 (1998).

Aldovinl & Young (1991) "Humorl and cell-mediated immune response to live recombinant BCG-HIV vaccines." Nature 351:479-482.

Ambriovic, A. et al. (1997) "Efficacy of Replication-Defective Adenovirus-Vectored Vaccines: Protection Following Intramuscular Injection Is Linked to Promoter Efficiency in Muscle Representative Cells" Virology 238:, 327-335.

Appel and Harris (1998) "Antibody titers in domestic ferret fills and kits to canine distemper virus vaccines," JAVMA 193:332-333.

Atkins et al. (1996) "Manipulation of the Semliki Forest Virus Genome and Its Potential for Vaccine Construction." Mol Biotechnol 5:33-38.

Attridge et al. (1997) "Oral delivery of foreign antigens by attenuated Salmonella: consequences of prior exposure to the vector strain." Vaccine 15(2): 155-162.

Axon (1998) "Treatment of Helicobacter pylori: future therapeutic and prophylactic perspectives." Gut 43(1):S70-3.

Baba et al., "Identification of CCR6, the Specific Receptor for a Novel Lymphocyte-directed CC Chemokine LARC," The J. of Biolog. Chem. 272 (23): 14893-14898 (1997).

Barry et al. (1994) "Production of monoclonal antibodies by genetic immunization." Short Technical Reports in Biotechniques 16(4):616.

Barry et al. (1995) "Protection against nycoplasma infection using expression-library immunization." Nature 377:632.

Bass et al. (1990) "Hormone Phage: An Enrichment Method for Variant Proteins With Altered Binding Properties." Proteins: Structures, Function and Genetice 8:309-314.

Beattie et al. (1990) "Cloning and characterization of T-cell-reactive protein anigens from Listeria monocytogenes." Infection and Immunity 58(9):2792-2803.

Beck et al., "DNA Sequence Analysis of 66 kb of the Human MHC Class II Region Encoding a Cluster of Genes for Antigen Processing," J. Mol. Biol. 228:433-441 (1992).

Behrens et al. (1996) "Identification and properties of the RNA-dependent RNA polymerase of hepatitis C virus." EMBO J. 15:12-22.

Benham et al. (1997) "Proteasome activity limits the assembly f HMC class 1 molecules after IFN-gamma stimulation," J. Immol 159(2):5896-5904.

Berkhout et al. (1999) "Genetic Instability of Live, Attenuated Human Immunodeficiency Virus Type I Vaccine Strains." J. Virology 73(2):1138-1145.

Bernard et al. (1994) "Transcriptional Control and Cell Type Specificity of HPV Gene Expression." Arch Dermatol 130:210.

Bhatnagar et al. (1982) "Immune response to synthetic peptide analogues of hepatitis B surface antigen specific for the a determinant." Proc Nat'l Acad Sci USA 79:4400-4404.

Bielefeldt-Ohmann, H. et al., "Analysis of a recombinant dengue-2 virus-dengue-3 virus hybrid envelope protein expressed in a secretory baculovirus system," J. Gen. Virol. 78:2723-2733 (1997).

Blachere et al., "Heat Shock Protein-Peptide Complexes, Reconstituted In Vitro, Elicit Peptide-specific Cytotoxic T Lymphyocyte Response and Tumor Immunity," J. Exp. Med. 186:1315-22 (1997).

Blanchard et al. (1998) "Modified vaccinia virus Ankara undergoes limited replication in human cells and lacks several immunomodulatory proteins . . ." J. Gen. Virol 79:1159-1167.

Blaser (1998) "Helicobacter pylori and gastric disease." BMJ 316:1507-1510.

Bloom et al. (1993) Characterization of Chimeric Full-Length Molecular Clones of Aleutian Mink Disease Parvovirus (ADV) . . . J. Virol 67(10):5976-5988.

Bolhuis (1995) J. Biological Chamistry 270(3):26092-26098.

Botstein and Shortle, "Strategies and Applications of in Vitro Mutagenesis," Science 229:1193-1201 (1985).

Boursnell et al. (1997) "A Genetically Inactivated Herpes Simplex Virus Type 2 (Hsv-2) Vaccine Provides Effective Protection against Primary & Recurrent HSV-2 Disease." J. Infect. Dis 175:16-25.

Bray et al. (1989) "Mice Immunized with Recombinant Vaccinia Virus Expressing Dengus Virus Encepha;it is." J. Virol 63:2853-2856

Bridgen and Elliot (1996) "Rescue of a segmented negative-strand RNA virus entirely from cloned complementary DNA's." Proc. Nat'l Acad. Sci USA 93:15400-15404.

Brocke et al. (1996) "Treatment of experimental encephalomyelitis with a peptide analogue of myelin basic protein." Nature 379:343-346.

Brubaker (1991) "The V Antigen of Yersiniae: An Overview." Current Investigations of the Microbiology of Yersinae 12:127-133.

Burger et al. (1995) Proc. of thr Amer Assoc. for Cancer Research 36:522 Abst#3108.

Burke et al. (1999) "Formulation, Stability and Delivery of Live Attenuated Vaccines for Human Use." Crit. Rev. Ther Drig. Carrier Syst 16:1-83.

Burton (1995) "Phage Display." Immunotechnology 1(2):87-94.

Carroll and Moss (1997) "Host range and Cytopathogenicity of the Highly Attenuated MVA Strain of Vaccinia Virus . . . " Virology 238:198-211.

Carter et al., "Improved oligonucleotide site-directed mutagenesis using M13 vectors," Nucl. Acids Res. 13:4431-4443 (1985).

Carter, "Improved Oligonucleotide-Directed Mutagenesis Using M13 Vectors," Methods in Enzymol. 154:382-403 (1987).

Carter, "Site-directed mutagenesis," Biochem. J. 237:1-7 (1986).

Casal (1999) "Use of parvovirus-like particles for vacation and induction of multiple immune response." Biotechnol Appl. Biochem 29:-141-150.

Cathomen et al. (1998) "A matrix-less measles virus is infectious and extensive cell fusion: consequences for propagation in the brain." *EMBO J.* 17(14):3899-3908.

Chang, C., et al. (1999) "Evolution of a cytokine using DNA family shuffling." *Nature Biotechnology* 17:793-797.

Chen et al. "Regulatory T Cell Clones Induced by Oral Tolerance: Suppression of Autoimmune Encephalomyelitis." *Science* 265:1237-1240.

Chen et al., "Discontinuous epitopes of hepatitis B surface antigen derived from a filamentous phase peptide library," Proc. Nat'l. Acad. Sci. USA 93:1997-2001 (1996).

Chin et al. (1993) "Functions and Regulation of the Human Miltidrug Resistance Gene." *Adv. Cancer Res..* 60:157-180.

Choate and Khavari (1997) "Sustainability of Keratinocyte Gene Transfer and Cell Survival in Vivo." *Human Gene Therapy* 8:895-901.

Christians, F.C. et al., "Directed evolution of thymidine kinase for AZT phosphorylation using DNA family shuffling," Nature Biotechnology 17:259-264 (1999).

Chu et al. (1995) "A Vaccina Virus-Vectored Hantaan Virus Vaccing Protects Hamsters from Challenge with Hantaan and Seoul Viruses but not Pumala Virus." *J. Virol* 69:6417.

Clackson et al. (1994) "In vitro selection from protein and peptide libraries." *Trends Biotechnol* 12(5): 173-184.

Coco et al., (2001) "DNA shuffling method for generating highly recombined genes and evolved enzymes" *Nature Biotechnology* vol. 19 pp. 354-359.

Collman et al. (1992) "An Infectious Molecular Clone of an Unusual Macrophage- Tropic and Highly Cytopathic Strain of Human Immunodeficiency Virus Type 1." *J. Virol* 66(12):7517-7521.

Conry et al. (1996) "Selected strategies to augment polynucleotide immunization." *Gene Therapy* 3(1):67-74.

Conry et al. (1994) "Immune response to a carinoembryonic antigen polynucleotide vassine." *Cancer Res.* 54:1164-1168.

Coppel et al. (1993) "idenification of a coda clone encoding a mature blood stage antigen of Plasmodium falciparum by immunization of mice with bacterial lysates." *EMBO Journal* 3)2):403-407.

Cote et al. (1986) "Protection of Chimpanzees from Type B Hepatitis by Immunization with Woodchuck Hepatitis Virus Surface Antigen." *J. Virol* 60:895-901.

Courvalin et al. (1995) "Gene transfer from bacteria to mammalian cells." *C.R. Acad. Sci III* 18:1207-1212.

Crabtree (1998) "Eradication of chronic Helicobacter pylori infection by therapeutic vaccination." *Gut* 43:7-8.

Craiu et al., "Two distinct proteolytic processes in the generation of a major histocompatibility complex class I-presented peptide," Proc. Nat'l. Acad. Sci. USA 94:10850-10855 (1997.

Crameri & Stemmer (1993) "10(20)-fold aptamer library amplification without gel purification." *Nucleic Acids Research* 21(18):4410.

Crameri, A. et al., "Combinatorial Multiple Cassette Mutagenesis Creates All the Permutations of Mutant and Wild-Type Sequences," *Biotechniques* 18:194-195 (1995).

Crameri, A. et al., "Construction and evolution of antibody-phage libraries by DNA shuffling," *Nature Medicine* 2:100-103 (1996).

Crameri, A. et al., "DNA shuffling of a family of genes from diverse species accelerates directed evolution," *Nature* 391:288-291 (1998) (2-287-1PC & 2-251PC).

Crameri, A. et al., "Improved Green Fluorescent Protein by Molecular Evolution Using DNA Shuffling," *Nature Biotechnology* 14:315-319 (1996).

Crameri, A. et al., "Molecular evolution of an arsenate detoxification pathway by DNA shuffling," *Nature Biotechnology* 15:436-438 (1997).

Cresswell & Hughes, "Protein degradation: The ins and outs of of the matter,"Curr. Biol. 7:R552-R555 (1997).

Cwirla et al. (1990) "Peptides on Phage: A vast library of peptides for identifying ligands." *Proc. Natl'l Acad Sci USA* 87:6378-6382.

Davis et al (1995) "DNA-based immunization." *Molecular and Cell Biology of Human Gene Therapeutics* 5:368-387.

Davis et al. (1989) "In vitro Synthesis of Infectious Venezuelar Equine Encephalitis Virus RNA from a cDNA Clone: Analysis of a Viable Deletion Mutant." *Virology* 171:189-204.

Davis et al. (1997) "DNA-Based immunization against hepatitis B surface antigen (HBsAg) in Normal and HBsAg-transgenic mice." *Vaccine* 15(8) 849-822.

Deng et al. (1997) "Sustainable cutaneous gene delivery." *Nature Biotechnol* 15:1388-1391.

Devlin et al. (1990) "Random Peptide Libraries: A Source of Specific Protein Binding Molecules." *Science* 249:404-406.

Dieu et al., "Selective Recruitment of Immature and Mature Dendritic Cells by Distinct Chemokines Expressed in Different Anatomic Sites," J. Exp. Med. 188:373-386 (1998).

DiMarco et al. (1997) "Agnostic and antagonistic variants of ciliary neurothrophic Factor (CNTF) Reveal functional differences between mambrean-bound and soluble CNTF Alpha-receptors." *J Biol. Chem.* 272(37):23069-23075.

Donovan et al. (1987) "Genes Encoding Spore Coat Polypeptides from *Bacillus subtilis*." J. Mol Biol 196:1-10.

Drabkin et al. (1996) "Amber Suppression in Mammalian Cells Dependent upon Expression of an *Escherichia coli* Aminoacyl-tRNA Synthetase Gene." *Mol. Cell Biol.* 16(3):907-913.

Dubols et al. (1998) "Immunization against Natural Helicobacter pylori Infection in Nonhuman Primates." *Infect. Immun.* 66:4340-4346.

Dunn (1996) "Phage display of proteins." *Curr Opin Biotechnology* 7(5):547-553.

Eghtedarzadeh and Henikoff, "Use of oligonucleotides to generate large deletions," Nucl. Acids Res. 14:5115 (1986).

Engels and Ackermann (1996) "Pathogenesis of ruminant herpesvirus infections." *Vet Microbiol* 53:3-15.

Felici, Franco et al., "Peptide and protein display on the surface of filamentous bacteriophage," Biotechnol. Annu. Rev. 1:149-83 (1995).

Fields et al., "Crystal structure of a T-cell receptor B-chain complexed with a superantigen," Nature 384:188-192 (1996).

Fox et al. (1996) "Anaerobic bacteria as a delivery system for cancer gene therapy: In vitro activation of 5-fluorocytosine by genetically engineered clostridia." *Gene Ther* 3:173-178.

Francisco, Joseph A. et al., "Production and fluorescence-activated cell sorting of *Escherichia coli* expressing a functional antibody fragment on the external surface," Proc. Nat'l. Acad. Sci. USA 90:10444-10448 (1993).

Frankel and Young (1998) "HIV-1 Fifteen Proteins and an RNA." *Annu. Rev. Biochem* 67:1-25.

Freeman et al., "B7-1 and B7-2 Do Not Deliver Identical Costimulatory Signals, Since B7-2 but Not B7-1 Preferentially Costimulates the Initial Production of IL-4," Immunity 2:523 (1995).

Fritz et al. "Oligonucleotide-directed construction of mutations: a gapped duplex DNA procedure without enzymatic reactions in vitro," Nucl. Acids. Res. 16:6987-6999 (1988).

Fritz et al. "Oligonucleotide-directed construction of mutations: a gapped duplex DNA procedure without enzymatic reactions in vitro," Nucl. Acids. Res. 16:6987-6999 (1988).

Gaczynska et al., Proteasome Subunits X and Y alter Peptidase Activities in Opposite Ways to the Interferon-γ-induced Subunits LMP2 and LMP7*,J. Biol. Chem. 271:17275-17280 (1996).

Galler et al. (1997) "The Yellow fever 17D vaccine virus: molecular basis of viral attnuation and its use as an expression vector." *J. Med. Biol. Res.* 30:157-168.

Galocha et al. (1997) "The Active Site of ICP47, a Herpes Simple Virus-encoded Inhibitor of the Major Histocompatibility Complex . . . " *J. Exp. Med* 185:1565-1572.

Garnett and Grenfell (1992) "The epidemiology of varicella-zoster virus infections: the influence of varicella on the prevalence of herpes zoster." *Epidemiol. Infect* 108:513-528.

Gates, C.M. et al., "Affinity Selective Isolation of Ligands from Peptide Libraries Through Display on a lac Repressor 'Headpiece Dimer'" *J. Mol. Biol.* 255:1-14 (1996).

Geigenmuller et al. (1997) "Construction of a Genome-Length cDNA Clone for Human Astrovirus Serotype 1 and Synthesis of Infectious RNA Transcrips." *J. Virol* 71:1713-1717.

Goldman et al. (1999) Molecular Cloning and Expression of Major Structural Protein . . . *J. Virol.* 73:4465-4469.

Gritsun et al. (1998) "Development and analysis of a tick-bone encephalitis virus infectious clone using a novel and rapid strategy." *J Virol. Methods* 76:109-120.

Groettrup et al. "The subunits MECL-1 and LMP2 are mutually required for incorporation into the 20S proteasome," Proc. Natl'. Acad. Sci. USA 94:8970-8975 (1997).

Groettrup et al., "A third interferon-γ-induced subunit exchange in the 20S proteasome," Eur. J. Immunol. 26:863-869 (1997).

Groux et al., "A CD4+ T-cell subset inhibits antigen-specific T-cell responses and prevents colitis," Nature 389:737 (1997).

Grundstrom et al.,"Oligonucleotide-directed mutagenesis by microscale 'shot-gun' gene synthesis," Nucleic Acids Res. 13:3305-3316 (1985).

Gualano et al. (1998) "Identification of a major determinant of mouse neurovirulence of dengue virus typw 2 using stably cloned genomic-length cDNA," *J. Gen. Virol.* 79:437-466.

Guo et al. (1998) "Susceptibility to recombination rearrangements of a chimeric plum pox potyvirus genome after insertion of a foreign gene." *Virus Res* 57:183-195.

Halminen et al. (1997) "Expression of MXA Protein in Blood Lymphocytes Discriminates between Viral and Bacterial Infections in Febrile Children." *Pediatric Research* 41:647-650.

Han, Xiaoliang et al., "Ligand-directed retroviral targeting of human breast cancer cells," Proc. Natl. Acad. Sci USA 92:9747-9751 (1995).

Hanes, Jozef and Andreas Pluckthun., "In vitro selection and evolution of functional proteins by using ribosome display," Proc. Nat'l. Acad. Sci. USA 94(10):4937-42 (1997).

Haq et al. (1995) "Oral Immunization with a Recombinant Bacterial Antigen Produced in Transgenic Plants." *Science* 268:714-716.

Haralambiev (1967) "Immunogenicity Studies on a Inactivated IBR Vaccine Administered Into the Nasal Mucosa." *Acta Vet Acad Sci Hung* 26:215-217.

Harrington et al. (1992) "An outbreak of Respiratory Syncytial Virus in a Bone Marrow Transplant Center." *J. Infect Dis.* 165:987-993.

HCJ Ertl et al., (1996) "Genetic Immunization" *Viral Immunization* vol. 9, No. 1, pp. 1-9.

He et al., "Antibody-ribosome-mRNA (ARM) complexes as efficient selection particles for in vitro display and evolution of antibody combining sites," Nucl. Acids Res. 25(24):5132-4 (1997).

He et al. (1998) "The Paramyxovirus SV5 Small Hydrohobic (SH) Protein Is Not Essential for Virus Growth in Tissue Culture Cells." *Virology* 250:30-40.

Hedstrom et al. (1994) "Prospects and strategies for development of DNA vaccines against malaria." 59th Forum in Immunology 476-482.

Hensel and Lubitz (1997) Vaccination by Aerosols: Modulation of Clearance Mechanism in the Lung. *Behring. Inst. Mitt.* 98:212-219.

Hilgers et al. (1990) "Caco-2 Cell Monolayers as a Model for Drug Transport Across the Intestinal Mucosa." *Pharmaceutical Res.* 7(9):902-910.

Hill et al., "Phage presentation," Mol Microbiol 20(4):685-92 (1996).

Hoffman and Banerjee (1997) "An Infectious Clone of Human Parainfluenza Virus Type 3." *J Virol.* 71:4272-4277.

Hohol et al. (1996) "Three-year Open Protocol Continuation Study of Oral Tolerization with Myelin Antigens in Multiple Sclerosis and Design of a phase III Pivotal Trial." *Ann. N.Y. Acad Sci.* 778:243-250.

Holzmann, H. et al., "Molecular epidemiology of tick-borne encephalitis virus: cross-protection between European and Far Eastern subtypes," Vaccine 10:345 (1992).

Hopkins and Yoder (1986)"Reversion to Virulence of Chicken-Passaged Infectious Bronchitis Vaccine Virus." *Avain Dis.* 30:221-223.

Hourvitz et al. (1996) "Reactogenicity and immunogenicity of a new recombinant hepatitis B Vaccine containing Pre S Antigens." *J Virol Hepatitis* 3:37-42.

Howard (1998) "Chemistry of the future: Exploitation of the power of biology." Book of Abstracts, 216th ACS National Meeting, Boston, Aug. 23-27, BTEC-045 Apst #: 528494.

Hristov and Karadjov (1975) *Vet Med Nauki* 13:5.

Huang, Sharon K.S. et al., "Antibody Responses to Melanoma/Melanocyte Autoantigens in Melanoma Patients," J. Invest. Dermatol. 111:662-7 (1998).

Hui, George S.N. et al., "Dominance of Conserved B-Cell Epitopes of the Plasmodium falciparum Merozoite Surface Protein, MSP1, in Blood-Stage Infections of Naïve Aotus Monkeys," Infect. Immun. 64: 1502-1509 (1996).

Hulskotte et al. (1998) "Towards an HIV-1 vaccine: lessons from studies in macaque models." *Vaccine* 16:904-915.

Hurtado et al. (1996) "Identification of Domains in Canine Parvovirus VP2 Essential for the Accembly of Virus-Like Particles." *J. Virol* 70:5422-5429.

Iacono-Connors et al., Virus Res. 43:125-136 (1996).

Irvine, K.R. et al., "Cytokine Enhancement of DNA Immunization Leads to Effective Treatment of Established Pulmonary Metastases," Journal of Immunology, 156:238-245 (1996).

Jia et al. (1995) "A Novel virant of avain infectious bronchitis virus resulting from recombination among three different strains." *Arch Virol* 140:259-271.

Jiang et al. (1999) "Heterotypic protection from rotavirus infection in mice vaccinated with virus-like particles." *Vaccine* 17:1005-1013.

Jiang et al., "Subtraction hybridization identified a novel melanoma differentiation associated gene, mda-7, modulated during human melanoma differentiation, growth and progression," Oncogene 11:2477 (1995).

Jiang et al., "The melanoma differentiation associated gene mda-7 suppresses cancer cell growth," Proc. Nat'l. Acad. Sci. USA 93:9160 (1996).

Jin et al. (1998) "Recombinant Human Respiratory Synctial Virus (RSV) from cDNA and Construction of Subgroup A and B Chimeric RSV." *Virology* 251:206-214.

Johnston, et al. (1997) "Genetic to genomic vaccination" vol. 15, No. 8 pp. 808-809.

Kang et al. (1999) "Development of HIV/AIDS Vaccine Using Chimeric gag-env Virus-like Particles." *Biol. Chem* 380:353-364.

Karandikar et al., "CTLA-4: A Negative Regulator of Autoimmune Disease," J. Exp. Med. 184:783 (1996).

Keck. Et al. (1988) "In Vivo RNA-RNA Recombination of Coronavirus in Mouse Brain." *J.Virol.* 62:1810-1813.

Keenan et al., "Lack of Protection following immunisation with H. pylori outer membrane vesicles highlights antigenic differences between H. felis and H. pylori," FEMS Microbiol Lett. 161:21-7 (1998).

Khavari, (1997) "Therapeutic gene delivery to the skin" Molecular Medicine Today, Dec. 1997: 533538.

Khavari and Krueger (1997) "Cutaneous Gene Therapy." *Adv Clin Res Dematologic Clinics* 15(1): 27-35.

Khusmith et al. (1991) "Protection against malaria by vaccination with sporozolite surface protein 2 plus CS protein." *Science* 252:715.

Kim et al., "In Vivo Engineering of a Cellular Immune Response by Coadministration of IL-12 Expression Vector with a DNA Immunogen," J. Immunol. 158:816 (1997).

Kim, et al. (1997) "Development of a multicomponent candidate vaccine for HIV-1" Vaccine, vol. 15 No. 8 pp. 879-883.

Kinney et al. (1997) "Construction of Infectious cDNA Clones for Dengue 2 Virus: Strain 16681 and Its Attenuated Vaccine Derivative, Strain PDK-53." *Virology* 230:300-308.

Kinney et al., "Recombinant Vaccinia Virus/Benezuelan Equine Encephalitis (VEE) Virus Protects Mice from Peripheral VEE Virus Challenge," J. Virol. 62:4697 (1998).

Kleanthous et al., "Vaccine development against infection with Helicobacter pylori," Br. Med. Bull. 54:229-41 (1998).

Klinman et al., "CpG motifs present in bacterial DNA rapidly induce lymphocytes to secrete interleukin 6, interleukin 12 and interferon ☐," Proc. Nat'l. Acad. Sci. USA 93:2879 (1996).

Klinman, D.M. et al., "Contribution of CpG Motifs to the Immunogenicity of DNA Vaccines," Journal of Immunology, 158:3635-3639 (1997).

Kobayashi et al., "Identification and Purification of Natural Killer Cell Stimulatory Factor (NKSF), A Cytokine with Multiple Biologic Effects an Human Lymphocytes," J. Exp. Med. 170:827 (1989).

Kobyashi, Yuzuru et al., "Antigenic Analysis of Japanese Encephalitis Virus by Using Monoclonal Antibodies," Infect. Immun. 44:117 (1984).

Kochel, Tadeusz et al., "Inoculation of plasmids expressing the dengue-2 envelope gene elicit neutralizing antibodies in mice," Vaccine 15:547-552 (1997).

Kodama et al., "Type I macrophage scavenger receptor contains -helical and collagen-like coiled coils," Nature 343:531-535 (1990).

Konishi et al., "A Highly Attenuated Host Range-Restricted Vaccinia Virus Strain, NYVAC, Encoding the prM, E and NS1 Genes of Japanese Encephalitis Virus Prevents JEV Viremia in Swine," Virology 190:454 (1992).

Koopman et al., "Generation, intracellular transport and loading of peptides associated with MHC class 1 molecules," Curr. Opin. Immunol. 9:80-88 (1997).

Kramer and Fritz, "Oligonucleotide-Directed Construction of Mutations via Gapped Duplex DNA," Methods in Enzymol. 154:350-367 (1987).

Kramer et al. "Improved Enzymatic in vitro reactions in the gapped duplex DNA approach to oligonucleotide-directed construction of mutations," Nucl. Acids Res. 16:7207 (1988).

Kramer et al., "Different Base/Base Mismatches Are Corrected with Different Efficiencies by the Methyl-Directed DNA Mismatch-Repair System of *E. coli*," Cell 38:879-887 (1984).

Kramer et al., "The gapped duplex DNA approach to oligonucleotide-directed mutation construction," Nucl. Acids Res. 12:9441-9456 (1984).

Krieg et al., "CpG motifs in bacterial DNA trigger direct B-cell activation," Nature 374-546 (1995).

Krieger, M. et al., "Molecular Flypaper, Atherosclerosis, and Host Defense: Structure and Function of the Macrophage Scavenger Receptor," Cold Spring Harbor Symposia on Quantitative Biology 57:605-609 (1992).

Kruse et al., "Conversion of human interleukin-4 into a high affinity antagonist by a single amino acid replacement," EMBO J. 11:3237-3244 (1992).

Kuchroo et al., "B7-1 and B7-2 Costimulatory Molecules Activate Differentially the Th1/Th2 Developmental Pathways: Application to Autoimmune Disease Therapy," Cell 80:707 (1995).

Kunkel et al., "Rapid and Efficient Site-Specific Mutagenesis without Phenotypic Selection," Methods in Enzymol. 154:367-382 (1985).

Kunkel, "The efficiency of oligonucleotide directed mutagenesis" Nucleic acids & Molecular Biology 2: 124-135 (1988).

Kunkel, "Rapid and Efficient Site-Specific Mutagenesis without Phenotypic Selection," Proc. Nat'l. Acad. Sci. USA 82:488-492 (1985).

Lagranderie et al. (1993) "BCG-induced protection in guiena pigs vaccinated and challenged via the respiratory route." *Tubercle and Lung Disease* 74:38-46.

Lai et al. (1991) "Infectious RNA transcribed from stably cloned full-length cDNA of dengue type 4 Virus." *Proc. Nat'l Acad. Sci. USA* 88:5139-5143.

Lanar et al. (1996) "Attanuated Vaccinia Virus-Circumsporoziote Protein Recombinants Confer Protection against Rodent Malaria." *Infect Immun* 64:1666-1671.

Lanciotti et al. (1994) "Molecular evolution and epidemology of dengue-3 viruses." *J Gen Virol.* 75:65-75.

Laud et al., *Human Immunol.* 50:91-102 (1996).

Larsen et al., Long Term acceptance of Skin and Cardiac Allografts After Blocking CD40 and CD28 Pathways, Nature 381:434 (1996).

Leary et al., "Active Immunization with Recombinent V Antigen from Yersinia Pestis Protects Mice against Plague," Infect. Immun. 3:2854 (1995).

Lee et al., (1997) "Generation of an Infectious cDNA of a highly cardiovirulent coxsakievirus B3(CVB3m) and comparison to other infectious CVB cDNAs." *Virus Res* 50:255-235.

Lee et al., "Optimal Induction of Hepatitis C Virus Envelope-Specific Immunity by Bicistronic Plasmid DNA Inoculation with the Granulocyte-Macrophage Colony-Stimulating Facter Gene," *J. Virol* 72:8430-6 (1998).

Lehrer et al. (1998) "Immunotherapy with Mycobacterium vaccae in the treatment of psoriasis." *FEMS Immunol. Med. Microbiol.* 21:71-77.

Leung et al. (1989) *Technique* 1(1):11-15.

Li et al. (1997) "Expression of the Human Papillomavirus Type 11 L1 Capsid Protein in *Escherichia coli* . . . "*J. Virol* 71 (4):2988-2995.

Li et al., "Cloning and functional characterization of a subunit of the transporter associated with antigen processing," *Proc. Natl. Acad. Sci USA* 94:8708-8713 (1997).

Liao et al. (1990) *Gene* 107-111.

Liao et al., STRL22 is a Receptor for the CC Chemokine MIP-3α, Biochem. and Biophys. Comms. 236:212-217 (1997).r.

Liblau et al. "Th1 and Th2 CD4' cells in the pathogenesis of organ-specific autoimmune diseases," *Immunol. Today* 16:34-38 (1995).

Liem et al. (1994) *Nucleic Acids Res* 22(9):1613-1619.

Lieschke et al., "Bioactive murine and human interleukin-12 fusion proteins which retain antitumor activity in vivo," Nature Biotech. 15:35 (1997).

Limbach and Paoletti (1996) "Non-replicating expression vectors: applications in vaccine development and gene therapy." *Epidemol. Infect.* 116:241-256.

Lowe et al. (1997) "Human Papillamavirus Typw 2 (HPV-11) Nutralizing Antibobies in the Serum and Genital Mucosal Secretions of African Green Monkeys Immunized with HPV-11 Virus-like particles Expressed in Yeast." *J. Invect Dis* 176:1141-1145.

Lowman, Henry B. and Jame A. Wells, "Affinity Maturation of Human Growth Hormone by Monovalent Phage Display," *J. Mol. biol.* 234:564-578 (1993).

Lowman, Henry B. and James A. Wells, "Monovalent Phage Display: A Method for Selecting Variant Proteins from Random Libraries," Methods: A Companion to Methods Enz. 3(3):205-216 (1991).

Lu, Zhijian et al., "Expression of Thioredoxin Random Peptide Libraries on the *Escherichia coli* Cell Surface as Functional Fusions to Flagellin: A System Designed for Exploring Protein-Protein Interactions." Bio/Technology 13:366-372 (1995).

Luytjes et al. (1989) "Amplification, Expressionand Packaging of a Foreign Gene by Influenza Virus." *Cell* 59:1107-1113.

MacKay et al. (1981) "Production of immunology active surface of hepatitis B virus by *Escherichia coli*." *Proc. Natl. Acad. Sci USA* 78:4510-4514.

Mandl et al. (1997) "Infectious cDNA clones of tick-borne encephalitis virus European subtype protopic strain Neudoerfl and high virulence strain Hypr." *J. Gen. Virol* 78:1049-1057.

Marchetti, Marta et al., "Protection against Helicobacter pylori infection in mice by intragastric vaccination with H. pylori antigens is achieved using a non-toxic mutant of *E. coli* heat-labile enterotoxin (LT) as adjuvant," Vaccine 16:33-7 (1998).

Marusina et al., "Allelic Variation in the Mouse Tap-1 and Tap-2 Transporter Genes," *J. Immunol.* 158:5251-5256 (1997).

Mattheakis, Larry C. et al.,"An in vitro polysome display system for identifying ligands from very large peptide libraries," *Proc. Nat'l. Acad. Sci. USA* 91(19):9022-6 (1994).

McAtee, C. Patrick et al., "Identification of Potential Diagnostic and Vaccine Candidates of Helicobacter pylori by "Proteome" Tehnologies," Helicobacter 3:163-9 (1998).

McAtee. C. Patrick et al., "Identification of Potential Diagnostic and Vaccine Candidates of Helicobacter pylori by Two-Dimensional Gel Electrophoresis, Sequence Analysis, and Serum Profiling," Clin. Diagn. Lab. Immunol. 5:537-42 (1998).

McCutcheon et al. "A senstive ELISPOT assay to detect low-frequency human T lymphocytes,", *J. Immunol.* Methods 210:149-66 (1997).

McGregor, Duncan, "Selection of Proteins and Peptides from Libraries Displayed on Filamentous Bacteriophage," Mol Biotechnol. 6(2):155-62 (1996).

Melen et al., "Enzymatic Characterization of Interferon-Induced Antiviral GTPases Murine Mx1 and Human MxA Proteins," J. Biol, Chem. 269:2009-2015 (1994).

Mendoza, R.B. et al. (1997) "Immunostimulatory effects of a plasmid expressing CD40 ligand (CD154) on gene immunization" J. Immunol Dec. 15;159(12):5777-81 Abstract Only.

Metz et al. (1996) "Bicistronic and Two-Gene Retroviral Vectors for Using MDR1 as a Selectable Market and a Therapeutic Gene." *Virology* 217:230-241.

Meulenberg et al. (1998) "An Infectious cDNA Clone Porcine Reproductive and Respiratory Syndrome Virus." *Coronaviruses and Arteriviruses* 440:199-206.

Meulenberg et al. (1998) "Infectious Transcrips from Cloned Genome-Length cDNA of Porcine Reproductive and Respiratory Syndrome Virus." *J. Virol.* 72:380-387.

Meyer et al. (1998) "Bovine herpesvirus type 1 glycoprotein H is essential for penetration and and propagation in cell culture." *J. Gen Virol.* 79:1983-1987.

Minshull, J. and Willem P.C. Stemmer, "Protein evolution by molecular breeding," *Current Opinion in Chemical Biology* 3:284-290 (1999).

Mittelholzer et al. (1997) "Generation of cytopathogenic RNA of classical swine fevor in persistently infected porcine cell lines." *Virus Res* 51:125-137.

Monaco, "Pathways for the processing and presentation of antigens to T cells," J. Leukocyte Biol. 57:543-57 (1995).

Morita et al. (1987) "Recombinant vaccinia virus LC16m0 or LC1m8 that expresses hepatitis B surface antigen while preserving the attention of the parental virus." *Vaccine* 5:65-70.

Mosmann and Coffman, Adv. Immunol. 46:111 (1989).

Moss (1994) "Replicating and Host-Restricted Non-Replicating Vaccina Virus Vectors for Vaccine Development." *Dev. Biol. Stand* 82:55-63.

Mundt and Vakharia (1996) "Synthetic transcripts of double-stranded Birnavirus genome are infectious." *Proc Nat'l Acad. Sci USA* 93:11131-11136.

N. Miller et al., (1995) "Targeted vectors for gene therapy," FASEB J., 9, pp. 190-199.

Nakamaye and Eckstein, "Inhibition of restriction endonuclease Nci 1 cleavage by phosphorothioate groups and its application to oligonucleotide-directed mutagenesis," Nucl. Acids Res. 14:9679-9698 (1986).

Nambiar et al., "Total Synthesis and Cloning of a Gene Coding for the Ribonuclease S Protein," Science 223:1299-1301 (1984).

Nazerian et al. (1996) "Protection and synerhism by Recombinant Fowl Pox Vaccines Expressing Genes from Marek's Disease Virus." *Avian Dis.* 40:368-376.

Nemoto, Naoto et al., "In vitro virus: Bonding of mRNA bearing puromycin at the 3'-terminal end to the C-terminal end of its encoded protein on the ribosome in vitro," FEBS Lett. 414(2):405-8 (1997).

Ness, J. et al., (1999) "*DNA shuffling of subgenominc sequences of subtilisin.*" *Nature Biotechnology* 17:893-896.

Neurath, A.R. et al., "Monoclonal Antibodies to Hepatitis BSurface Antigen (HBsAg) with Anti-a Specificity Recognize A Synthetic Peptide Analogue (S135-155) with Unmodified Lysine (141)," J. Virol. Methods 9:341-346 (1984).

Ni and Barrett, "Nucleotide and deduced amino acid sequence of the structural protein genes of Japanese encephalitis viruses from different geographical locations," J. Gen. Virol. 76:401 (1995).

Notka et al. (1999) "Construction and Characterization of Recombinant VLPs and Semliki-Forest Virus Live Vectors for Comparative Evaluation in the SHIV Monkey Model." *Biol Chem* 380:341-352.

O'Neil, Karyn T. et al., "Phage display: protein engineering by directed evolution," Curr. Opin. Struct. Biol. 5(4):443-9 (1995).

Oda Kobe J. Med. Sci. 22:123 (1976).

Oggioni, M.R. and Pozzi, G., "A host-vector system for heterologous gene expression in *Streptococcus gordonii*," Gene 169:85-90 (1996).

Orme (1997) "Progress in the development of new vaccines against tuberculosis." *Int. J. Tuberc. Jung. Dis* 1:95-100.

Ortmann et al., "A Critical Role for Tapasin in the Assembly and Function of Multimeric MHC Class 1-TAP Complexes," Science 277: 1306-1309 (1997).

Paoletti et al. (1995) "Highly Attenuated Poxvirus: HYVAC, ALVAC and TROVAC," *Dev Biol Stand* 84:159-163.

Park and RajBhandary (1998) "Tatracycline-Regulated Suppression of Amber Condons in Mammalian Cells." *Mol Cell Biol* 18:4418-4425.

Parren, Paul W.H.I. et al., "Relevance of the antibody response against human immunodeficiency virus type 1 envelope to vaccine design," Immunol. Lett. 57:105-112 (1997).

Parronchi et al., "IL-4 and IFN (☐ and ☐) Exert Opposite Regulatory Effects on the Development of Cytolytic Potential by Th1 or Th2 Human T Cell Clones," J. Immunol. 149:2977 (1992).

Pascopella et al. (1994) "Identification of a genomic fragment of *Mycobacterium tuberculosis*." *Infectious Agents & Disease* 2:282-284.

Pascopella et al. (1994) "Use of In Vivo complementation in *Mycobacterium tuberculosis* to identify a genomic fragment associated with virulence." *Infection & Immunity* 62(4):1313-1319.

Pasquini S. et al. (1997) "Cytokines and costimulatory molecules as genetic adjuvants" Immunol Cell Biol Aug: 75(4):397-401, Abstract Only.

Patten, P.A. et al., "Applications of DNA Shuffling to Pharmaceuticals and Vaccines," Current Opinion in Biotechnology, 8:724-733 (1997).

Paul and Seder, "Lymphocyte Responses and Cytokines," Cell 76:241 (1994).

Paulusma et al. (1996) "Congenital jaundice in rats with a mutation in a multidrug resistance-associated protein gene." *Science* 271:1126-1128.

Pettetier, Joelle N., (2001) "A Rachitt for our toolbox" Nature Biotechnology vol. 19, p. 314-315.

Peng et al. (1998) "Papillomavirus Virus-like Particles Can Deliver Defined CTL Epitopes to the MHC Class 1 Pathway." *Virology* 240:147-157.

Penzes et al. (1996) "Replication and Packaging of Coronavirus Infectious Bronchitis Defective RNSa Lacking a Long Open Reading Frame." *J. Virol* 70:86660-8668.

Phizicky, Eric M. et al., "Protein-Protein Interactions: Methods for Detection and Analysis," Microbiol Rev. 59(1):94-123 (1995).

Pisetsky, D.S., "Immune Activation by Bacterial DNA: A New Genetic Code," Immunity 5: 303-310 (1996).

Pletnev, A.G. et al., Chimeric Tick-Borne Encephalitis and Dengue Type 4 Viruses: Effects of Mutations on Neurovirulence in Mice, J. Virol. 67(8):4956-4963 (1993).

Polo et al. (1999) "Stable alphavirus packaging cell lines for Sidbis virus-and Semlike Forest virus-derived vectors." *Proc Nat'l Acad. Sci USA>* 96:4598-4603.

Porcell (1995) *Adv. Immunol* 59:1.

Powis et al., "Polymorphism in a second ABC transporter gene located within the class II region of the human major hisotcompatibility complex,"Proc. Nat'l. Acad. Sci. USA 89:1463-1467 (1996).

Premack et al. (1996) *Nature Med.* 2:1174.

Pryor et al. (1998) "Growth restriction of dengue virus type 2 by site-specific mutagenesis of virus-encoded glycoproteins." *J. Gen Virol.* 79:2631-2639.

Punnonen et al. (1998) "Evolution of genetic vaccines by DNA shuffling." Keystone Symposia on Molecular and Cellular Biology, Molecular Aspects of Viral Immunity, Abstract #227, Tamarron, CO, Feb. 16-20, 1998.

Punnonen et al. (1997) "Evolution of DNA Vaccine vectors by gene shuffling." The First Gordon Conference on Genetic Vaccines/DNA Vaccines, Plymouth State College, Plymouth, NH, Jul. 20-25, 1997.

Punnonen et al. *J. Exp. Med.* 185:993-1004.

Punnonen et al., "Interleukin 13 induces interleukin 4-independent IgG4 and IgE synthesis and CD23 expression by human B cells," Proc. Nat'l. Acad. Sci. USA 90:3730 (1993).

Puri et al. (1998) "Complete Nucleotide Sequences Analysis of a Western Pacific Dengue-1 Virus Strain." *Virus Genes* 17:85-88.

Racke, Michael K. et al., "Cytokine-induced Immune Deviation as a Therapy for Inflammatory Autoimmune Disease," J. Exp. Med. 180:1961-66 (1994).

Rahden-staron et al. (1991) *Biochem & Biophy Res. & Commun.* 177(2):597-602.

Raj and Jones (1997) "Growth of infectious bronchitis virus vaccines in oviducts derived from oestrogen-treated chicks and embryos." *Vaccine* 15:163-168.

Reiser et al., "Cloning and expression of a cDNA for the T-cell-activating protein TAP," Proc. Nat'l. Acad. Sci. USA 85:2255-2259 (1988).

Roden et al. (1996) "In Vitro Generation and TypeSpecific Neutralization of a Human Papillomavirus Type 16 Viron Pseudotype." *J. Virol.* 70:5875-5883.

Roggenkamp et al., "Passive Immunity to Infection with Yersinia spp. Mediated by Anti-Recombinant V Antigen is Dependent on Polymorphism of V Antigen," Infect. Immun. 65:446 (1997).

Roncarolo et al. "Human T- and B-cell functions in SCID-hu mice," Semin. Immunol. 8: 207 (1996).
Sagazio et al. (1998) "Antigenic characterization of canine parvovirus strains isolated in Italy." *J. Virol. Methods* 73:197-200.
Saggio et al. (1995) "CNFT Variants with increased biological potency and receptor selectivity define a functional site of receptor interaction." *EMBO Journal* 14(13):3045-3054.
Sakmar and Khorana, Total synthesis and expression of a gene for the a-subunit of bovine rod outer segment guanine nucleotide-binding protein (transducin), Nucl. Acids Res. 14:6361-6372 (1988).
Sanz et al. (1994) "Genetic heterogeneity of the attachment glycoprotein G among A respiratory syncytial viruses." *Virus Res* 33:203-217.
Saurmann et al. (1990) "Molecular Cloning and Characterization of a German HIV-1 Isolate." *AIDS Res. Hum Retroviruses* 6:813-823.
Sayers et al. "Strand specific cleavage of phosphorothioate-containing DNA by reaction with restriction endonucleases in the presence of ethidium bromide,", Nucl. Acids Res. 16:803-814 (1988).
Sayers et al., "5'-3' Exonucleases in phosphorothioate-based oligonucleotide-directed mutagenesis," Nucl. Acids Res. 16:791-802 (1988).
Schatz, Peter J. et al., "[10] Screening of Peptide Libraries Linked to lac Respressor," Methods Enzymol. 267:171-91 (1996).
Schmaljohn, A.L. et al., "Non-neutralizing monoclonal antibodies can prevent lethal alphavirus encephalitis," Nature 297:70 (1982).
Schwarz et al. (1957) "Modification of Infevtious Bovine Rhinotrachetis (IBR) Virus in Tissue Culture and Development of a Vaccine." *Proc Soc Exp. Biol Med.* 96:453-458.
Schwarz et al. (1958) "Propagation and Modification of Infactious Bovine Rhinotrachetis (BR) Virus in Porcine Kidney Tissue Culture." *Proc. Soc. Exp. Biol. Med* 97:680-683.
Scott, Jamie K. and George P. Smith, "Searching for Peptide Ligands with an Epitope Library," Science 249:386-388 (1990).
Seliger et al., "TAP off—tumors on," Immunol. Today 18: 292-299 (1997).
Sharma and Graham (1982) "Influence of Material Antibody on Efficacy of Embryo Vaccination with Cell-Associated ans Cell-Free Marek's Disease Vaccine." *Avian Dis.* 26:860-870.
Sheu et al. (1995) "Deletion or alteration of hydrophobic amino acids at the third transmembrane domains of Hepatitis B Surface antigen enhances its production in *Escherichia coli*." 160(2):179-184.
Shouval et al. (1994) "Improved immunogenicity in Mice of a mammalian cell-derived recombinant hepatitis B Vaccine containing pre-S1 and pre-S2 antigens as compared with conventional yeast-derived vaccines." *Vaccine* 12(15):1453-1459.
Sizemore et al., "Attenuated Shigella as a DNA Delivery Vehicle for DNA-Mediated Immunization," Science 270:299-302 (1995).
Smith et al., "In Vitro Mutagenesis," Ann. Rev. Genet. 19:423-462 (1985).
Sokolic et al. (1996) "A Bicistronic Retrovirus Vector Containing a Picornavirus InternationalRibosome Entry Site Allows for Correct of X-Linked CGD Selection for MDR1 Expression," *Blood* 87:42-50.
Soong et al. (1998) "DNA shuffling as a tool to evolve desired retrovial phenotypes." Abstracts of papers presented at the 1998 meeting of Gene Therapy, p. 228 Cold Spring Harbor Laboratory, Cold Spring Harbor, New York, Sep. 23-27,. 1998.
Soong et al. (1998) "Directed evolution of novel retroviral tropisms by DNA shuffling." Abstract #97, Programs & Abstracts. 1st Annual Meeting of the American Society of Gene Therapy, Seattle, Washington, May 28-31, 1998.
Soong et al. (1998) "Directed evolution of novel retroviral tropisms by DNA shuffling." Abstracts of papers presented at the 1998 meeting on Retroviruses, Cold Springs Harbor Laboratory, Cold Spring Harbor, New York, May 26-31, 1998.
Sosnovtsev et al. (1998) "Cleavage of the Feline Calicivirus Capsid Precurrsor Is Mediated by a Virus-Encoded Proteinase." *J. Virol* 72:3051-3059.
Srinivasan et al. (1987) "Molecular characterization of human immunodeiciency virus from Zaire." *Gene* 52:71-82.
Stemmer (1991) "A 20-Minute ethidium bromide/high-salt extraction protocol for plasmid DNA." *BioTechniques* 10(6): 726.
Stemmer (1994) *Nature* 370:389.
Stemmer (1996) "DNA sequence evolution by sexual PCR." Experientia (Basel) 52(ABSTR): A25.
Stemmer (1998) "Directed evolution of proteins, pathways, episomes and viruses by DNA shuffling," FASEB Journal 12(8): A1303.
Stemmer and Soong, (1999) "Molecular breeding of viruses for targeting and other clinical properties," Tumor Targeting 4:1-4.
Stemmer et al. (1991) "Expression of antibody Fv Fragments specific for a heavy metal chelate (indium-EDTA) in *E. Coli*." Journal of Cellular Biotechnology Supplement 0 (15 Part G):217.
Stemmer et al. (1992) "Enzymatic inverse PCR: a restriction site independent, single-fragment method for high-efficiency, site-directed mutagenesis." BioTechniques 13(2): 214, 216, 218-220.
Stemmer et al. (1993) "Increased antibody expression from *Escherichia coli* through wobble-base library mutagenesis by enzymatic inverse PCR>" Gene 123(1): 1-7.
Stemmer et al. (1993) "Selection of an active single chain Fv antibody from a protein linker library prepared by enzymatic inverse PCR>" Biotechniques 14(2): 256-265.
Stemmer et al. (1997) "Molecular evolution of genetic vaccines by DNA shuffling." FASEB Journal 11(9):A1124 17TH Intarnational Congress of Biochem . . . San Francisco, CA USA (Feb. 24 -29,).
Stemmer et al., (1995) "Single-step assembly of a gene and entire plasmid from large numbers of oligodeoxyribonucleotides," Gene 164:49-59.
Stemmer, "DNA shuffling by random fragmentation and reassembly: In vitro recombination for molecular evolution," Proc. Natl. Acad. Sci. USA 91:10747-10751 (1994).
Stemmer, W.P.C., "Rapid evolution of a protein in vitro by DNA shuffling," Nature 370:389-391 (1994).
Stemmer, W.P.C., "Searching Sequence Space," Biotechnology 13:549-553 (1995).
Stemmer, W.P.C., "Sexual PCR and Assembly PCR," The Encyclopedia of Molecular Biology, VCH Publishers, New York pp. 447-457 (1996).
Stemmer, W.P.C., "The Evolution of Molecular Computation," Science 270:1510 (1995).
Stern et al., "Purification to homogeneity and partial characterization of cytotoxic lymphocyte maturation factor from human B-lymphoblastoid cells," Proc. Acad. Sci. USA 87:6808 (1990).
Stohwasser et al., "Molecular cloning of the mouse proteasome subunits MC14 and MECL-1: reciprocally regulated tissue expression of interferon -γ-modulated proteaseome subunits," Eur. J. Immunol. 627:1182-1187(1997).
Subbarao et al. (1993) Rescue of an Influenza A Virus Wild-type PB2 Gene and a Mutant Derivative Bearing a Site-Specific Temperature-sensitive and Attenuating Mutation.*J. Virol.* 67:7223-7228.
Sugimoto et al. (1994) "Characteristics of an attenuated vaccinia virus strain, LC16m0 and It's recombinant virus vaccines." *Vaccine* 12:675-681.
Sugimoto et al. (1995) Retroviral Coexpression of a Multidrug Resistance Gene (MDR1) and Human a-Galactosidase A for Gene Therapy of Febry Disease. *Human Gene Ther* 6:905-915.
Tahara et al., "IL-12 Gene Therapy Using Direct Injection of Tumors with Genetically Engineered Autologous Fibroblasts," Human Gene Therapy 6:1607 (1995).
Tan et al., "Characterizationof Recombinant Extracellular Domain of Human Interleukin-10 Receptor," J. Biol. Chem. 270:12906 (1995).
Tang et al. (1992) "Genetic immunization is a simple method for eliciting an immune response." *Nature* 356:152.
Tang et al., "Vaccination onto bare skin," Nature 388: 729-730 (1997).
Tano et al. (1990) *Proc. Nat'l Acad Sci USA* 87:686-690.
Tartagila et al. (1992) "NYVAC: A Highly Attenuated Strain of Vaccinia Virus." *Virology* 188:217-232.
Tascon, Richard E. et al., "Vaccination against tuberculosis by DNA injection," Nat. Med. 2:888-92 (1996).
Taylor et al., "The rapid generation of oligonuleotide-directed mutations at high frequency using phosphorothioate-modified DNA," Nucl. Acids Res. 13:8765-8787 (1985).
Taylor et al., "The use of phosphorothioate-modified DNA in restriction enzyme reactions to prepare nicked DNA," Nucl. Acids Res. 13:8749-8764 (1985).

Thierfelder et al. "Requirement for Stat4 in interleukin-1-2-mediated responses of natural killer and T cells", Nature 382:171 (1996).

Todd (1974) "Development of Intranasal Vaccination for the Immunization of Cattle Against infectious Bovine Rhinotrachetis." Can. Vet J. 15:257-259.

Trudel et al., "pGATA: A Positive Selection Vector Based on the Toxicity of the Transcription Factor GATA-1 to Bacteria," Biotechniques 20:684-693 (1996).

Tytgat, G.N., "Review article: practical management issues for the Helicobacter pylori-infected patient at risk of gastric cancer," Aliment. Pharmacol. Ther. 12(1):123-8 (1998).

Ugen et al. (1994) "DNA inoculation as a novel vaccination method against retroviruses with rheumatic disease associations." Immunol. Res. 13:154-162.

Ulmer et al. (1993) "Heterologous protection against influenza by injection of DNA encoding a viral protein." Science 259:1745.

Ulmer et al. (1996) "ELI's coming: expression library immunization and vaccine antigen discovery." Trends im Microbiology 4(5):170-171.

Valle and Falgout (1998) "Mutagenesis of the NS3 Protease of Dengue Virus Type 2." J. Virol 72:624-632.

van Dinten et al. (1997) "An Infectious arterivirus cDNA clone." Proc. Nat'l Acad. Sci USA94:991-996.

VanCott et al., "Antibodies with Specificity to Native gp120 and Neutralization Activity against Primary Human Immunodeficiency Virus Type 1 Isolates Elicited by Immunization with Oligomeric gp160," J. Virol. 71:4319-4330 (1997).

Vassilev et al. (1997) "Authentic and Chimeric Full-length Genomic cDNA Clones of Bovine Viral Diarrhea Virus That Yeild Infectious Transcrips." J. Virol 71:471-487.

Velzing et al. (1999) "Induction of protective immunity against Dengue virus type 2." Vaccine 17:1312-1320.

Villinger et al., "Comparative Sequence Analysis of Cytokine Genes from Human and Nonhuman Primates," J. Immunol. 155:3946-3954 (1995).

Walther et al. (1996) "Cell type specific and inducible promoters for vectors in gene therapy as an approach for cell targeting." J. Mol. Med. 74:379-392.

Wang et al. (1993) "DNA inoculation induces cross clade anti-HIV-1 responses." Annals New York Acad. Sci 186-196.

Wang et al. (1993) "Gene inoculation generates immune responses against human deficiency virus type 1." Proc. Nat'l Acad. Sci. USA 90:4156-4160.

Walunas et al., "CTLA-4 Can Function as a Negative Regulator of T Cell Activation," Immunity 1:405 (1994).

Wells et al., "Cassette mutagenesis: an efficient method for generation of multiple mutations at defined sites," Gene 34:315-323 (1985).

Wells et al., "Importance of hydrogen-bond formation in stabilizing the transition state of subtilisin," Phil. Trans. R. Soc. Lond. A317:415-423 (1986).

Wermeille, Joel et al., "The eradication treatments of Helicobacter pylori," Pharm. World Sci. 20:1-17 (1998).

Whelan et al. (1995) "Efficient recovery of infectious vesicular stomatitis virus entirely from cDNA clones." Proc. Nat'l. Acad. Sci. USA 92:8388-8392.

Whitacre et al., "Treatment of Autoimmune Disease by Oral Tolerance to Autoantigens," Clin. Immunol. Immunopathol. 80: S31-9 (1996).

Wiertz et al., "SEC61-mediated transfer of a membrane protein from the endoplasmic reticulum to the proteasome for destruction," Nature 384: 432 (1996).

Wiertz et al., "The Human Cytomegalovirus US11 Gene Product Disclocates MHC Class 1 Heavy Chains from the Endoplasmic Reticulum to the Cytosol," Cell 84: 769-779 (1996).

Williams et al. (1993) "Genetic Infection Induces Protective In Vivo Immune Response." DNA & Cell Biology 12(8):675-683.

Williams et al. (1994) "Immunotherapeutic strategies targeting rheumatiod synovial T-cell receptors by DNA inoculation." Immunol. Res 13:145-153.

Winther et al. (1998) "Viral-Induced Rhinitis." Am J. Rhinol 12:17-20.

Wisniak et al. (1974) "Hydrogen Solubility in Joboba Oil." JAOCA 51:482-485.

Wloch et al., "The Influence of DNA Sequence on the Immunostimulatory Properties of Plasmid DNA Vectors," Hum. Gene Ther. 9:1439-1447 (1998).

Woody, Mary Alice et al., "Staphylococcal enterotoxin B mutants (N23K and F44S): biological effects and vaccine potential in a mouse model," Vaccine 15(2):133-139 (1997).

Wright et al. (1998) Humane endopoints are an objective measure of morbidity in Venezelan encephalomyelitis virus infection of mic, Arch Virol 143:1155-1162.

Xiang et al. (1994) "A Simple method to test the ability of individual viral proteins to induce immune responses." J. Virological Methods 47:103-116.

Xiang, Z. et al., "Manipulation of the Immune Response to a Plasmid-Encoded Viral Antigen by Coinoculation with Plasmids Expressing Cytokines," Immunity 2:129-135 (1995).

Yanagi et al. (1997) "Transcripts from a single full-length cDNA clone of hepatitis C virus are infectious when directly transfected into the liver of a chimpanzee." Proc Nat'l Acad. Sci. USA 94:8738-8743.

Yanagi et al. (1999) "In vivo analysis of the 3' untranslated region of the hepatitis C virus after in vitro mutagenesis of an infectious cDNA clone." Proc. Nat'l Acad. Sci USA 96:2291-2295.

Yao et al. (1998) "Generation of Mutant Infectious Bursal Disease Virus That Does Not Cause Bursal Leaions." J. Virol. 72:2647-2654.

Yu et al. (1995) "Functional cDNA Clones of the Human Respiratory Syncytial (RS) Virus . . . " J. Virol 69:2412-2419.

Zamvil, Scott S. and Lawrence Steinman, "The T Lymphocyte in Experimental Allergic Encephalomyelitis," Ann. Rev. Immunol. 8:579-621 (1990).

Zanelli et al. (1993) "Epitope mapping of human thyroid peroxidase defined seven epitopes reconized by sera from patients with thyroid pathologies." Cell. & Mol Biol. 39(5):491-501.

Zhang, J. et al., "Directed evolution of a fucosidase from a galactosidase by DNA shuffling and screening," Proc. Natl. Acad. Sci. USA 94:4504-4509 (1997).

Zhong et al. (1998) "Idenification and Characterization of an RNA-Dependent RNA Polymerase Activity within the Nonstructural Protein 5B Region of Bovine Viral Diarrhea Virus," J. Virol. 72:9365-9369.

Zhong, Weimin et al., "Therapeutic passive vaccination against chronic Lyme disease in mice," Proc. Nat'l. Acad. Sci. USA 94:12533-12538 (1997).

Zoller and Smith, "Oligonucleotide-directed mutagenesis using M13-derived vectors: an efficient and general procedure for the production of point mutations in any fragment of DNA," Nucl. Acids res. 10:6487-6500 (1982).

Zoller and Smith, "Oligonculeotide-Directed Mutagenesis: A Simple Method using Two Oligonucleotide Primers and a Single-Stranded DNA Template," Methods in Enzymol. 154:329-350 (1987).

Zoller and Smith, "Oligonucleotide-Directed Mutagenesit of DNA Fragments Cloned into M13 Vectors," Methods in Enzymol. 100:468-500 (1983).

Zou et al. (1995) "Structure-function analysis of the p35 subunit of mouse interleukin 12." J. Bio. Chem. 270(11):5864-5871.

Zuschek et al. (1961) "Immunogenicity of 2 Infectious Bovine Rhinotracheitis Vaccines," J. Am. Vet. Med. Assoc. 139"236-237.

Zygraich et al. (1974) "In Vivo and In Vitro Properties of a Temperature Sensitive Mutant of Infectious Bovine Rhinotracheitis Virus." Res. Vet. Sci. 16:328-335.

Aggarwal & Gutterman eds., Human Cytokines: Handbook for Basic and Clinical Research, vol. II (1996) (Table of Contents for vols. 1 and II).

Alcami et al., "A soluble receptor for interleukin-1 beta encoded by vaccinia virus: a novel mechanism of virus modulation of the host response to infection," Cell 71(1):153-67 (1992).

Apostolopoulos et al., "Breast cancer immunotherapy: Current status and future prospects," Immunol. and Cell. Biol. 74:457-64 (1996).

Atamas et al., "An alternative splice variant of human IL-4, IL-4 delta 2, inhibits IL-4-stimulated T cell proliferation," J. Immunol. 156(2):435-41 (1996).

Aversa et al., "SLAM and its role in T cell activation and Th cell responses." Immunol. Cell Biol. 75(2):202-5 (1997).

Bach et al., "The IFN gamma receptor: a paradigm for cytokine receptor signaling," Annu. Rev. Immunol. 15:563-91 (1997).

Baggloloni et al., "Human Cytokines: An Update," *Annu. Rev. Immunol.* 15:675-705 (1997).

Balbas et al., "Design and Construction of Expression Plasmid Vectors in *Escherichia coli*," in Methods In Enzymology: Gene Expression Technology 185:14-37 (David V. Goeddel ed., Acad. Press, Inc., 1990).

Basham et al., "Synergistic antitumor activity with IFN and monoclonal anti-idiotype for murine B cell lymphoma. Mechanism of action," *J. Immunol.* 141(8):2855-60 (1988).

Beck et al., "Analysis of Multiple Plasmodium falciparum Infections in Tanzanian Children during the Phase II Trial of Malaria Vaccine SPf66," *J. Inf. Disease* 175:921-26 (1997).

Becket et al., "Characterization of a Prostate Carcinoma Mucin-Like Antigen (PMA)," *Int. J. Cancer* 62:703-10 (1995).

Bramson et al., "Construction of a double recombinant adenovirus vector expressing a heterodimeric cytokine: in vitro and in vivo production of biologically active interleukin-12," *Hum. Gene Ther.* 7(3):333-42 (1996).

Brusselle et al., "Role of IFN-γ in the Inhibition of Allergic Airway Inflammation Caused by IL-12," *Am. J. Respir. Cell Mol. Biol.* 17:767-71 (1997).

Censini et al., "cag, a pathogenicity island of *Helicobacter pylori*, encodes type I-specific and disease-associated virulence factors," *PNAS* 93:14648-53 (1996).

Chen et al., "Discontinuous epitopes of hepatitis B surface antigen derived from a filamentous phage peptide library," *PNAS USA* 93(5):1997-2001 (1996).

Chow et al., "Improvement of Hepatitis B Virus DNA Vaccines by Plasmids Coexpressing Hepatitis B Surface Antigen and Interleukin-2," *J. Virol* 71(1):169-78 (1997).

Ciernik et al., "Induction of Cytotoxic T Lymphohocytes and Antitumor Immunity with DNA Vaccines Expressing Single T Cell Epitopes," *J. Immunol.* 156:2369-75 (1996).

Cohen et al., "Host factors in the pathogenesis of HIV disease," *Immunol. Rev.* 159:31-48 (1997).

Cortese et al., "Selection of biologically active peptides by phage display of random peptide libraries," *Curr. Opin. Biotechnol.* 7(6):616-21 (1996).

Curtis et al., "Recombinant Soluble Interleukin-11 (IL-11) Receptor alpha Chain Can Act as an IL-11 Antagonist," *Blood* 90(11):4403-12 (1997).

Cwirla et al., "Peptide Agonist of the Thrombopoietin Receptor as Potent as the Natural Cytokine," *Science* 276:1696-9 (1997).

Dagan et al., "High level expression and production of recombinant human interleukin analogs," *Protein Expr. Purif.* 3(4):290-4 (1992).

Devos et al., "Interleukin-5 and its receptor: a drug target for eosinophilia associated with chronic allergic disease," *J. Leukoc. Biol.* 57(6):813-19 (1995).

De Vries et al., "Novel fundamental approaches to intervening in IgE-mediated allergic diseases," *J. Invest. Dermatol.* 102(2):141-4 (1994).

De Vries et al., Interleukin-4 and Interleukin-13, Chap. 8, *in* Cytokine Regulation of Humoral Immunity: Basic and Clinical Aspects 195-215 (C. M. Snapper, West Sussex, UK, John Wiley and Sons, 1996).

De Vries et al., "Modulation of the human IgE response," *Eur. Respir. J. Suppl.* 22:58s-62s (1996).

De Waal Malefyt et al., "A Novel Cytokine Belonging to the IL-10 Gene Family Affects Human Monocytes and T Cells," Abstracts, 13th European Immunology Meeting, Amsterdam, Netherlands, Jun. 1997, *Immunol. Letters* 56(1):211 (May 1997).

Donnelly et al., "DNA Vaccines," *Annu. Rev. Immunol.* 15:617-48 (1997).

Dudler et al., "A Link Between Catalytic Activity, IgE-Independent Mast Cell Activation and Allergenicity of Bee Venom Phospholipase $A_2$," *J. Immunol.* 155(5):2605-13 (1995).

Eckhart et al., "Immunogenic presentation of a conserved gp41 epitope of human immunodeficiency virus type 1 on recombinant surface antigen of hepatitis B virus," *J. Gen. Virol.* 77 (9):2001-8 (1996).

Fomsgaard et al., "Improved humoral and cellular Immune response against the gp120 V3 loop of HIV-1 following genetic Immunization with a chimeric DNA vaccine encoding the V3 inserted in the hepatitis B surface antigen," *Scand. J. Immunol.* 47(4):289-95 (1998).

Foy et al., "Immune regulation by CD40 and its ligand GP39," *Annu. Rev. Immunol.* 14:591-617 (1996).

Fromm et al., "Expression of genes transferred into monocot and dicot plant cells by electroporation." *PNAS USA* 82(17):5824-28 (1985).

Gauchat et al., "Regulation of human IgE synthesis: the role of CD4+ and CD8+ T-cells and the inhibitory effects of interferon-alpha." *Eur. Respir. J. Suppl.* 13:31s-38s (1991).

Goff et al., "Laboratory Methods: Efficient Saturation Mutagenesis of a Pentapeptide Coding Sequence Using Mixed Oligonucleotides," *DNA* 6(4):381-388 (1987).

Greenfeder et al., "Insertion of a Structural Domain of Interleukin (IL)-1B Confers Agonist Activity to the IL-1 Receptor Antagonist," *J. Biol. Chem.* 270:22460-6 (1995).

Grewal et al., "The CD40-CD154 system in anti-infective host defense," *Curr. Opin. Immunol.* 9(4):491-7 (1997).

Grunig et al., "Interleukin-10 is a natural suppressor of cytokine production and inflammation in a murine model of allergic bronchopulmonary aspergillosis." *J. Exp. Med.* 185(6):1089-99 (1997).

Hannum et al., "Interleukin-1 receptor antagonist activity of a human interleukin-1 inhibitor," *Nature* 343:336-40 (1990).

Hathcock et al., "Comparative Analysis of B7-1 and B7-2 Costimulatory Ligands: Expression and Function," *J. Exptl. Med.* 180:631-40 (1994).

Herz et al., "Molecular approaches to receptors as targets for drug discovery," *J. Recept. Signal Transduct. Res.* 17(5):671-776 (1997).

Herzenberg et al. eds., Weir's Handbook of Experimental Immunology (5th ed. 1996) (index and first pages of Chaps. 220, 226, 227).

Hess et al., "Superior efficacy of secreted over somatic antigen display in recombinant *Salmonella* vaccine Induced protection against listeriosis," *PNAS* 93:1458-63 (1996).

Hill et al., "Mutagenesis with Degenerate Oligonucleotides: An Efficient Method for Saturating a Defined DNA Region with Base Pair Substitutions," *in* Methods in Enzymology: Recombinant DNA 155:558-568 (Ray Wu ed., Acad. Press, Inc., 1987).

Horuk, "Molecular properties of the chemokine receptor family," *TIPS* 15:159-165 (1994).

Horwitz et al., "Saturation Mutagenesis Using Mixed Oligonucleotides and M13 Templates Containing Uracil," *in* Methods in Enzymology: Gene Expression Technology 185:599-611 (David V. Goeddel ed., Acad. Press, Inc. 1990).

Ihle et al., "Signaling through the hematopoietic cytokine receptors," *Annu. Rev. Immunol.* 13:369-98 (1995).

Kaufman, "Vectors Used for Expression in Mammalian Cells," *in* Methods in Enzymology: Gene Expression Technology 185:487-511 (David V. Goeddel ed., Acad. Press, Inc., 1990).

Kay et al., eds., Phage Display of Peptides and Proteins: A Laboratory Manual (Acad. Press, Inc., 1996) (first page of Chap. 5).

Krieger et al., "Structures and functions of multiligand lipoprotein receptors: macrophage scavenger receptors and LDL receptor-related protein (LRP)," *Annu. Rev. Biochem.* 63:601-37 (1994).

Kroemer et al., "Immunoregulation by cytokines," *Crit. Rev. Immunol.* 13(2):163-91 (1993).

Laberge et al., "Secretion of IL-16 (Lymphocyte Chemoattractant Factor) from Serotonin-Stimulated $CD8^+$ T Cells In Vivo," *J. Immunol.* 156(1):310-5 (1996).

Le Borgne et al., "In Vivo Induction of Specific Cytotoxic T Lymphocytes in Mice and Rhesus Macaques Immunized with DNA Vector Encoding an HIV Epitope Fused with Hepatitis B Surface Antigen," *Virology* 240:304-15 (1998).

Le Grice, "Regulated Promoter for High-Level Expression of Heterologous Genes for *Bacillus subtilis*,". *in* Methods in Enzymology: Gene Expression Technology 185:201-15 (David V. Goeddel ed., Acad. Press, Inc., 1990).

Levinson, "Expression of Heterologous Genes in Mammalian Cells," *in* Methods in Enzymology: Gene Expression Technology 185:485-87 (David V. Goeddel ed., Acad. Press, Inc., 1990).

Livnah et al., "Functional Mimicry of a Protein Hormone by a Peptide Agonist: The EPO Receptor Complex at 2.8," *Science* 273:464-71 (1996).

Ma et al., "Antibody production and engineering in plants," *Ann. NY Acad. Sci.* 792:72-81 (1996).

Mattion et al., "Characterization of recombinant polioviruses expressing regions of rotavirus VP4, hepatitis B surface antigen, and herpes simplex virus type 2 glycoprotein D," *J. Virol.* 69:5132-37 (1995).

McLafferty et al., "M13 bacteriophage displaying disulfide-constrained microproteins," *Gene* 128(1):29-36 (1993).

Miele, "Plants as bioreactors for biophamaceuticals: regulatory considerations," *Trends Biotechnol.* 15(2):45-50 (1997).

Mosmann et al., "Heterogeneity of Cytokine Secretion Patterns and Functions of Helper T cell," *Adv. Immunol.* 46:111-147 (1989).

Murray et al., "Saturation mutagenesis of a major histocompatibility complex protein domain: Identification of a single conserved amino acid important for allorecognition," *PNAS USA* 85:3535-39 (1988).

Noguchi et al., "IgE responsiveness to *Dermatophagoides farinae* in young asthmatic children: IgE binding study using recombinant allergens of Der f1, Der f2 and mutant proteins of Der f2," *Int. Arch. Allergy Immunol.* 110(4):380-7 (1996).

Ostermeier et al., "A combinatorial approach to hybrid enzymes independent of DNA homology," *Nature* 19:1205-09 (1999).

Ostermeier et al., "Combinatorial protein engineering by incremental truncation," *PNAS USA* 96:3562-67 (1999).

Parronchi et al., "IL-4 and IFN (alpha and gamma) exert opposite regulatory effects on the development of cytolytic potential by Th1 or Th2 human T cell clones," *J. Immunol.* 149(9):2977-83 (1992).

Paul, *The Immune System: An Introduction*, Chap. 1, pp. 1-20 *in* Fundamental Immunology (W. E. Paul. New York, Raven Press, 1993).

Porcelli, "The CD1 family: a third lineage of antigen-presenting molecules," *Adv. Immunol.* 59:1-98 (1995).

Pumpens et al., "Hepatitis B virus core particles as epitope carriers," *Intervirology* 38(1-2):63-74 (1995).

Quaratino et al., "Similar antigenic surfaces, rather than sequence homology dictate T-cell epitope molecular mimicry," *PNAS USA* 92:10398-402 (1995).

Randhawa et al., "In vitro culture of B-lymphocytes derived from Epstein-Barr-virus-associated posttransplant lymphoproliferative disease: cytokine production and effect of interferon-alpha," *In Vitro Cell Dev. Biol. Anim.* 33(10):803-08 (1997).

Sambrook et al., Molecular Cloning: A Laboratory Manual, Cold Spring Harbor Laboratory Press, New York (2d ed. 1989), vol. 1, pp. 1.53-1.59.

Sambrook et al., Molecular Cloning: A Laboratory Manual, Cold Spring Harbor Laboratory Press, New York (2d ed. 1989), vol. II, pp. 15.51-15.113.

Schrijver et al., "Comparison of DNA application methods to reduce BRSV shedding in cattle," *Vaccine* 16(2-3):130-4 (1998).

Simmons et al., "Potent inhibition of HIV-1 infectivity in macrophages and lymphocytes by a noval CCR5 antagonist," *Science* 276:276-9 (1997).

Stern et al., Chap. 4, *Interleukin-12, in* Human Cytokines: Handbook for Basic and Clinical Research 74-96 (Aggarwal & Gutterman eds., 1996).

Tan et al., "Characterization of IL-10 Receptors on Human and Mouse Cells," *J. Biol. Chem.* 268(28):21053-59 (1993).

Thomas et al., "Potent interleukin 3 receptor agonist with selectively enhanced hematopoietic activity relative to recombinant human interleukin 3," *PNAS USA* 92:3779-83 (1995).

Tuite, "Strategies for the genetic manipulation of *Saccharomyces cerevisiae,*" *Crit. Rev. Biotechnol.* 12(1-2):157-88 (1992).

Udagawa et al., "Interleukin-18 (interferon-gamma-inducing factor) is produced by osteoblasts and acts via granulocyte/macrophage colony-stimulating factor and not via interferon-gamma to inhibit osteoclast formation," *J. Exp. Med.* 185(6):1005-12 (1997).

Ulrich et al., "Chimeric HBV core particles carrying a defined segment of Puumala hantavirus nucleocapsid protein evoke protective Immunity in an animal model," *Vaccine* 16(2-3):272-80 (1998).

Villbrandt et al., "Investigations of the thermostability and function of truncated *Thermus aquaticus* DNA polymerase fragments," *Protein Eng'g* 10(11):1281-88 (1997).

Weiner et al., "Immunostimulatory oligodeoxynucleotides containing the CpG motif are effective as immune adjuvants in tumor antigen immunization," *PNAS USA* 94:10833-7 (1997).

Yao et al., "Human IL-17: A Novel Cytokine Derived from T Cells," *J. Immunol.* 155(12):5483-86 (1995).

York et al., "Antigen processing and presentation by the class I major histocompatibility complex," *Annu. Rev. Immunol.* 14:369-96 (1996).

Yoshie et al., "Novel lymphocyte-specific CC chemokines and their receptors," *J. Leukocyte Biol.* 62(5):634-44 (1997).

Zaremba et al., "Identification of an enhancer agonist cytotoxic T lymphocyte peptide from human carcinoembryonic antigen," *Cancer Res.* 57(20):4570-77 (1997).

* cited by examiner

Figure 1: Cytotoxic T-cell Inducing Sequence Figure 2: Addition of Heterologous Epitopes to Cytotoxic T-cell Inducing Sequence

Figure 3

Figure 4: Method of preparing immunogenic agonist sequences (IAS)

WT sequence   Mutated

↓ Assembly

↓ Shuffling

Poly-epitope region containing potential agonist sequences

Figure 6: Screening of libraries of human IL-12 genes

Figure 14: Alignment of human and mouse IL-10 receptor sequences illustrating the feasibility of family shuffling when evolving IL-10 antagonists.

```
                   1                                                           60
   IL-10R_DNA-seq  AAA..GAGCTGGA......GGCGCGCAGGCCGGCTCCGCT....CCGGCCCC...GGACG
Mouse_IL-10R_seq   CCATTGTGCTGGAAAGCAGGACGCGCCGGCCGGAGGCGTAAAGGCCGGCTCCAGTGGACG 61                                                         120
   IL-10R_DNA-seq  ATGCGGC...GCGCCCAGGATGCTGCCGTGCCTCGTAGTGCTGCTGGCGGCGCTCCTCAG
Mouse_IL-10R_seq   ATGCCGCTGTGCGCCCAGGATGTTGTCGCGTTTGCTCCCATTCCTCGTCACGATCTCCAG 121                                                        180
   IL-10R_DNA-seq  CCTCCGTCTTGGCTCAGACGCTCATGGGACAGAGCTGCCCAGCCCTCCGTCTGTGTGGTT
Mouse_IL-10R_seq   CCTGAGCCTAGAATTCATTGCATACGGGACAGAACTGCCAAGCCCTTCCTATGTGTGGTT 181                                                        240
   IL-10R_DNA-seq  TGAAGCAGAATTTTTCCACCACATCCTCCACTGGACACCCATCCCAAATCAGTCTGAAAG
Mouse_IL-10R_seq   TGAAGCCAGATTTTTCCAGCACATCCTCCACTGGAAACCTATCCCAAACCAGTCTGAGAG 241                                                        300
   IL-10R_DNA-seq  TACCTGCTATGAAGTGGCGCTCCTGAGGTATGGAATAGAGTCCTGGAACTCCATCTCCAA
Mouse_IL-10R_seq   CACCTACTATGAAGTGGCCCTCAAACAGTACGGAAACTCAACCTGGAATGACATCCATAT 301                                                        360
   IL-10R_DNA-seq  CTGTAG......CCAGACCCTGTCCTATGACCTTACCGCAGTGACCTTGGACCTGTACCA
Mouse_IL-10R_seq   CTGTAGAAAGGCTCAGGCATTGTCCTGTGATCTCACAACGTTCACCCTGGATCTGTATCA 361                                                        420
   IL-10R_DNA-seq  C...AGCAATGGCTACCGGGCCAGAGTGCGGGCTGTGGACGGCAGCCGGCACTCCAACTG
Mouse_IL-10R_seq   CCGAAGCTATGGCTACCGGGCCAGAGTCCGGGCAGTGGACAACAGTCAGTACTCCAACTG 421                                                        480
   IL-10R_DNA-seq  GACCGTCACCAACACCCGCTTCTCTGTGGATGAAGTGACTCTGACAGTTGGCAGTGTGAA
Mouse_IL-10R_seq   GACCACCACTGAGACTCGCTTCACAGTGGATGAAGTGATTCTGACAGTGGATAGCGTGAC

Figure 14 (continued)

```
              481                                                           540
IL-10R_DNA-seq    CCTAGAGATCCACAATGGCTTCATCTCCTCGGGAAGATTCAGTCACTACCCAGGCCCAAGATGGC
Mouse_IL-10R_seq  TCTGAAAGCAATGGACGGCATCATCTATGGACAATCCATCCCCCCAGCCCCACGATAAC 541                                                           600
IL-10R_DNA-seq    CCCCGCGAATGACACATATGAAAGCATCTTCAGTCACTTCCGAGAGTATGAGATTGCCAT
Mouse_IL-10R_seq  CCCTGCAGGGGATGAGTACGAACAAGTCTTCAAGGATCTCCGAGTTTACAAGATTCCAT 601                                                           660
IL-10R_DNA-seq    TCGCAAGGTGCCGGGAAACTTCACGTTCACACACAAGAAAGTAAAACATGAAAAACTTCAG
Mouse_IL-10R_seq  CCGGAAGTTCTCAGAA...CTAAAGAATGCAACCAAGAGAGTGAAACAGAAACCTTCAC 661                                                           720
IL-10R_DNA-seq    CCTCCTAACCTCTGGAGAAGTGGGAGAGTTCTGTGTCCAGGTGAAACCATCTGTCGCTTC
Mouse_IL-10R_seq  CCTCACGGTCCCCATAGGGGTGAGAAAGTTTTGTGTGCAAGGTGCTGCCCCGCTGGAATC 721                                                           780
IL-10R_DNA-seq    CCGAAGTAACAAGGGGATGTGGTCTAAAGAGGAGTGCATCTCCCTCAC..CAG.GCAGTA
Mouse_IL-10R_seq  CCGAATTAACAAGGCAGAGTGGTCGGAGGAGCAGTGTTTACTTATCACGACGAGCAGTA 781                                                           840
IL-10R_DNA-seq    TTTCACCCGTGACCAACGTCATCATCTTCTTTGCCTTTGTCCTGCTGCTCTCCGGAGCCCT
Mouse_IL-10R_seq  TTTCACTGTGACCAACCTGACCAACCTGAGCATCTTAGTCATATCTATGCTGCTATTCTGTGGAATCCT 841                                                           900
IL-10R_DNA-seq    CGCCTACTGCCTGGCCTCCAGCTGTATGTGCGGCGCCGAAAGAAGCTACCCAGTGTCCT
Mouse_IL-10R_seq  GGTCT...GTCTGGTTCTCCAGTGGTACATCCGGCACCCGGGAAGTTGCCTACAGTCCT 901                                                           960
IL-10R_DNA-seq    GCTCTTCAAGAAGCCCAGCCCCTTCATCTTCATCAGCCAGCGTCCCTCCCCAGAGACCCA
Mouse_IL-10R_seq  GGTCTTCAAGAAGCCTCACGACTTCTTCCCAGCCAACC..C.TCTCTGCCCAGAAACTCC 961                                                          1020
IL-10R_DNA-seq    AGACACCATCCACCCGCTTGATGAGGAGGCCTTTTTGAAGGTGTCCCCAGAGCTGAAGAA
Mouse_IL-10R_seq  CGATGCCATTCACATCGTGACTGGACCTGGAGTTTCCCAAAGGTGTCACTAGAGCTGAGAGA
```

Figure 14 (continued)

```
                     1021                                                      1080
IL-10R_DNA-seq       CTTGGACCTGCACGGCAGCACAGACAGTGGCTTTGGCAGCACCAAGCCATCCCTGCAGAC
Mouse_IL-10R_seq     CTCAGTCCTGCATGGCAGCAGCACCGACAGTGGCTTTGGCAGTGGTAAACCATCACTTCAGAC 1081                                                      1140
IL-10R_DNA-seq       TGAAGAGCCCCAGTTCCTCCTCCCTGACCCTCACCCCCAGGCTGACAGAACGCTGGGAAA
Mouse_IL-10R_seq     TGAAGAGTCCCAATTCCTCCTCCCTGGCTCCCACCCCAGATACAGGGGACTCTGGGAAA 1141                                                      1200
IL-10R_DNA-seq       CGGGGAGCCCCCTGTGCTGGGGGACAGCTGCAGTAGTGGCAGCAGCAATAGCACAGACAG
Mouse_IL-10R_seq     AGAAGAGTCTCCAGGGCTACAGGCCACCTGTGG....GG.......ACAACACGGACAG 1201                                                      1260
IL-10R_DNA-seq       CGGGATCTGCCTGCAGGAGCCTGAGCCCCAGCCTGAGCCCCACCTGGGAGCAACA
Mouse_IL-10R_seq     TGGGATCTGCCTGCAGGAGCCTGGCTTACACTCCAGCAGTGACGTTAACCTAGTCCGAAGCAGCA 1261                                                      1320
IL-10R_DNA-seq       GGTGGGGGAGCAACAGCAGGGGCCAGGATGACAGTGGCATTGACTTAGTTCAAAACTCTGA
Mouse_IL-10R_seq     GCTTGGATATACCCATCAGGACCAGGATGACAGTGACAGTGACGTTAACCTAGTCCAGAACTCTCC 1321                                                      1380
IL-10R_DNA-seq       GGGCCCGGGCTGGGGACACAGGGTGGCTCGGCCTTGGGCCACCACAGTCCCCGGAGCC
Mouse_IL-10R_seq     AGGGCAGCCTAAGTACACACAGGATGCATCGCCTTGCCTTGGGCCATGTCTGTCTCCTAGAACC 1381                                                      1440
IL-10R_DNA-seq       TGAGGTGCCTGGGGAAGAAGACCCAGCTGCTGTGGCATTCCAGGGTTACCTGAGGCAGAC
Mouse_IL-10R_seq     TAAAGCCCCTGAGGAGAAAGACCAAGTCATGGTGACATTCCAGGCTACCAGAAACAGAC 1441                                                      1500
IL-10R_DNA-seq       CAGATGTGCTGAAGAGAAGGCAACCAAGACAGGCTGCCTGGAGGAAGAATCGCCCTTGAC
Mouse_IL-10R_seq     CAGATGAAGGCAGAGGCAGCAGCCCAGCAGAATGCTTGGACGAAGAGATTCCCTTGAC 1501                                                      1560
IL-10R_DNA-seq       AGATGGCCTTGGCCCCAAATTCGGAGATGCCTGTTGATGAGGCAGGCTTGCATCCACC
Mouse_IL-10R_seq     AGATGCCTTTGATCCTGAACTTGGGGTACACCTGCAGGATGATTGGCTTGGCCTCCACC
```

Figure 14 (continued)

```
                          1620
IL-10R_DNA-seq   1561  AGCCCTGGCCAAGGGCTATTTGAAACAGGATCCTCTAGAAATGACTCTGGCTTCCTCAGG
Mouse_IL-10R_seq        AGCTCTGGCCGCAGGTTATTTGAAACAGGAGTCTCAAGGGATGGCTTCTGCTCCACCAGG 1680
IL-10R_DNA-seq   1621  GGCCCAACGGGACAGTGGAACCAGCCCACTGAGGAATGGTCACTCCTGGCCTTGAGCAG
Mouse_IL-10R_seq        GACACCAAGTAGACAGTGGAATCAACTGACCGAAGAGTGGTCACTCCTGGGTGTGGTTAG 1740
IL-10R_DNA-seq   1681  CTGCAGTGACCTGGGAATATCTGACTGGAGCTTTGCCCATGACCTTGCCCCTCTAGGCTG
Mouse_IL-10R_seq        CTGTGAAGATCTAAGCATAGAAAGTTGGAGGTTTGCCCATAAAACTTGACCCTCTGACTG 1800
IL-10R_DNA-seq   1741  TGTGGCAGCCCCAGGTGGTCTCCTGGGCAGCTTTAACTCAGACCTGGTCACCCTGCCCCT
Mouse_IL-10R_seq        TGGGGCAGCCCCTGGTGGCCTCCTGGATAGCCTTGGCTCTAACCTGGTCACCCTGCCGTT 1860
IL-10R_DNA-seq   1801  CATCTCTAGCCTGCAGTCAAGTGAGTGACTCGGGCTGAGAGGCTGCTTTTGATTTTAGCC
Mouse_IL-10R_seq        GATCTCCAGCCTGCAGCCTAGAAGAATGACAGGCGGCTAAGAG.TTATTTGT.ATTCCAGCC 1920
IL-10R_DNA-seq   1861  ATGCCTGCTCCTCTGCCTGGACCAGGAGGGGCCTGGGGCAGAAGTTAGGCACGAGGC
Mouse_IL-10R_seq        ATGCCTGCTCCTCCCCCTCCCCTGTACCTGG..GAGG...CT....CAGGAGTCAAA...GAAAT 1980
IL-10R_DNA-seq   1921  AGTCTGGGCACTTTTCTGCAAGTCCACTGGGCTGGCCCAGCCAGGCTGCAGGGCTGGTC
Mouse_IL-10R_seq        A.TGTGGGTCCTTTTCTGCAGACCTACTGTGACCAGCT.AGCCAGGCTCCA.........

2040
IL-10R_DNA-seq   1981  AGGGTGTCTGGGGCAGGAGGCCAACTCACTGAACTAGTGCAGGGTATGTGGGTGGCA
Mouse_IL-10R_seq        .........CGGGGCAAGGAAAGGCCATCTTGATACACGAGTGTCAGGTACATGAGAGGTT 2100
IL-10R_DNA-seq   2041  CTGACCTGTTCTGTTGACTGGGCCCTGCAGACTCTGGCAGAGCTGAGAAGGG....CAG
Mouse_IL-10R_seq        GTGGC.TAGTCTGCTGCTGAGTCTGTAGATACCAGCAGAGCTGAGCAGGATTGACAG
```

Figure 14 (continued)

```
                    2101
IL-10R_DNA-seq      GGACCTTCTCCCTCCTAGGAACTCTTTCCTGTATCATAAAGGATTATTTGCTCAGGGG.A      2160
Mouse_IL-10R_seq    AGACCTCCTCATGCCTCAGGGCTGCCTCCTACACTG.GAAGGACC.TGTGTTTGGGTGTA 2161
IL-10R_DNA-seq      ACCATGGGGCTTTCTGGAGTTGTGTGTGAGGCCACCAGGCTGAAGTCAGCTCAGACCCAGA      2220
Mouse_IL-10R_seq    ACCTCAGGGCTTTCTGGA...TGTGGTAAGACTGTAGGTCTGAAGTCAGCTGAG.CCTGGA 2221
IL-10R_DNA-seq      CCTCCCTGCTTAGGCCACTCGAGCATCAGAGCTTCCAGCAGGAGGAAGGGCTGTAGGAAT      2280
Mouse_IL-10R_seq    ..TGTCTGCGGAGGT.GTTGGAGTGGCT.AGCCTGCTACAGGATAAAGGG..........

2281
IL-10R_DNA-seq      GGAAGCTTCAGGGCCTTGCTGCTGGGGTCATTTTTAGGGGAAAAAGGAGGATATGATGGT      2340
Mouse_IL-10R_seq    ..AAGGCTCAAGA....GATAGAAGGGC........AGAGCATGAGCCAGTTTAATTTT 2341
IL-10R_DNA-seq      CACATGGGGAACCTCCCCTCATCGGGCCTCTGGGCAGGAAGCTTGTCACTGAAGATCT      2400
Mouse_IL-10R_seq    GTCCTGTAGAGATGGTCCCCA...GCC...AGGATGGGTTACTTGTGGCTGTGGAGATCT 2401
IL-10R_DNA-seq      TAAGGTATATATT.TTCTGGACACTCAAACACATCATAATGGATTCACTGAGGGGAGACA      2460
Mouse_IL-10R_seq    TGGGGTATACACCACCCTGAATGATCAGCCA.GTCA......ATTCAGAGCTGTGTGGCA 2461
IL-10R_DNA-seq      AAGGGAGCCGAGACCCTGATGGGGCTTCCAGCTCAGAACCCATCCCTCTGGTG.GGTAC      2520
Mouse_IL-10R_seq    AAAGGGACTGAGACCCCAGAAT.....TTCTG............TTCCTCTTGTGAGGTGT 2521
IL-10R_DNA-seq      CTCTGGCACCCATCTGCAAATATCTCCCTCTCCAACAAATGGAGTAGCATCCCCCTGG      2580
Mouse_IL-10R_seq    CTCTGCTACCCATCTGCAGACAGACATCTTTCATCTTTTTACTATGGCTGTGTCCCC.TGA 2581
IL-10R_DNA-seq      GGCACTTGCTGAGGCCAAGCCACTCACATCCTCACTTTGCTGCCCACCATCTTGCTGAC      2640
Mouse_IL-10R_seq    ATTACCAGCAGTGGCCAAGCCATT...ACTCCC....TGCTGCTC.ACTGTTGTGACGTC
```

Figure 14 (continued)

```
                2641                                                            2700
IL-10R_DNA-seq  AACTTCCAGAGAAGCCATGGTTT..TTTGTATTGGTCATAACTCAGCCCTTTGGGCGGCCT
Mouse_IL-10R_seq AGA..CCAGACCAGACGCTGTCTGTCTGTGTTAGT....ACACTACCCTTTAGGTGGCCT 2701                                                            2760
IL-10R_DNA-seq  CTGGGCTTGGGCACCAGCTCATGCCAGCCCCAGAGGGTCAGGGTTGGAGGCCTGTGCTTG
Mouse_IL-10R_seq TTGGGCTTGAGCACTGGCCCA.............GGCTTAGGACTTATGTCTG 2761                                                            2820
IL-10R_DNA-seq  TGTTTGCTGCTAATGTCCAGCTACAGACCCAGAGAGGATAAGCCACTGGGC.ACTGGGCTGG
Mouse_IL-10R_seq CTTTTGCTGCTAATCTCTAACTGCAGACCCAGAGAACACAGGGTGCTGGGCTGACACCTCCG 2821                                                            2880
IL-10R_DNA-seq  GGTCC..CTGCCTTGTTGGTGTTCAGCTGTCTGTGATTTTGG.ACTAGC.CACTTGTCAGAG
Mouse_IL-10R_seq TGTTCAGCTGTGTGACCTCCGACCAGCAGCTTCCTCAGGGACTAAAATAATGACTAGGT 2881                                                            2940
IL-10R_DNA-seq  GGCCTCAATCTCCCATCTGTGAAATAAGGACTC...CACCTTTAGGG.GACCCTCCATGT
Mouse_IL-10R_seq CATTCAGAAGTCCCTCATGCTGAATGTTAACCAAGGTGCCCCTGGGGTGATAGTTTAGGT 2941                                                            3000
IL-10R_DNA-seq  TTGCTGGGTATTAGCCAAGCTGGTCCTGGGAGAATGCAGATACTGTCCGTGGACTACCAA
Mouse_IL-10R_seq CCTGCAACCTCTGGGTTGGAAGGA...AGTGGACTACGGAAGCCATCTGT...CCCCCTG 3001                                                            3060
IL-10R_DNA-seq  GCTGGCTTGTTTCTTATGCCAGAGGCTAACACAGATCCAATGGGAGTCCATGGTGTCATGCC
Mouse_IL-10R_seq GGGAGCTTCCACCTCATGCCAGTGTTCAGAGATCTTGTGGGAGCCTAGGGCCTTGTGCC 3061                                                            3120
IL-10R_DNA-seq  AAGACAGTATCAGACACAGCCCCAGAAGGGGGCATTATGGGCCCTGCCTCCCCATAGGCC
Mouse_IL-10R_seq AAGGGAGCTGC......TAGTCCCTGGGGTCTAGGGC.TGGTCCCTGCCTCCTATACTGC 3121                                                            3180
IL-10R_DNA-seq  ATTTGGACTCTGCCTTCAAACAAAGGCAGTT..CAGTCCACAGGCATGGAAGCTGTGAGG
Mouse_IL-10R_seq GTTTGAGACCTGTCTTCAAATGGAGGCAGTTTGCAGCCCCTAAGCAAGGATGCAAGGATGCAAGGAT
```

Figure 14 (continued)

```
                   3181
IL-10R_DNA-seq     GGACAGGCCTGTGCGTGCCATCCAGAGTCATCTCAGCCCCTGCCTTTCTCTGGAGCATTCT      3240
Mouse_IL-10R_seq   AG.CAG..CAAGGC.TGCT......GATC.CCTGAGCCCAGAGTTTCTGAAGCTTTCC 3241
IL-10R_DNA-seq     GAAAACAGATATTCTGGCCCAGGAATCCAGCAGCCATGACCCCCACCCCTCTGCCAAAGTAC    3300
Mouse_IL-10R_seq   AAATACAGACTGTGTGAGCGGGGTGAGGCCAGCCATGAACTTGGCATCCTGCCGAGAAGG 3301
IL-10R_DNA-seq     TCTTAGGTGCCAGTCTGGTAACTGAACTCCCCTCTGGAGGCAGGCTTGAGGGAGGATTCCT     3360
Mouse_IL-10R_seq   TCAT.GACCCTAATCTGGTACGAGAGCTCCTTCTGGAACTGGGC........AAGCTCTT 3361
IL-10R_DNA-seq     CAGGGTTCCCTTGAAAGCTTTATTTATTTATTTGTTCATTTATTTATTTATTGGAGAGGCAGC    3420
Mouse_IL-10R_seq   TGAGACCCCCTGGAACCTTTATTTATTTATTATT.GCTCACTTATTTATTGAGGAAGCAGC 3421
IL-10R_DNA-seq     ATTGCACAGTGAAAGAATTCTGGATATCTCAGGAGCCCCGAAATTCTAGCTCTGACTTTG     3480
Mouse_IL-10R_seq   GTGGCACAGGCGCAAGCTCTGGGTCTCTCAGGAGG.......TCTAGATTGCCTGCC 3481
IL-10R_DNA-seq     CTGTTTCCAGTGGTATGACCTTGGAGAGAAGTCACTTATCCTCTTGGAGCCTCAGTTTCCTC    3540
Mouse_IL-10R_seq   CTGTTTCTAGCTGTGTGACCTTGGGCAAGTCACGTTTCCTGAGCCTCAGTTTTCCT 3541
IL-10R_DNA-seq     ATCTGCA........GAATAATGA......CTGACTTGTCTAATTCATAGGGATGTG     3600
Mouse_IL-10R_seq   GTCTGTATGCAAAGCTTGGAAATTGAAATGTACCTGACGTGCTCCATCCCTAGGAGTGCT 3601
IL-10R_DNA-seq     AGGTTCTGCTGAGGAAATGGGTATGAATGTGCCTTGAACACAAAGCTCTGTCAATAAGTG     3660
Mouse_IL-10R_seq   GAGTCCCACTGAGAAAAGCGGGCACAGACG..CCTCAAATGGAA......CCACAAGTG
```

Figure 14 (continued)

```
                3661                                           3703
IL-10R_DNA-seq  ATACATGTTTTTTATTCCAATAAATTGTCAAG.ACCAC.....A
Mouse_IL-10R_seq GTGTGTGTTTTC.ATCCTAATAAAAGTCAGGTGTTTGTGGA
```

Figure 15: Alignment of human, rhesus monkey and rabbit DNA sequences of B7-1 molecules (CD80) illustrating the feasibility of family shuffling.

```
                          1                                                              60
B7-1,_human_seq           ATGGGCCACACACGGAGGCAGGAGGAACATCACCATCCAAGTGTCCATACCTCAATTTCTTT
B7-1,_rhesus_monkey_seq   ATGGGCCACACACGGAGGCAGGAGGAGGAGAAATATCACCATCCAAGTGTCCATACCTCAAGTTCTTT
B7-1,_rabbit_seq          ATGGGCCACACACGCTGA Figure 15 (continued)

```
                     361                                                            420
B7-1,_human_seq      TATGAAAAAGACGCTTTCAAGCGGGAACACCTGGCTGAAGTGACGTTATCAGTCAAAGCT
B7-1,_rhesus_monkey_seq TATGAAAAAGATGCTTTCAAGCGGGAACACCTGGCTGAAGTGATGTTATCCGTCAAAGCT
B7-1,_rabbit_seq     AATGAGAACGGGTCTTTCAGACGGGAGCACCTGACCTCCGTGACACTGTCCATCAGAGCT 421                                                            480
B7-1,_human_seq      GACTTCCCTACACCTAGTATATCTGACTTTGAAATTCCAACTTCTAATATTAGAAGGATA
B7-1,_rhesus_monkey_seq GACTTCCCTACACCTAGTATAACTGACTCTGAAATTCCACCTTCTAACATTAGAAGGATA
B7-1,_rabbit_seq     GACTTCCCTGTCCCTAGCATAACTGACATTGACATCCCGACCCTAATGTGAAAAGGATA 481                                                            540
B7-1,_human_seq      ATTTGCTCAACCTCTGGAGGTTTTCCAGAGCCTCACCTCTCCTGGTTGGAAAATGGAGAA
B7-1,_rhesus_monkey_seq ATTTGCTCAAACTCTGGAGGTTTTCCAGAGCCTCACCTCTCCTGGTTGGAAAATGGAGAA
B7-1,_rabbit_seq     AGATGCTCCGCCTCTGGAGGTTTTCCAGAGCCTCGCCTGGATGGAAGATGGAGAA 541                                                            600
B7-1,_human_seq      GAATTAAATGCCATCAACACAACAGTTTCCCAAGATCCTGAAACTGAGCTCTATGCTGTT
B7-1,_rhesus_monkey_seq GAATTAAATGCCATCAGCAACACAACAGTTTCCCAAGATCCTGAAACTGAGCTCTATACTGTT
B7-1,_rabbit_seq     GAACTAAACGCCGTCAACGCCGTTGACGACCAGATTTGGACACGGAGCTCTACAGCGTC 601                                                            660
B7-1,_human_seq      AGCAGCAAACTGGATTTCAATATGACAACCAACCAGAGCTTCATGTGTCTCATCAAGTAT
B7-1,_rhesus_monkey_seq AGCAGCAAACTGGATTTCAATATGACAACCAATCACAGTTTCATGTGTCTCATCAAGTAT
B7-1,_rabbit_seq     AGCAGTGAACTGGATTTCAATGTGACAACAAATAACCACAGCATCGTGTGTCTCATCAAATAC 661                                                            720
B7-1,_human_seq      GGACATTTAAGAGTGAATCAGAGACCTTCAACTGGAATACAACCAAGCAAGAGCATTTCCT
B7-1,_rhesus_monkey_seq GGACATTTAAGAGTGAATCAGAGACCTTCAACTGGAACACACCCAAGCAAGAGCATTTTCCT
B7-1,_rabbit_seq     GGGGAGCTGTCGGTGTCACAGATCTTCCCTTGGAGCAAACCAAGCAAGCAGGAGC...CTCCC 721                                                            780
B7-1,_human_seq      GATAACCTGCTCCCCATCCTGGCCATTACCTTAAT..........CTCAGTAAATGGAATT
B7-1,_rhesus_monkey_seq GATAACCTGCTCCCCATCCTGGGCCATTATCCTAAT..........CTCAGTAAATGGAATT
B7-1,_rabbit_seq     ATTGATCAGCTTCCATTCTGGGTCATTATCCCAGTAAGTGGTGCTTTGGTGCTCACTGCG
```

Figure 15 (continued)

```
                      781                                                    840
B7-1,_human_seq       TTTGTGATATGCTGCCTGACCTACTGCTTTGCCCCAAGATGCAGAGAGAGAAGGAGGAAT
B7-1,_rhesus_monkey_seq TTTGTGATATGCTGCCTGACCTACTGCTGTTTGCCCCAAGGTGCAGAGAGAGAGAAGGAAT
B7-1,_rabbit_seq      GTAGTTCTCTACTGCCTGGCCTGCAGACATGTTGCGAGGTGGAAAAGAACAAGAAGGAAT 841                                                    900
B7-1,_human_seq       GA...GAGATTGAGAAGGGAAAGTGTACGCCCCTGTATA.....................
B7-1,_rhesus_monkey_seq GA...GACATTGAGAAGGGAAAGTGTACGCCCCTGTATG.....................
B7-1,_rabbit_seq      GAAGAGACAGTGGGAACTGAAAGGCTGTCCCCTATCTACTTAGGCTCTGCGCAATCCTCG 901   906
B7-1,_human_seq       .....A
B7-1,_rhesus_monkey_seq .....A
B7-1,_rabbit_seq      GGCTGA
```

OPTIMIZATION OF IMMUNOMODULATORY PROPERTIES OF GENETIC VACCINES

CROSS-REFERENCE TO RELATED APPLICATIONS

This application is a continuation of U.S. patent application Ser. No. 09/248,716, filed Feb. 10, 1999, which claims the benefit of U.S. Provisional Application Ser. No. 60/074,294, filed Feb. 11, 1998, which applications are incorporated herein by reference for all purposes.

COPYRIGHT NOTIFICATION

Pursuant to 37 C.F.R. 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

BACKGROUND OF THE INVENTION

1. Field of the Invention

This invention pertains to the field of modulation of immune responses such as those induced by genetic vaccines.

2. Background

Antigen processing and presentation is only one factor which determines the effectiveness of vaccination, whether performed with genetic vaccines or more classical methods. Other molecules involved in determining vaccine effectiveness include cytokines (interleukins, interferons, chemokines, hematopoietic growth factors, tumor necrosis factors and transforming growth factors), which are small molecular weight proteins that regulate maturation, activation, proliferation and differentiation of the cells of the immune system. Characteristic features of cytokines are pleiotropy and redundancy; that is, one cytokine often has several functions and a given function is often mediated by more than one cytokine. In addition, several cytokines have additive or synergistic effects with other cytokines, and a number of cytokines also share receptor components.

Due to the complexity of the cytokine networks, studies on the physiological significance of a given cytokine have been difficult, although recent studies using cytokine gene-deficient mice have significantly improved our understanding on the functions of cytokines in vivo. In addition to soluble proteins, several membrane-bound costimulatory molecules play a fundamental role in the regulation of immune responses. These molecules include CD40, CD40 ligand, CD27, CD80, CD86 and CD150 (SLAM), and they are typically expressed on lymphoid cells after activation via antigen recognition or through cell-cell interactions.

T helper ($T_H$) cells, key regulators of the immune system, are capable of producing a large number of different cytokines, and based on their cytokine synthesis pattern $T_H$ cells are divided into two subsets (Paul and Seder (1994) *Cell* 76: 241-251). $T_H1$ cells produce high levels of IL-2 and IFN-$\gamma$ and no or minimal levels of IL-4, IL-5 and IL-13. In contrast, $T_H2$ cells produce high levels of IL-4, IL-5 and IL-13, and IL-2 and IFN-$\gamma$ production is minimal or absent. $T_H1$ cells activate macrophages, dendritic cells and augment the cytolytic activity of CD8$^+$ cytotoxic T lymphocytes and NK cells (Id.), whereas $T_H2$ cells provide efficient help for B cells and they also mediate allergic responses due to the capacity of $T_H2$ cells to induce IgE isotype switching and differentiation of B cells into IgE secreting cell (De Vries and Punnonen (1996) In *Cytokine regulation of humoral immunity: basic and clinical aspects*. Eds. Snapper, C. M., John Wiley & Sons, Ltd., West Sussex, UK, p. 195-215). The exact mechanisms that regulate the differentiation of T helper cells are not fully understood, but cytokines are believed to play a major role. IL-4 has been shown to direct $T_H2$ differentiation, whereas IL-12 induces development of $T_H1$ cells (Paul and Seder, supra.). In addition, it has been suggested that membrane bound costimulatory molecules, such as CD80, CD86 and CD150, can direct $T_H1$ and/or $T_H2$ development, and the same molecules that regulate $T_H$ cell differentiation also affect activation, proliferation and differentiation of B cells into Ig-secreting plasma cells (Cocks et al. (1995) *Nature* 376: 260-263; Lenschow et al. (1996) *Immunity* 5: 285-293; Punnonen et al. (1993) *Proc. Nat'l. Acad. Sci. USA*. 90: 3730-3734; Punnonen et al. (1997) *J. Exp. Med.* 185: 993-1004).

Studies in both man and mice have demonstrated that the cytokine synthesis profile of T helper ($T_H$) cells plays a crucial role in determining the outcome of several viral, bacterial and parasitic infections. High frequency of $T_H1$ cells generally protects from lethal infections, whereas dominant $T_H2$ phenotype often results in disseminated, chronic infections. For example, $T_H1$ phenotype is observed in tuberculoid (resistant) form of leprosy and $T_H2$ phenotype in lepromatous, multibacillary (susceptible) lesions (Yamamura et al. (1991) *Science* 254: 277-279). Similarly, late-stage HIV patients have $T_H2$-like cytokine synthesis profiles, and $T_H1$ phenotype has been proposed to protect from AIDS (Maggi et al. (1994) *J. Exp. Med.* 180: 489-495). Furthermore, the survival from meningococcal septicemia is genetically determined based on the capacity of peripheral blood leukocytes to produce TNF-$\alpha$ and IL-10. Individuals from families with high production of IL-10 have increased risk of fatal meningococcal disease, whereas members of families with high TNF-$\alpha$ production were more likely to survive the infection (Westendorp et al. (1997) *Lancet* 349: 170-173).

Cytokine treatments can dramatically influence $T_H1/T_H2$ cell differentiation and macrophage activation, and thereby the outcome of infectious diseases. For example, BALB/c mice infected with *Leishmania major* generally develop a disseminated fatal disease with a $T_H2$ phenotype, but when treated with anti-IL-4 mAbs or IL-12, the frequency of $T_H1$ cells in the mice increases and they are able to counteract the pathogen invasion (Chatelain et al. (1992) *J. Immunol.* 148: 1182-1187). Similarly, IFN-$\gamma$ protects mice from lethal Herpes Simplex Virus (HSV) infection, and MCP-1 prevents lethal infections by *Pseudomonas aeruginosa* or *Salmonella typhimurium*. In addition, cytokine treatments, such as recombinant IL-2, have shown beneficial effects in human common variable immunodeficiency (Cunningham-Rundles et al. (1994) *N. Engl. J. Med.* 331: 918-921).

The administration of cytokines and other molecules to modulate immune responses in a manner most appropriate for treating a particular disease can provide a significant tool for the treatment of disease. However, presently available immunomodulator treatments can have several disadvantages, such as insufficient specific activity, induction of immune responses against, the immunomodulator that is administered, and other potential problems. Thus, a need exists for immunomodulators that exhibit improved properties relative to those currently available. The present invention fulfills this and other needs.

SUMMARY OF THE INVENTION

The present invention provides methods of obtaining a polynucleotide that has a modulatory effect on an immune response that is induced by a genetic vaccine, either directly (i.e., as an immunomodulatory polynucleotide) or indirectly (i.e., upon translation of the polynucleotide to create an immunomodulatory polypeptide.) The methods of the invention involve: creating a library of recombinant polynucleotides; and screening the library to identify at least one optimized recombinant polynucleotide that exhibits, either by itself or through the encoded polypeptide, an enhanced ability to modulate an immune response than a form of the nucleic acid from which the library was created. Examples include, for example, CpG-rich polynucleotide sequences, polynucleotide sequences that encode a costimulator (e.g., B7-1, B7-2, CD1, CD40, CD154 (ligand for CD40), CD150 (SLAM), or a cytokine. The screening step used in these methods can include, for example, introducing genetic vaccine vectors which comprise the library of recombinant nucleic acids into a cell, and identifying cells which exhibit an increased ability to modulate an immune response of interest or increased ability to express an immunomodulatory molecule. For example, a library of recombinant cytokine-encoding nucleic acids can be screened by testing the ability of cytokines encoded by the nucleic acids to activate cells which contain a receptor for the cytokine. The receptor for the cytokine can be native to the cell, or can be expressed from a heterologous nucleic acid that encodes the cytokine receptor. For example, the optimized costimulators can be tested to identify those for which the cells or culture medium are capable of inducing a predominantly $T_H2$ immune response, or a predominantly $T_H1$ immune response.

In some embodiments, the polynucleotide that has a modulatory effect on an immune response is obtained by: (1) recombining at least first and second forms of a nucleic acid that is, or encodes a molecule that is, involved in modulating an immune response, wherein the first and second forms differ from each other in two or more nucleotides, to produce a library of recombinant polynucleotides; and (2) screening the library to identify at least one optimized recombinant polynucleotide that exhibits, either by itself or through the encoded polypeptide, an enhanced ability to modulate an immune response than a form of the nucleic acid from which the library was created. If additional optimization is desired, the method can further involve: (3) recombining at least one optimized recombinant polynucleotide with a further form of the nucleic acid, which is the same or different from the first and second forms, to produce a further library of recombinant polynucleotides; (4) screening the further library to identify at least one further optimized recombinant polynucleotide that exhibits an enhanced ability to modulate an immune response than a form of the nucleic acid from which the library was created.; and (5) repeating (3) and (4), as necessary, until the further optimized recombinant polynucleotide exhibits an further enhanced ability to modulate an immune response than a form of the nucleic acid from which the library was created.

In some embodiments of the invention, the library of recombinant polynucleotides is screened by: expressing the recombinant polynucleotides so that the encoded peptides or polypeptides are produced as fusions with a protein displayed on the surface of a replicable genetic package; contacting the replicable genetic packages with a plurality of cells that display the receptor; and identifying cells that exhibit a modulation of an immune response mediated by the receptor.

The invention also provides methods for obtaining a polynucleotide that encodes an accessory molecule that improves the transport or presentation of antigens by a cell. These methods involve creating a library of recombinant polynucleotides by subjecting to recombination nucleic acids that encode all or part of the accessory molecule; and screening the library to identify an optimized recombinant polynucleotide that encodes a recombinant accessory molecule that confers upon a cell an increased or decreased ability to transport or present an antigen on a surface of the cell compared to an accessory molecule encoded by the non-recombinant nucleic acids. In some embodiments, the screening step involves: introducing the library of recombinant polynucleotides into a genetic vaccine vector that encodes an antigen to form a library of vectors; introducing the library of vectors into mammalian cells; and identifying mammalian cells that exhibit increased or decreased immunogenicity to the antigen.

In some embodiments of the invention, the cytokine that is optimized is interleukin-12 and the screening is performed by growing mammalian cells which contain the genetic vaccine vector in a culture medium, and detecting whether T cell proliferation or T cell differentiation is induced by contact with the culture medium. In another embodiment, the cytokine is interferon-α and the screening is performed by expressing the recombinant vector module as a fusion protein which is displayed on the surface of a bacteriophage to form a phage display library, and identifying phage library members which are capable of inhibiting proliferation of a B cell line. Another embodiment utilizes B7-1 (CD80) or B7-2 (CD86) as the costimulator and the cell or culture medium is tested for ability to modulate an immune response.

The invention provides methods of using DNA shuffling to obtain optimized recombinant vector modules that encode cytokines and other costimulators that exhibit reduced immunogenicity compared to a corresponding polypeptide encoded by a non-optimized vector module. The reduced immunogenicity can be detected by introducing a cytokine or costimulator encoded by the recombinant vector module into a mammal and determining whether an immune response is induced against the cytokine.

The invention also provides methods of obtaining optimized immunomodulatory sequences that encode a cytokine antagonist. For example, suitable cytokine agonists include a soluble cytokine receptor and a transmembrane cytokine receptor having a defective signal sequence. Examples include ΔIL-10R and ΔIL-4R, and the like.

BRIEF DESCRIPTION OF THE DRAWINGS

FIG. 1 shows an example of a cytotoxic T-cell inducing sequence (CTIS) obtained from HBsAg polypeptide (PreS2 plus S regions).

FIG. 2 shows a CTIS having heterologous epitopes attached to the cytoplasmic portion.

FIG. 3 shows the derivation of immunogenic agonistic sequences (IAS) as described in Example 3. Specific killing (percent) is shown for an effector: target (E:T) ratio of five.

FIG. 4 shows a method for preparing immunogenic agonist sequences (IAS). Wild-type (WT) and mutated forms of nucleic acids encoding a polypeptide of interest are assembled and subjected to DNA shuffling to obtain a nucleic acid encoding a poly-epitope region that contains potential agonist sequences.

Figure 5:
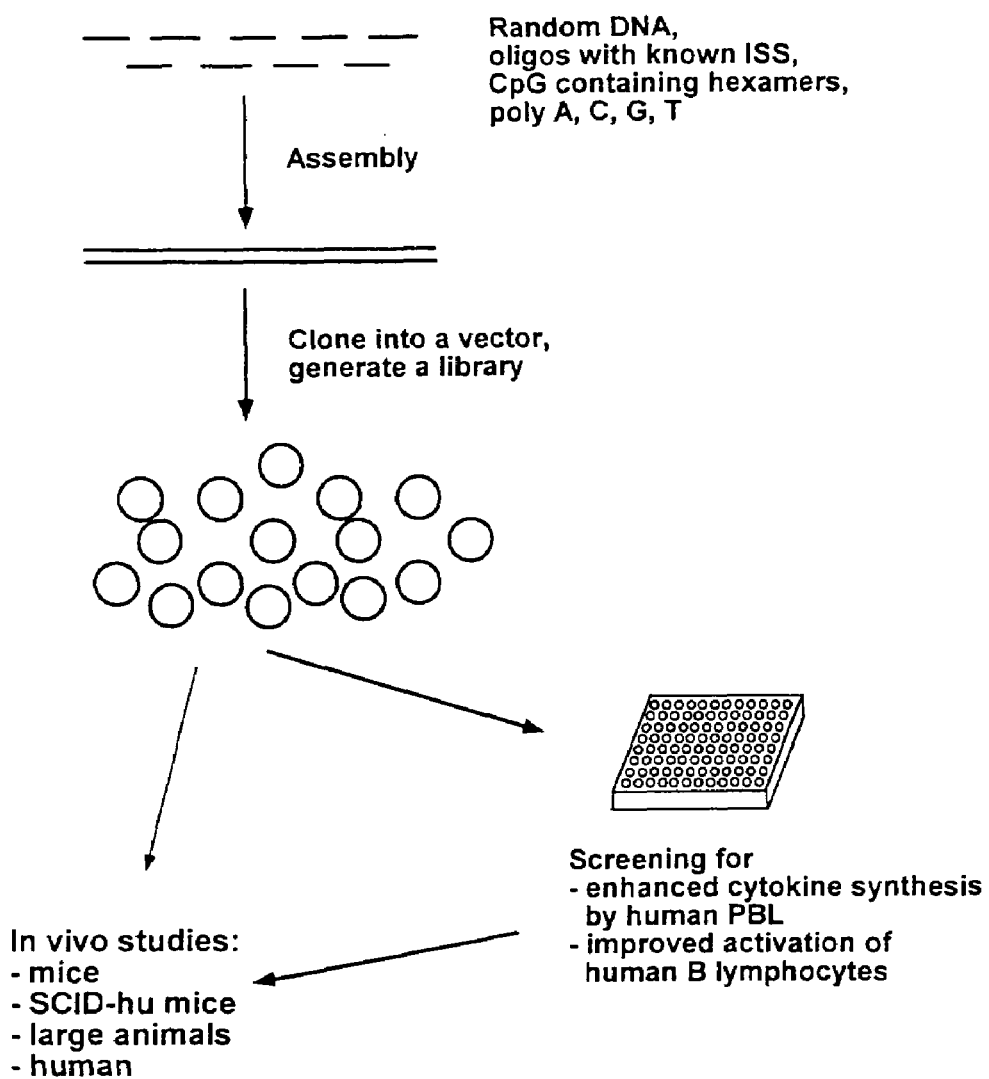
FIG. 5 shows a scheme for improving immunostimulatory sequences by DNA shuffling.
Figure 6:
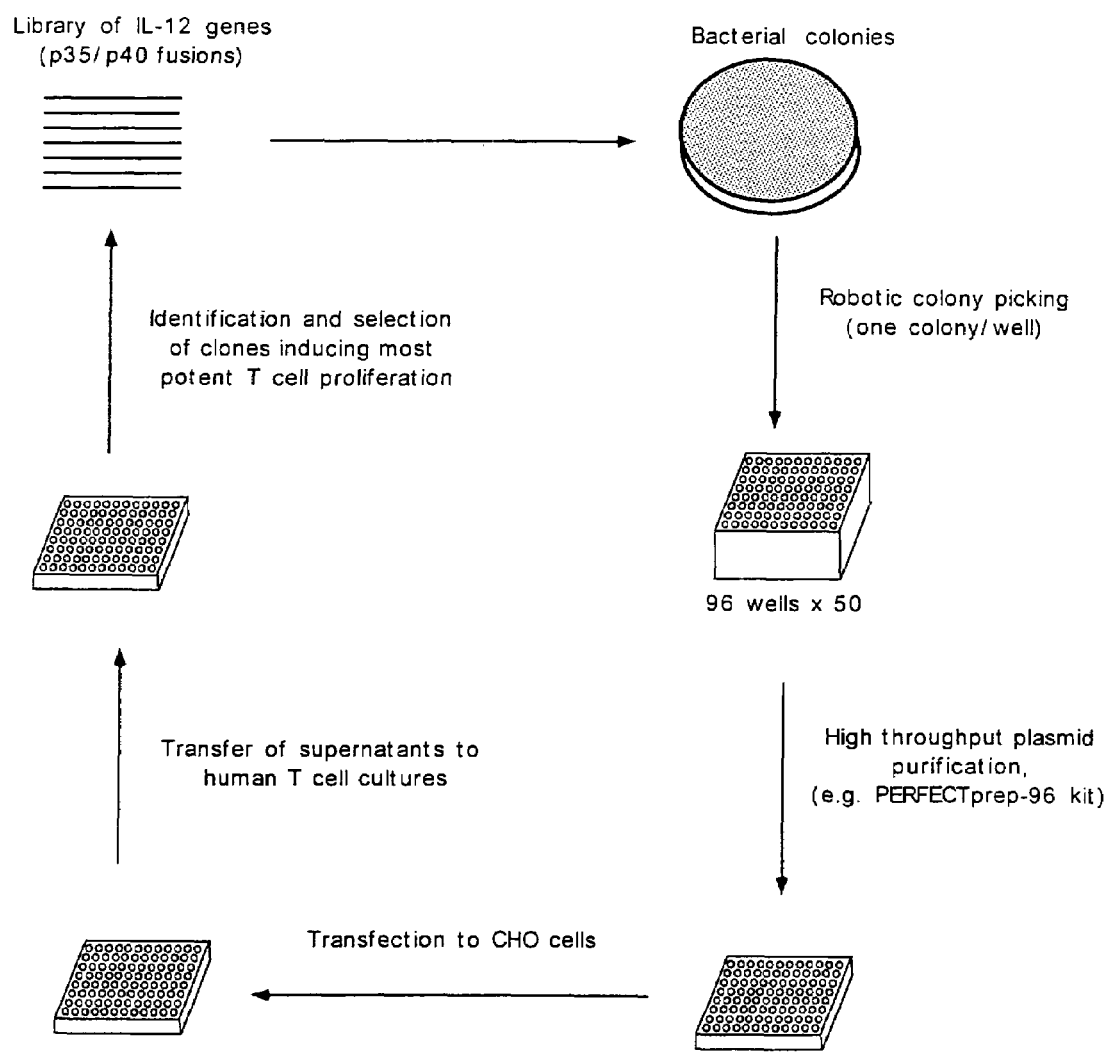
FIG. 6 is a diagram of a procedure by which recombinant libraries of human IL-12 genes can be screened to identify shuffled IL-12 genes that encode recombinant IL-12 having increased ability to induce T cell proliferation.

FIG. 7 shows the results of a high-throughput functional assay for vectors that encode variants of IL-12 obtained using the methods of the invention.

FIG. 8 shows the induction of T cell proliferation upon transfection of the T cells by individual vectors that encode IL-12 variants.

FIG. 9 shows results of an experiment which demonstrates that a shuffled IL-12 chimera obtained using the methods of the invention exhibits improved ability to activate human T cells.

FIG. 10 shows a model of how T cell activation or anergy can be induced by genetic vaccine vectors that encode different B7-1 (CD80) and/or B7-2 (CD86) variants.

FIG. 11 shows a method for using DNA shuffling to obtain CD80/CD86 variants that have improved capacity to induce T cell activation or anergy.

FIG. 12 shows results obtained in a screening assay for altered function of B7.

FIG. 13 provides experimental results which demonstrate that shuffled B7 chimeras provide potent T cell activation.

FIG. 14 presents an alignment of the nucleotide sequences for human (SEQ ID NO:1) and mouse (SEQ ID NO:2) IL-10 receptor sequences.

FIG. 15 shows an alignment of the nucleotide sequences of B7-1 (CD80) genes from human (SEQ ID NO: 3) rhesus monkey (SEQ ID NO:4) and rabbit (SEQ ID NO:5).

DETAILED DESCRIPTION

Definitions

The term "cytokine" includes, for example, interleukins, interferons, chemokines, hematopoietic growth factors, tumor necrosis factors and transforming growth factors. In general these are small molecular weight proteins that regulate maturation, activation, proliferation and differentiation of the cells of the immune system.

The term "screening" describes, in general, a process that identifies optimal immunomodulatory molecules. Several properties of the respective molecules can be used in selection and screening including, for example, ability to induce a desired immune response in a test system. Selection is a form of screening in which identification and physical separation are achieved simultaneously by expression of a selection marker, which, in some genetic circumstances, allows cells expressing the marker to survive while other cells die (or vice versa). Screening markers include, for example, luciferase, beta-galactosidase and green fluorescent protein. Selection markers include drug and toxin resistance genes, and the like. Because of limitations in studying primary immune responses in vitro, in vivo studies are particularly useful screening methods. In these studies, the genetic vaccines that include immunomodulatory molecules are first introduced to test animals, and the immune responses are subsequently studied by analyzing protective immune responses or by studying the quality or strength of the induced immune response using lymphoid cells derived from the immunized animal. Although spontaneous selection can and does occur in the course of natural evolution, in the present methods selection is performed by man.

A "exogenous DNA segment", "heterologous sequence" or a "heterologous nucleic acid", as used herein, is one that originates from a source foreign to the particular host cell, or, if from the same source, is modified from its original form. Thus, a heterologous gene in a host cell includes a gene that is endogenous to the particular host cell, but has been modified. Modification of a heterologous sequence in the applications described herein typically occurs through the use of DNA shuffling. Thus, the terms refer to a DNA segment which is foreign or heterologous to the cell, or homologous to the cell but in a position within the host cell nucleic acid in which the element is not ordinarily found. Exogenous DNA segments are expressed to yield exogenous polypeptides.

The term "gene" is used broadly to refer to any segment of DNA associated with a biological function. Thus, genes include coding sequences and/or the regulatory sequences required for their expression. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

The term "isolated", when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest. The term "purified" denotes that a nucleic acid or protein gives rise to essentially one band in an electrophoretic gel. Particularly, it means that the nucleic acid or protein is at least about 50% pure, more preferably at least about 85% pure, and most preferably at least about 99% pure.

The term "naturally-occurring" is used to describe an object that can be found in nature as distinct from being artificially produced by man. For example, a polypeptide or polynucleotide sequence that is present in an organism (including viruses, bacteria, protozoa, insects, plants or mammalian tissue) that can be isolated from a source in nature and which has not been intentionally modified by man in the laboratory is naturally-occurring.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) *Nucleic Acid Res.* 19: 5081; Ohtsuka et al. (1985) *J. Biol. Chem.* 260: 2605-2608; Cassol et al. (1992); Rossolini et al. (1994) *Mol. Cell. Probes* 8: 91-98). The term nucleic acid is used interchangeably with gene, cDNA, and mRNA encoded by a gene.

"Nucleic acid derived from a gene" refers to a nucleic acid for whose synthesis the gene, or a subsequence thereof, has ultimately served as a template. Thus, an mRNA, a cDNA reverse transcribed from an mRNA, an RNA transcribed from that cDNA, a DNA amplified from the cDNA, an RNA transcribed from the amplified DNA, etc., are all derived from the gene and detection of such derived products is indicative of the presence and/or abundance of the original gene and/or gene transcript in a sample.
Figure 7:
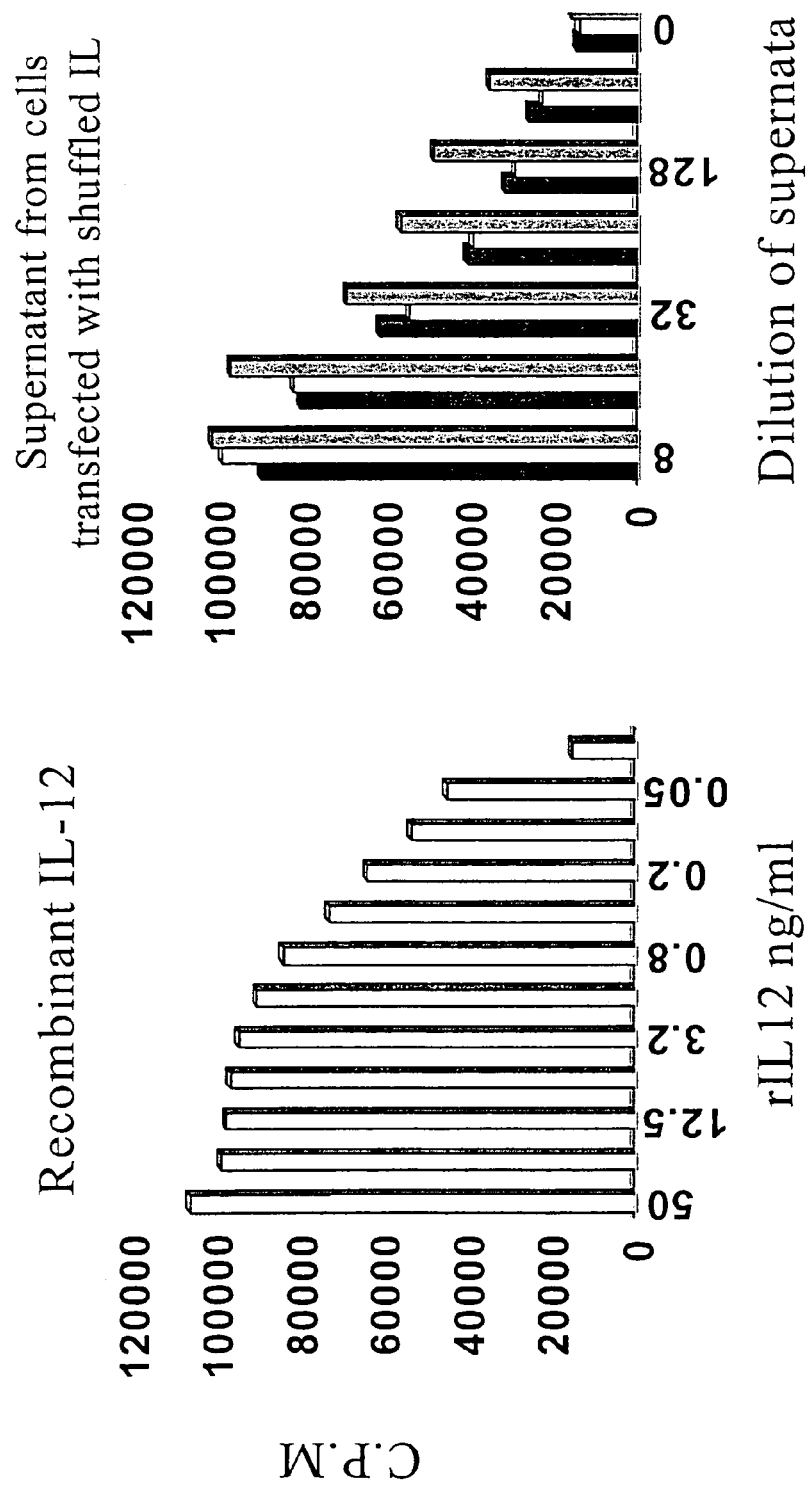
Figure 8:
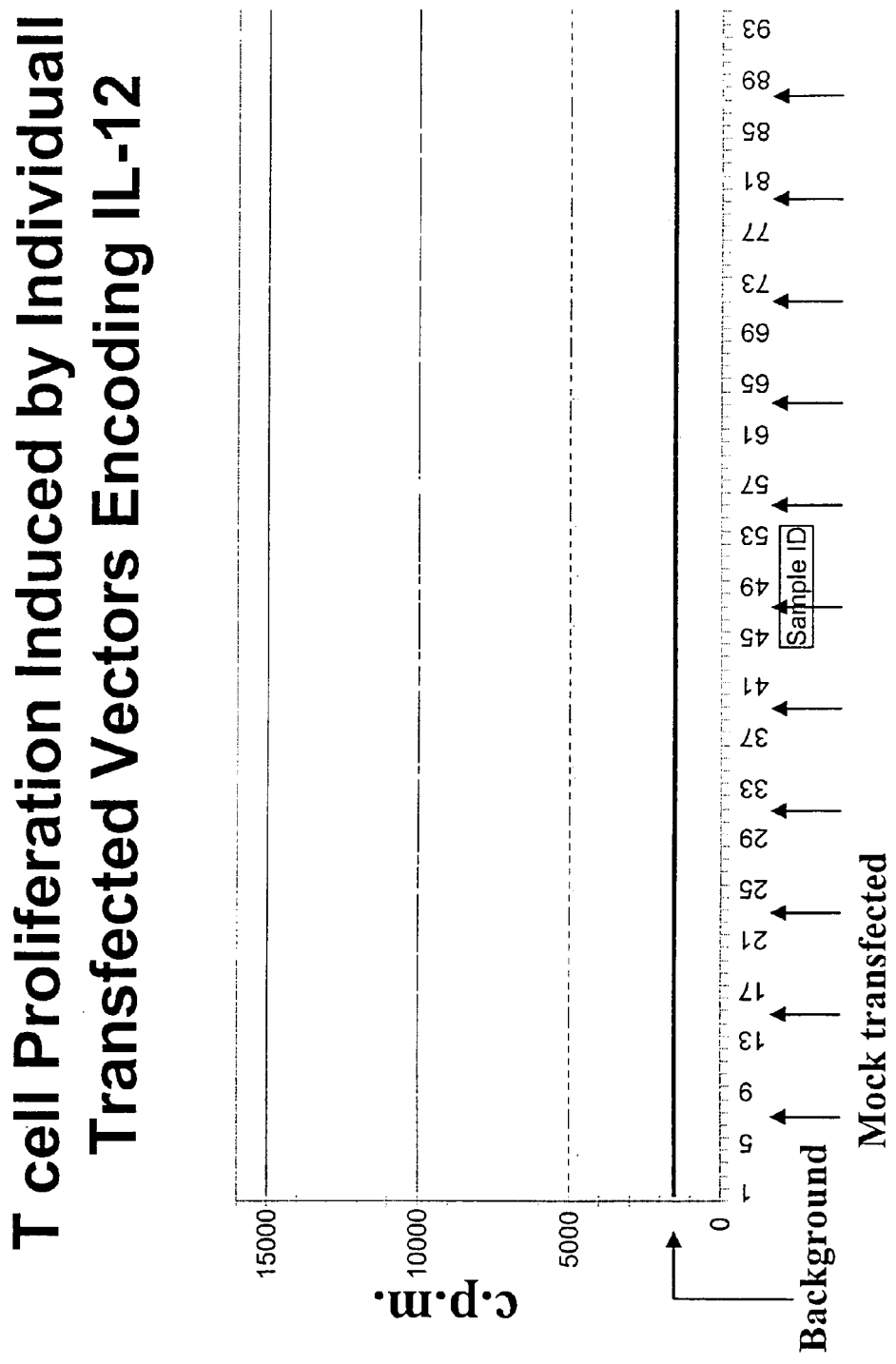
Figure 9:
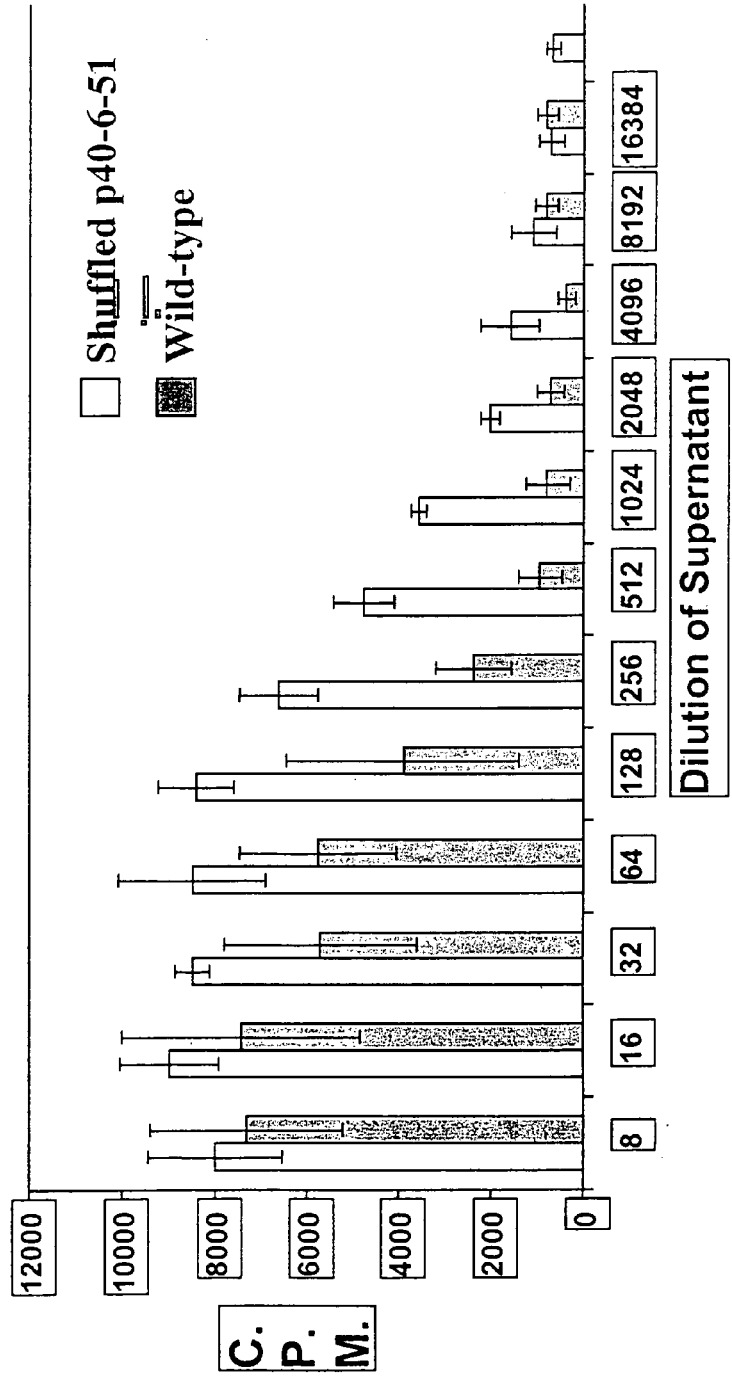

A nucleic acid is "operably linked" when it is placed into a functional relationship with another nucleic acid sequence. For instance, a promoter or enhancer is operably linked to a coding sequence if it increases the transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

A specific binding affinity between two molecules, for example, a ligand and a receptor, means a preferential binding of one molecule for another in a mixture of molecules. The binding of the molecules can be considered specific if the binding affinity is about $1\times10^4 M^{-1}$ to about $1\times10^6 M^{-1}$ or greater.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "recombinant expression cassette" or simply an "expression cassette" is a nucleic acid construct, generated recombinantly or synthetically, with nucleic acid elements that are capable of effecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

A "recombinant polynucleotide" or a "recombinant polypeptide" is a non-naturally occurring polynucleotide or polypeptide that includes nucleic acid or amino acid sequences, respectively, from more than one source nucleic acid or polypeptide, which source nucleic acid or polypeptide can be a naturally occurring nucleic acid or polypeptide, or can itself have been subjected to mutagenesis or other type of modification. The source polynucleotides or polypeptides from which the different nucleic acid or amino acid sequences are derived are sometimes homologous (i.e., have, or encode a polypeptide that has, the same or a similar structure and/or function), and are often from different isolates, serotypes, strains, species, of organism or from different disease states, for example.

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80%, most preferably 90-95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In some embodiments, the sequences are substantially identical over the entire length of the coding regions.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat.'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information and its website. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul (1993) *Proc. Nat'l Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Another indication that two nucleic acid sequences are substantially identical is that the two molecules hybridize to each other under stringent conditions. The phrase "hybridizing specifically to", refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

"Stringent hybridization conditions" and "stringent hybridization wash conditions" in the context of nucleic acid hybridization experiments such as Southern and northern hybridizations are sequence dependent, and are different under different environmental parameters. Longer sequences hybridize specifically at higher temperatures. An extensive guide to the hybridization of nucleic acids is found in Tijssen (1993) *Laboratory Techniques in Biochemistry and Molecular Biology—Hybridization with Nucleic Acid Probes* part I chapter 2 "Overview of principles of hybridization and the strategy of nucleic acid probe assays", Elsevier, N.Y. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15M NaCl at 72° C. for about 15 minutes. An example of stringent wash conditions is a 0.2×SSC wash at 65° C. for 15 minutes (see, Sambrook, infra., for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M $Na^+$ ion, typically about 0.01 to 1.0 M $Na^+$ ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

A further indication that two nucleic acid sequences or polypeptides are substantially identical is that the polypeptide encoded by the first nucleic acid is immunologically cross reactive with, or specifically binds to, the polypeptide encoded by the second nucleic acid. Thus, a polypeptide is typically substantially identical to a second polypeptide, for example, where the two peptides differ only by conservative substitutions.

The phrase "specifically (or selectively) binds to an antibody" or "specifically (or selectively) immunoreactive with", when referring to a protein or peptide, refers to a binding reaction which is determinative of the presence of the protein, or an epitope from the protein, in the presence of a heterogeneous population of proteins and other biologics. Thus, under designated immunoassay conditions, the specified antibodies bind to a particular protein and do not bind in a significant amount to other proteins present in the sample. The antibodies raised against a multivalent antigenic polypeptide will generally bind to the proteins from which one or more of the epitopes were obtained. Specific binding to an antibody under such conditions may require an antibody that is selected for its specificity for a particular protein. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See Harlow and Lane (1988) *Antibodies, A Laboratory Manual*, Cold Spring Harbor Publications, New York "Harlow and Lane"), for a description of immunoassay formats and conditions that can be used to determine specific immunoreactivity. Typically a specific or selective reaction will be at least twice background signal or noise and more typically more than 10 to 100 times background.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every polynucleotide sequence described herein which encodes a polypeptide also describes every possible silent variation, except where otherwise noted. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence.

Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. The following five groups each contain amino acids that are conservative substitutions for one another:

Aliphatic: Glycine (G), Alanine (A), Valine (V), Leucine (L), Isoleucine (I);

Aromatic: Phenylalanine (F), Tyrosine (Y), Tryptophan (W);

Sulfur-containing: Methionine (M), Cysteine (C);

Basic: Arginine (R), Lysine (K), Histidine (H);

Acidic: Aspartic acid (D), Glutamic acid (E), Asparagine (N), Glutamine (Q). See also, Creighton (1984) *Proteins*, W.H. Freeman and Company, for additional groupings of amino acids. In addition, individual substitutions, deletions or additions which alter, add or delete a single amino acid or a small percentage of amino acids in an encoded sequence are also "conservatively modified variations".

A "subsequence" refers to a sequence of nucleic acids or amino acids that comprises a part of a longer sequence of nucleic acids or amino acids (e.g., polypeptide) respectively.

DESCRIPTION OF THE PREFERRED EMBODIMENTS

The present invention provides methods for obtaining polynucleotide sequences that, either directly or indirectly (i.e., through encoding a polypeptide), can modulate an immune response when present on a genetic vaccine vector. In another embodiment, the invention provides methods for optimizing the transport and presentation of antigens. The optimized immunomodulatory polynucleotides obtained using the methods of the invention are particularly suited for use in conjunction with vaccines, including genetic vaccines. One of the advantages of genetic vaccines is that one can incorporate genes encoding immunomodulatory molecules, such as cytokines, costimulatory molecules, and molecules that improve antigen transport and presentation into the genetic vaccine vectors. This provides opportunities to modulate immune responses that are induced against the antigens expressed by the genetic vaccines.

A. Creation of Recombinant Libraries

The invention involves creating recombinant libraries of polynucleotides that are then screened to identify those library members that exhibit a desired property. The recombinant libraries can be created using any of various methods.

The substrate nucleic acids used for the recombination can vary depending upon the particular application. For example, where a polynucleotide that encodes a cytokine, chemokine, or other accessory molecule is to be optimized, different forms of nucleic acids that encode all or part of the cytokine, chemokine, or other accessory molecule are subjected to recombination. The methods require at least two variant forms of a starting substrate. The variant forms of candidate substrates can show substantial sequence or secondary structural similarity with each other, but they should also differ in at least two positions. The initial diversity between forms can be the result of natural variation, e.g., the different variant forms (homologs) are obtained from different individuals or strains of an organism (including geographic variants) or constitute related sequences from the same organism (e.g., allelic variations). Alternatively, the initial diversity can be induced, e.g., the second variant form can be generated by error-prone transcription, such as an error-prone PCR or use of a polymerase which lacks proof-reading activity (see Liao (1990) *Gene* 88:107-111), of the first variant form, or, by replication of the first form in a mutator strain (mutator host cells are discussed in further detail below). The initial diversity between substrates is greatly augmented in subsequent steps of recursive sequence recombination.

Often, improvements are achieved after one round of recombination and selection. However, recursive sequence recombination can be employed to achieve still further improvements in a desired property. Sequence recombination can be achieved in many different formats and permutations of formats, as described in further detail below. These formats share some common principles. Recursive sequence recombination entails successive cycles of recombination to generate molecular diversity. That is, one creates a family of nucleic acid molecules showing some sequence identity to each other but differing in the presence of mutations. In any given cycle, recombination can occur in vivo or in vitro, intracellular or extracellular. Furthermore, diversity resulting from recombination can be augmented in any cycle by applying prior methods of mutagenesis (e.g., error-prone PCR or cassette mutagenesis) to either the substrates or products for recombination. In some instances, a new or improved property or characteristic can be achieved after only a single cycle of in vivo or in vitro recombination, as when using different, variant forms of the sequence, as homologs from different individuals or strains of an organism, or related sequences from the same organism, as allelic variations.

In a presently preferred embodiment, the recombinant libraries are prepared using DNA shuffling. The shuffling and screening or selection can be used to "evolve" individual genes, whole plasmids or viruses, multigene clusters, or even whole genomes (Stemmer (1995) *Bio/Technology* 13:549-553). Reiterative cycles of recombination and screening/selection can be performed to further evolve the nucleic acids of interest. Such techniques do not require the extensive analysis and computation required by conventional methods for polypeptide engineering. Shuffling allows the recombination of large numbers of mutations in a minimum number of selection cycles, in contrast to traditional, pairwise recombination events. Thus, the sequence recombination techniques described herein provide particular advantages in that they provide recombination between mutations in any or all of these, thereby providing a very fast way of exploring the manner in which different combinations of mutations can affect a desired result. In some instances, however, structural and/or functional information is available which, although not required for sequence recombination, provides opportunities for modification of the technique.

Exemplary formats and examples for sequence recombination, sometimes referred to as DNA shuffling, evolution, or molecular breeding, have been described by the present inventors and co-workers in co-pending applications U.S. patent application Ser. No. 08/198,431, filed Feb. 17, 1994, now U.S. Pat. No. 5,605,793; Serial No. PCT/US95/02126, filed Feb. 17, 1995; Ser. No. 08/425,684, filed Apr. 18, 1995, now U.S. Pat. No. 5,834,252: Serial No. 08/537,874, filed Oct. 30, 1995, now U.S. Pat. No. 5,830,721; Ser. No. 08/564,955, filed Nov. 30, 1995, now U.S. Pat. No. 5,811,238: Ser. No. 08/621,859, filed Mar. 25, 1996, now U.S. Pat. No. 6,117,679: Ser. No. 08/621,430, filed Mar. 25, 1996, now abandoned: Serial No. PCT/US96/05480, filed Apr. 18, 1996; Ser. No. 08/650,400, filed May 20, 1996, now U.S. Pat. No. 5,837,458: Ser. No. 08/675,502, filed Jul. 3, 1996, now U.S. Pat. No. 5.928,905; Ser. No. 08/721,824, filed Sep. 27, 1996, which was converted to provisional U.S. App. Ser. No. 60/037,742, now abandoned; Serial No. PCT/US97/17300, filed Sep. 26, 1997; and Serial No. PCT/US97/24239, filed Dec. 17, 1997; Stemmer, Science 270:1510 (1995); Stemmer et al., Gene 164:49-53 (1995); Stemmer, Bio/Technology 13:549-553 (1995); Stemmer, Proc. Natl. Acad. Sci. U.S.A. 91:10747-10751 (1994); Stemmer, Nature 370:389-391 (1994); Crameri et al., Nature Medicine 2(1):1-3 (1996); Crameri et al., Nature Biotechnology 14:315-319 (1996), each of which is incorporated by reference in its entirety for all purposes.

Other methods for obtaining recombinant polynucleotides and/or for obtaining diversity in nucleic acids used as the substrates for shuffling include, for example, homologous recombination (PCT/US98/05223; Publ. No. WO98/42727); oligonucleotide-directed mutagenesis (for review see, Smith, *Ann. Rev. Genet.* 19: 423-462 (1985); Botstein and Shortle, *Science* 229: 1193-1201 (1985); Carter, *Biochem. J.* 237: 1-7 (1986); Kunkel, "The efficiency of oligonucleotide directed mutagenesis" in *Nucleic acids & Molecular Biology*, Eckstein and Lilley, eds., Springer Verlag, Berlin (1987)). Included among these methods are oligonucleotide-directed mutagenesis (Zoller and Smith, *Nucl. Acids Res.* 10: 6487-6500 (1982), *Methods in Enzymol.* 100: 468-500 (1983), and *Methods in Enzymol.* 154: 329-350 (1987)) phosphothioate-modified DNA mutagenesis (Taylor et al., *Nucl. Acids Res.* 13: 8749-8764 (1985); Taylor et al., *Nucl. Acids Res.* 13: 8765-8787 (1985); Nakamaye and Eckstein, *Nucl. Acids Res.* 14: 9679-9698 (1986); Sayers et al., *Nucl. Acids Res.* 16: 791-802 (1988); Sayers et al., *Nucl. Acids Res.* 16: 803-814 (1988)), mutagenesis using uracil-containing templates (Kunkel, *Proc. Nat'l. Acad. Sci. USA* 82: 488-492 (1985) and Kunkel et al., *Methods in Enzymol.* 154: 367-382)); mutagenesis using gapped duplex DNA (Kramer et al., *Nucl. Acids Res.* 12: 9441-9456 (1984); Kramer and Fritz, *Methods in Enzymol.* 154: 350-367 (1987); Kramer et al., *Nucl. Acids Res.* 16: 7207 (1988)); and Fritz et al., *Nucl. Acids Res.* 16: 6987-6999 (1988)). Additional suitable methods include point mismatch repair (Kramer et al., *Cell* 38: 879-887 (1984)), mutagenesis using repair-deficient host strains (Carter et al., *Nucl. Acids Res.* 13: 4431-4443 (1985); Carter, *Methods in Enzymol.* 154: 382-403 (1987)), deletion mutagenesis (Eghtedarzadeh and Henikoff, *Nucl. Acids Res.* 14: 5115 (1986)), restriction-selection and restriction-purification (Wells et al., *Phil. Trans. R. Soc. Lond. A* 317: 415-423 (1986)), mutagenesis by total gene synthesis (Nambiar et al, *Science* 223: 1299-1301 (1984); Sakamar and Khorana, *Nucl. Acids Res.* 14: 6361-6372 (1988); Wells et al., *Gene* 34: 315-323 (1985); and Grundström et al., *Nucl. Acids Res.* 13: 3305-3316 (1985). Kits for mutagenesis are commercially available (e.g., Bio-Rad, Amersham International, Anglian Biotechnology).

B. Screening Methods

A recombination cycle is usually followed by at least one cycle of screening or selection for molecules having a desired property or characteristic. If a recombination cycle is performed in vitro, the products of recombination, i.e., recombinant segments, are sometimes introduced into cells before the screening step. Recombinant segments can also be linked to an appropriate vector or other regulatory sequences before screening. Alternatively, products of recombination generated in vitro are sometimes packaged as viruses before screening. If recombination is performed in vivo, recombination products can sometimes be screened in the cells in which recombination occurred. In other applications, recombinant segments are extracted from the cells, and optionally packaged as viruses, before screening.

The nature of screening or selection depends on what property or characteristic is to be acquired or the property or characteristic for which improvement is sought, and many examples are discussed below. It is not usually necessary to understand the molecular basis by which particular products of recombination (recombinant segments) have acquired new or improved properties or characteristics relative to the starting substrates. For example, a genetic vaccine vector can have many component sequences each having a different intended role (e.g., coding sequence, regulatory sequences, targeting sequences, stability-conferring sequences, immunomodulatory sequences, sequences affecting antigen presentation, and sequences affecting integration). Each of these component sequences can be varied and recombined simultaneously. Screening/selection can then be performed, for example, for recombinant segments that have increased episomal maintenance in a target cell without the need to attribute such improvement to any of the individual component sequences of the vector.

Depending on the particular screening protocol used for a desired property, initial round(s) of screening can sometimes be performed in bacterial cells due to high transfection efficiencies and ease of culture. Later rounds, and other types of screening which are not amenable to screening in bacterial cells, are performed in mammalian cells to optimize recombinant segments for use in an environment close to that of their intended use. Final rounds of screening can be performed in the precise cell type of intended use (e.g., a human antigen-presenting cell). In some instances, this cell can be obtained from a patient to be treated with a view, for example, to minimizing problems of immunogenicity in this patient.

The screening or selection step identifies a subpopulation of recombinant segments that have evolved toward acquisition of a new or improved desired property or properties useful in genetic vaccination. Depending on the screen, the recombinant segments can be identified as components of cells, components of viruses or in free form. More than one round of screening or selection can be performed after each round of recombination.

If further improvement in a property is desired, at least one and usually a collection of recombinant segments surviving a first round of screening/selection are subject to a further round of recombination. These recombinant segments can be recombined with each other or with exogenous segments representing the original substrates or further variants thereof. Again, recombination can proceed in vitro or in vivo. If the previous screening step identifies desired recombinant segments as components of cells, the components can be subjected to further recombination in vivo, or can be subjected to further recombination in vitro, or can be isolated before performing a round of in vitro recombination. Conversely, if the previous screening step identifies desired recombinant segments in naked form or as components of viruses, these segments can be introduced into cells to perform a round of in vivo recombination. The second round of recombination, irrespective how performed, generates further recombinant segments which encompass additional diversity than is present in recombinant segments resulting from previous rounds.

The second round of recombination can be followed by a further round of screening/selection according to the principles discussed above for the first round. The stringency of screening/selection can be increased between rounds. Also, the nature of the screen and the property being screened for can vary between rounds if improvement in more than one property is desired or if acquiring more than one new property is desired. Additional rounds of recombination and screening can then be performed until the recombinant segments have sufficiently evolved to acquire the desired new or improved property or function.

Various screening methods for particular applications are described herein. In several instances, screening involves expressing the recombinant peptides or polypeptides encoded by the recombinant polynucleotides of the library as fusions with a protein that is displayed on the surface of a replicable genetic package. For example, phage display can be used. See, e.g, Cwirla et al., *Proc. Natl. Acad. Sci.* USA 87: 6378-6382 (1990); Devlin et al., *Science* 249: 404-406 (1990), Scott & Smith, *Science* 249: 386-388 (1990); Ladner et al., U.S. Pat. No. 5,571,698. Other replicable genetic packages include, for example, bacteria, eukaryotic viruses, yeast, and spores.

The genetic packages most frequently used for display libraries are bacteriophage, particularly filamentous phage, and especially phage M13, Fd and F1. Most work has involved inserting libraries encoding polypeptides to be displayed into either gIII or gVIII of these phage forming a fusion protein. See, e.g., Dower, WO 91/19818; Devlin, WO 91/18989; MacCafferty, WO 92/01047 (gene III); Huse, WO 92/06204; Kang, WO 92/18619 (gene VIII). Such a fusion protein comprises a signal sequence, usually but not necessarily, from the phage coat protein, a polypeptide to be displayed and either the gene III or gene VIII protein or a fragment thereof. Exogenous coding sequences are often inserted at or near the N-terminus of gene III or gene VIII although other insertion sites are possible.

Eukaryotic viruses can be used to display polypeptides in an analogous manner. For example, display of human heregulin fused to gp70 of Moloney murine leukemia virus has been reported by Han et al., *Proc. Natl. Acad. Sci. USA* 92: 9747-9751 (1995). Spores can also be used as replicable genetic packages. In this case, polypeptides are displayed from the outer surface of the spore. For example, spores from *B. subtilis* have been reported to be suitable. Sequences of coat proteins of these spores are provided by Donovan et al., *J. Mol. Biol.* 196, 1-10 (1987). Cells can also be used as replicable genetic packages. Polypeptides to be displayed are inserted into a gene encoding a cell protein that is expressed on the cells surface. Bacterial cells including *Salmonella typhimurium, Bacillus subtilis, Pseudomonas aeruginosa, Vibrio cholerae, Klebsiella pneumonia, Neisseria gonorrhoeae, Neisseria meningitidis, Bacteroides nodosus, Moraxella bovis*, and especially *Escherichia coli* are preferred. Details of outer surface proteins are discussed by Ladner et al., U.S. Pat. No. 5,571,698 and references cited therein. For example, the lamB protein of *E. coli* is suitable.

A basic concept of display methods that use phage or other replicable genetic package is the establishment of a physical association between DNA encoding a polypeptide to be screened and the polypeptide. This physical association is provided by the replicable genetic package, which displays a polypeptide as part of a capsid enclosing the genome of the phage or other package, wherein the polypeptide is encoded by the genome. The establishment of a physical association between polypeptides and their genetic material allows simultaneous mass screening of very large numbers of phage bearing different polypeptides. Phage displaying a polypeptide with affinity to a target, e.g., a receptor, bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means, or the polynucleotide that encodes the peptide or polypeptide can be used as part of a genetic vaccine.

C. Evolution of Improved Immunomodulatory Sequences

Cytokines can dramatically influence macrophage activation and $T_H1/T_H2$ cell differentiation, and thereby the outcome of infectious diseases. In addition, recent studies strongly suggest that DNA itself can act as adjuvant by activating the cells of the immune system. Specifically, unmethylated CpG-rich DNA sequences were shown to enhance $T_H1$ cell differentiation, activate cytokine synthesis by monocytes and induce proliferation of B lymphocytes. The invention thus provides methods for enhancing the immunomodulatory properties of genetic vaccines (a) by evolving the stimulatory properties of DNA itself and (b) by evolving genes encoding cytokines and related molecules that are involved in immune system regulation. These genes are then used in genetic vaccine vectors.

Of particular interest are IFN-α and IL-12, which skew immune responses towards a T helper 1 ($T_H1$) cell phenotype and, thereby, improve the host's capacity to counteract pathogen invasions. Also provided are methods of obtaining improved immunomodulatory nucleic acids that are capable of inhibiting or enhancing activation, differentiation, or anergy of antigen-specific T cells. Because of the limited information about the structures and mechanisms that regulate these events, molecular breeding techniques of the invention provide much faster solutions than rational design.

The methods of the invention typically involve the use of DNA shuffling or other methods to create a library of recombinant polynucleotides. The library is then screened to identify recombinant polynucleotides in the library, when included in a genetic vaccine vector or administered in conjunction with a genetic vaccine, are capable of enhancing or otherwise altering an immune response induced by the vector. The screening step, in some embodiments, can involve introducing a genetic vaccine vector that includes the recombinant polynucleotides into mammalian cells and determining whether the cells, or culture medium obtained by growing the cells, is capable of modulating an immune response.

Optimized recombinant vector modules obtained through polynucleotide recombination are useful not only as components of genetic vaccine vectors, but also for production of polypeptides, e.g., modified cytokines and the like, that can be administered to a mammal to enhance or shift an immune response. Polynucleotide sequences obtained using the DNA shuffling methods of the invention can be used as a component of a genetic vaccine, or can be used for production of cytokines and other immunomodulatory polypeptides that are themselves used as therapeutic or prophylactic reagents. If desired, the sequence of the optimized immunomodulatory polypeptide-encoding polynucleotides can be determined and the deduced amino acid sequence used to produce polypeptides using methods known to those of skill in the art.

1. Immunostimulatory DNA Sequences

The invention provides methods of obtaining polynucleotides that are immunostimulatory when introduced into a mammal. Oligonucleotides that contain hexamers with a central CpG flanked by two 5' purines (GpA or ApA) and two 3' pyrimidines (TpC or TpT) efficiently induce cytokine synthesis and B cell proliferation (Krieg et al. (1995) *Nature* 374: 546; Klinman et al. (1996) *Proc. Nat.'l. Acad. Sci. USA* 93: 2879; Pisetsky (1996) *Immunity* 5: 303-10) in vitro and act as adjuvants in vivo. Genetic vaccine vectors in which immunostimulatory sequence—(ISS) containing oligos are inserted have increased capacity to enhance antigen-specific antibody responses after DNA vaccination. The minimal length of an ISS oligonucleotide for functional activity in vitro is eight (Klinman et al., supra.). Twenty-mers with three CG motifs were found to be significantly more efficient in inducing cytokine synthesis than a 15-mer with two CG motifs (Id.). GGGG tetrads have been suggested to be involved in binding of DNA to cell surfaces (macrophages express receptors for example scavenger receptors, that bind DNA) (Pisetsky et al., supra.).

According to the invention, a library is generated by subjecting to recombination random DNA (e.g., fragments of human, murine, or other genomic DNA), oligonucleotides that contain known ISS, poly A, C, G or T sequences, or combinations thereof. The DNA, which includes at least first and second forms which differ from each other in two or more nucleotides, are recombined to produce a library of recombinant polynucleotides.

The library is then screened to identify those recombinant polynucleotides that exhibit immunostimulatory properties. For example, the library can be screened for induction cytokine production in vitro upon introduction of the library into an appropriate cell type. A diagram of this procedure is shown in FIG. 5. Among the cytokines that can be used as an indicator of immunostimulatory activity are, for example, IL-2, IL-4, IL-5, IL-6, IL-10, IL-12, IL-13, IL-15, and IFN-γ. One can also test for changes in ratios of IL-4/IFN-γ, IL-4/IL-2, IL-5/IFN-γ, IL-5/IL-2, IL-13/IFN-γ, IL-13/IL-2. An alternative screening method is the determination of the ability to induce proliferation of cells involved in immune responses, such as B cells, T cells, monocytes/macrophages, total PBL, and the like. Other screens include detecting induction of APC activation based on changes in expression levels of surface antigens, such as B7-1 (CD80), B7-2 (CD86), MHC class I and II, and CD14.

Other useful screens include identifying recombinant polynucleotides that induce T cell proliferation. Because ISS sequences induce B cell activation, and because of several homologies between surface antigens expressed by T cells and B cells, polynucleotides can be obtained that have stimulatory activities on T cells.

Libraries of recombinant polynucleotides can also be screened for improved CTL and antibody responses in vivo and for improved protection from infection, cancer, allergy or autoimmunity. Recombinant polynucleotides that exhibit the desired property can be recovered from the cell and, if further improvement is desired, the shuffling and screening can be repeated. Optimized ISS sequences can used as an adjuvant separately from an actual vaccine, or the DNA sequence of interest can be fused to a genetic vaccine vector.

2. Cytokines, Chemokines, and Accessory Molecules

The invention also provides methods for obtaining optimized cytokines, cytokine antagonists, chemokines, and other accessory molecules that direct, inhibit, or enhance immune responses. For example, the methods of the invention can be used to obtain genetic vaccines and other reagents (e.g., optimized cytokines, and the like) that, when administered to a mammal, improve or alter an immune response. These optimized immunomodulators are useful for treating infectious diseases, as well as other conditions such as inflammatory disorders, in an antigen non-specific manner.

For example, the methods of the invention can be used to develop optimized immunomodulatory molecules for treating allergies. The optimized immunomodulatory molecules can be used alone or in conjunction with antigen-specific genetic vaccines to prevent or treat allergy. Four basic mechanisms are available by which one can achieve specific immunotherapy of allergy; First, one can administer a reagent that causes a decrease in allergen-specific $T_H2$ cells. Second, a reagent can be administered that causes an increase in allergen-specific $T_H1$ cells. Third, one can direct an increase in suppressive $CD8^+$ T cells. Finally, allergy can be treated by inducing anergy of allergen-specific T cells. In this Example, cytokines are optimized using the methods of the invention to obtain reagents that are effective in achieving one or more of these immunotherapeutic goals. The methods of the invention are used to obtain anti-allergic cytokines that have one or more properties such as improved specific activity, improved secretion after introduction into target cells, are effective at a lower dose than natural cytokines, and fewer side effects. Targets of particular interest include interferon-α/γ, IL-10, IL-12, and antagonists of IL-4 and IL-13.

The optimized immunomodulators, or optimized recombinant polynucleotides that encode the immunomodulators, can be administered alone, or in combination with other accessory molecules. Inclusion of optimal concentrations of the appropriate molecules can enhance a desired immune response, and/or direct the induction or repression of a particular type of immune response. The polynucleotides that encode the optimized molecules can be included in a genetic vaccine vector, or the optimized molecules encoded by the genes can be administered as polypeptides.

In the methods of the invention, a library of recombinant polynucleotides that encode immunomodulators is created by subjecting substrate nucleic acids to a recombination protocol, such as DNA shuffling or other method known to those of skill in the art. The substrate nucleic acids are typically two or more forms of a nucleic acid that encodes an immunomodulator of interest.

Cytokines are among the immunomodulators that can be improved using the methods of the invention. Cytokine synthesis profiles play a crucial role in the capacity of the host to counteract viral, bacterial and parasitic infections, and cytokines can dramatically influence the efficacy of genetic vaccines and the outcome of infectious diseases. Several cytokines, for example IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, G-CSF, GM-CSF, IFN-α, IFN-γ, TGF-β, TNF-α, TNF-β, IL-20 (MDA-7), and flt-3 ligand have been shown stimulate immune responses in vitro or in vivo. Immune functions that can be enhanced using appropriate cytokines include, for example, B cell proliferation, Ig synthesis, Ig isotype switching, T cell proliferation and cytokine synthesis, differentiation of $T_H1$ and $T_H2$ cells, activation and proliferation of CTLs, activation and cytokine production by monocytes/macrophages/dendritic cells, and differentiation of dendritic cells from monocytes/macrophages.

In some embodiments, the invention provides methods of obtaining optimized immunomodulators that can direct an immune response towards a $T_H1$ or a $T_H2$ response. The ability to influence the direction of immune responses in this manner is of great importance in development of genetic vaccines. Altering the type of $T_H$ response can fundamentally change the outcome of an infectious disease. A high frequency of $T_H1$ cells generally protects from lethal infections with intracellular pathogens, whereas a dominant $T_H2$ phenotype often results in disseminated, chronic infections. For example, in human, the $T_H1$ phenotype is present in the tuberculoid (resistant) form of leprosy, while the $T_H2$ phenotype is found in lepromatous, multibacillary-(susceptible) lesions (Yamamura et al. (1991) *Science* 254: 277). Late-stage AIDS patients have the $T_H2$ phenotype. Studies in family members indicate that survival from meningococcal septicemia depends on the cytokine synthesis profile of PBL, with high IL-10 synthesis being associated with a high risk of lethal outcome and high TNF-α being associated with a low risk. Similar examples are found in mice. For example, BALB/c mice are susceptible to *Leishmania major* infection; these mice develop a disseminated fatal disease with a $T_H2$ phenotype. Treatment with anti-IL-4 monoclonal antibodies or with IL-12 induces a $T_H1$ response, resulting in healing. Anti-interferon-γ monoclonal antibodies exacerbate the disease. For some applications, it is preferable to direct an immune response in the direction of a $T_H2$ response. For example, where increased mucosal immunity is desired, including protective immunity, enhancing the $T_H2$ response can lead to increased antibody production, particularly IgA.

T helper ($T_H$) cells are probably the most important regulators of the immune system. $T_H$ cells are divided into two subsets, based on their cytokine synthesis pattern (Mosmann and Coffman (1989) *Adv. Immunol.* 46: 111). $T_H1$ cells produce high levels of the cytokines IL-2 and IFN-γ and no or minimal levels of IL-4, IL-5 and IL-13. In contrast, $T_H2$ cells produce high levels of IL-4, IL-5 and IL-13, and IL-2 and IFN-γ production is minimal or absent. $T_H1$ cells activate macrophages, dendritic cells and augment the cytolytic activity of CD8+ cytotoxic T lymphocytes and natural killer (NK) cells (Paul and Seder (1994) *Cell* 76: 241), whereas $T_H2$ cells provide efficient help for B cells and also mediate allergic responses due to the capacity of $T_H2$ cells to induce IgE isotype switching and differentiation of B cells into IgE secreting cells (Punnonen et al. (1993) *Proc. Nat'l. Acad. Sci. USA* 90: 3730).

The screening methods for improved cytokines, chemokines, and other accessory molecules are generally based on identification of modified molecules that exhibit improved specific activity on target cells that are sensitive to the respective cytokine, chemokine, or other accessory molecules. A library of recombinant cytokine, chemokine, or accessory molecule nucleic acids can be expressed on phage or as purified protein and tested using in vitro cell culture assays, for example. Importantly, when analyzing the recombinant nucleic acids as components of DNA vaccines, one can identify the most optimal DNA sequences (in addition to the functions of the protein products) in terms of their immunostimulatory properties, transfection efficiency, and their capacity to improve the stabilities of the vectors. The identified optimized recombinant nucleic acids can then be subjected to new rounds of shuffling and selection.

In one embodiment of the invention, cytokines are evolved that direct differentiation of $T_H1$ cells. Because of their capacities to skew immune responses towards a $T_H1$ phenotype, the genes encoding interferon-α (IFN-α) and interleukin-12 (IL-12) are preferred substrates for recombination and selection in order to obtain maximal specific activity and capacity to act as adjuvants in genetic vaccinations. IFN-α: is a particularly preferred target for optimization using the methods of the invention because of its effects on the immune system, tumor cells growth and viral replication. Due to these activities, IFN-α: was the first cytokine to be used in clinical practice. Today, IFN-α is used for a wide variety of applications, including several types of cancers and viral diseases. IFN-α: also efficiently directs differentiation of human T cells into $T_H1$ phenotype (Parronchi et al. (1992) *J. Immunol.* 149: 2977). However, it has not been thoroughly investigated in vaccination models, because, in contrast to human systems, it does not affect $T_H1$ differentiation in mice. The species difference was recently explained by data indicating that, like IL-12, IFN-α induces STAT4 activation in human cells but not in murine cells, and STAT4 has been shown to be required in IL-12 mediated $T_H1$ differentiation (Thierfelder et al. (1996) *Nature* 382: 171).

Family DNA shuffling is a preferred method for optimizing IFN-α, using as substrates the mammalian IFN-α genes, which are 85%-97% homologous. Greater than $10^{26}$ distinct recombinants can be generated from the natural diversity in these genes. To allow rapid parallel analysis of recombinant interferons, one can employ high throughput methods for their expression and biological assay as fusion proteins on bacteriophage. Recombinants with improved potency and selectivity profiles are being selectively bred for improved activity. Variants which demonstrate improved binding to IFN-α receptors can be selected for further analysis using a screen for mutants with optimal capacity to direct $T_H1$ differentiation. More specifically, the capacities of IFN-α mutants to induce IL-2 and IFN-γ production in in vitro human T lymphocyte cultures can be studied by cytokine-specific ELISA and cytoplasmic cytokine staining and flow cytometry.

IL-12 is perhaps the most potent cytokine that directs $T_H1$ responses, and it has also been shown to act as an adjuvant and enhance $T_H1$ responses following genetic vaccinations (Kim et al. (1997) *J. Immunol.* 158: 816). IL-12 is both structurally and functionally a unique cytokine. It is the only heterodimeric cytokine known to date, composed of a 35 kD light chain (p35) and a 40 kD heavy chain (p40) (Kobayashi et al (1989) *J. Exp. Med.* 170: 827; Stem et al. (1990) Proc. Nat'l. Acad. Sci. USA 87: 6808). Recently Lieschke et al. ((1997) *Nature Biotech.* 15: 35) demonstrated that a fusion between p35 and p40 genes results in a single gene that has activity comparable to that of the two genes expressed separately. These data indicate that it is possible to shuffle IL-12 genes as one entity, which is beneficial in designing the shuffling protocol. Because of its T cell growth promoting activities, one can use normal human peripheral blood T cells in the selection of the most active IL-12 genes, enabling direct selection of IL-12 mutants with the most potent activities on human T cells. IL-12 mutants can be expressed in CHO cells, for example, and the ability of the supernatants to induce T cell proliferation determined (FIG. 6). The concentrations of IL-12 in the supernatants can be normalized based on a specific ELISA that detects a tag fused to the shuffled IL-12 molecules.

Incorporation of evolved IFN-α and/or IL-12 genes into genetic vaccine vectors is expected to be safe. The safety of IFN-α: has been demonstrated in numerous clinical studies and in everyday hospital practice. A Phase II trial of IL-12 in the treatment of patients with renal cell cancer resulted in several unexpected adverse effects (Tahara et al. (1995) *Human Gene Therapy* 6: 1607). However, IL-12 gene as a component of genetic vaccines aims at high local expression levels, whereas the levels observed in circulation are minimal compared to those observed after systemic bolus injections. In addition, some of the adverse effects of systemic IL-12 treatments are likely to be related to its unusually long half-life (up to 48 hours in monkeys). DNA shuffling may allow selection for a shorter half-life, thereby reducing the toxicity even after high bolus doses.

In other cases, genetic vaccines that can induce $T_H2$ responses are preferred, especially when improved antibody production is desired. As an example, IL-4 has been shown to direct differentiation of $T_H2$ cells (which produce high levels of IL-4, IL-5 and IL-13, and mediate allergic immune responses). Immune responses that are skewed towards $T_H2$ phenotype are preferred when genetic vaccines are used to immunize against autoimmune diseases prophylactically. $T_H1$ responses are also preferred when the vaccines are used to treat and modulate existing autoimmune responses, because autoreactive T cells are generally of $T_H1$ phenotype (Liblau et al. (1995) *Immunol. Today* 16:34-38). IL-4 is also the most potent cytokine in induction of IgE synthesis; IL-4 deficient mice are unable to produce IgE. Asthma and allergies are associated with an increased frequency of IL-4 producing cells, and are genetically linked to the locus encoding IL-4, which is on chromosome 5 (in close proximity to genes encoding IL-3, IL-5, IL-9, IL-13 and GM-CSF). IL-4, which is produced by activated T cells, basophils and mast cells, is a protein that has 153 amino acids and two potential N-glycosylation sites. Human IL-4 is only approximately 50% identical to mouse IL-4, and IL-4 activity is species-specific. In human, IL-13 has activities similar to those of IL-4, but IL-13 is less potent than IL-4 in inducing IgE synthesis. IL-4 is the only cytokine known to direct $T_H2$ differentiation.

Improved IL-2 agonists are also useful in directing $T_H2$ cell differentiation, whereas improved IL-4 antagonists can direct $T_H1$ cell differentiation. Improved IL-4 agonists and antagonists can be generated by shuffling of IL-4 or soluble IL-4 receptor. The IL-4 receptor consists of an IL-4R α-chain (140 kD high-affinity binding unit) and an IL-2R γ-chain (these cytokine receptors share a common γ-chain). The IL-4R α-chain is shared by IL-4 and IL-13 receptor complexes. Both IL-4 and IL-13 induce phosphorylation of the IL-4R α-chain, but expression of IL-4R α-chain alone on transfectants is not sufficient to provide a functional IL-4R. Soluble IL-4 receptor currently in clinical trials for the treatment of allergies. Using the DNA shuffling methods of the invention, one can evolve a soluble IL-4 receptor that has improved affinity for IL-4. Such receptors are useful for the treatment of asthma and other $T_H2$ cell mediated diseases, such as severe allergies. The shuffling reactions can take advantage of natural diversity present in cDNA libraries from activated T cells from human and other primates. In a typical embodiment, a shuffled IL-4R α-chain library is expressed on a phage, and mutants that bind to IL-4 with improved affinity are identified. The biological activity of the selected mutants is then assayed using cell-based assays.

IL-2 and IL-15 are also of particular interest for use in genetic vaccines. IL-2 acts as a growth factor for activated B and T cells, and it also modulates the functions of NK-cells. IL-2 is predominantly produced by $T_H1$-like T cell clones, and, therefore, it is considered mainly to function in delayed type hypersensitivity reactions. However, IL-2 also has potent, direct effects on proliferation and Ig-synthesis by B cells. The complex immunoregulatory properties of IL-2 are reflected in the phenotype of IL-2 deficient mice, which have high mortality at young age and multiple defects in their immune functions including spontaneous development of inflammatory bowel disease. IL-15 is a more recently identified cytokine produced by multiple cell types. IL-15 shares several, but not all, activities with IL-2. Both IL-2 and IL-15 induce B cell growth and differentiation. However, assuming that IL-15 production in IL-2 deficient mice is normal, it is clear that IL-15 cannot substitute for the function of IL-2 in vivo, since these mice have multiple immunodeficiencies. IL-2 has been shown to synergistically enhance IL-10-induced human Ig production in the presence of anti-CD40 mAbs, but it antagonized the effects of IL-4. IL-2 also enhances IL-4-dependent IgE synthesis by purified B cells.

On the other hand, IL-2 was shown to inhibit IL-4-dependent murine IgG1 and IgE synthesis both in vitro and in vivo. Similarly, IL-2 inhibited IL-4-dependent human IgE synthesis by unfractionated human PBMC, but the effects were less significant than those of IFN-α or IFN-γ. Due to their capacities to activate both B and T cells, IL-2 and IL-15 are useful in vaccinations. In fact, IL-2, as protein and as a component of genetic vaccines, has been shown to improve the efficacy of the vaccinations. Improving the specific activity and/or expression levels/kinetics of IL-2 and IL-15 through use of the DNA shuffling methods of the invention increases the advantageous effects compared to wild-type IL-2 and IL-15.

Another cytokine of particular interest for optimization and use in genetic vaccines according to the methods of the invention is interleukin-6. IL-6 is a monocyte-derived cytokine that was originally described as a B cell differentiation factor or B cell stimulatory factor-2 because of its ability to enhance Ig levels secreted by activated B cells. IL-6 has also been shown to enhance IL-4-induced IgE synthesis. It has also been suggested that IL-6 is an obligatory factor for human IgE synthesis, because neutralizing anti-IL-6 mAbs completely blocked IL-4-induced IgE synthesis. IL-6 deficient mice have impaired capacity to produce IgA. Because of its potent activities on the differentiation of B cells, IL-6 can enhance the levels of specific antibodies produced following vaccination. It is particularly useful as a component of DNA vaccines because high local concentrations can be achieved, thereby providing the most potent effects on the cells adjacent to the transfected cells expressing the immunogenic antigen. IL-6 with improved specific activity and/or with improved expression levels, obtained by DNA shuffling, will have more beneficial effects than the wild-type IL-6.

Interleukin-8 is another example of a cytokine that, when modified according to the methods of the invention, is useful in genetic vaccines. IL-8 was originally identified as a monocyte-derived neutrophil chemotactic and activating factor. Subsequently, IL-8 was also shown to be chemotactic for T cells and to activate basophils resulting in enhanced histamine and leukotriene release from these cells. Furthermore, IL-8 inhibits adhesion of neutrophils to cytokine-activated endothelial cell monolayers, and it protects these cells from neutrophil-mediated damage. Therefore, endothelial cell derived IL-8 was suggested to attenuate inflammatory events occurring in the proximity of blood vessel walls. IL-8 also modulates immunoglobulin production, and inhibits IL-4-induced IgG4 and IgE synthesis by both unfractionated human PBMC and purified B cells in vitro. This inhibitory effect was independent of IFN-α, IFN-γ or prostaglandin E2. In addition, IL-8 inhibited spontaneous IgE synthesis by PBMC derived from atopic patients. Due to its capacity to attract inflammatory cells, IL-8, like other chemotactic agents, is useful in potentiating the functional properties of vaccines, including DNA vaccines (acting as an adjuvant). The beneficial effects of IL-8 can be improved by using the DNA shuffling methods of the invention to obtain IL-8 with improved specific activity and/or with improved expression in target cells.

Interleukin-5, and antagonists thereof, can also be optimized using the methods of the invention for use in genetic vaccines. IL-5 is primarily produced by $T_H2$-type T cells and appears to play an important role in the pathogenesis of allergic disorders because of its ability to induce eosinophilia. IL-5 acts as an eosinophil differentiation and survival factor in both mouse and man. Blocking IL-5 activity by use of neutralizing monoclonal antibodies strongly inhibits pulmonary eosinophilia and hyperactivity in mouse models, and IL-5 deficient mice do not develop eosinophilia. These data also suggest that IL-5 antagonists may have therapeutic potential in the treatment of allergic eosinophilia.

IL-5 has also been shown to enhance both proliferation of, and Ig synthesis by, activated mouse and human B cells. However, other studies suggested that IL-5 has no effect on proliferation of human B cells, whereas it activated eosinophils. IL-5 apparently is not crucial for maturation or differentiation of conventional B cells, because antibody responses in IL-5 deficient mice are normal. However, these mice have a developmental defect in their CD5+ B cells indicating that IL-5 is required for normal differentiation of this B cell subset in mice. At suboptimal concentrations of IL-4, IL-5 was shown to enhance IgE synthesis by human B cells in vitro. Furthermore, a recent study suggested that the effects of IL-5 on human B cells depend on the mode of B cell stimulation. IL-5 significantly enhanced IgM synthesis by B cells stimulated with *Moraxella catarrhalis*. In addition, IL-5 synergized with suboptimal concentrations of IL-2, but had no effect on Ig synthesis by SAC-activated B cells. Activated human B cells also expressed IL-5 mRNA suggesting that IL-5 may also regulate B cell function, including IgE synthesis, by autocrine mechanisms.

The invention provides methods of evolving an IL-5 antagonist that efficiently binds to and neutralizes IL-5 or its receptor. These antagonists are useful as a component of vaccines used for prophylaxis and treatment of allergies. Nucleic acids encoding IL-5, for example, from human and other mammalian species, are shuffled and screened for binding to immobilized IL-5R for the initial screening. Polypeptides that exhibit the desired effect in the initial screening assays can then be screened for the highest biological activity using assays such as inhibition of growth of IL-5 dependent cells lines cultured in the presence of recombinant wild-type IL-5. Alternatively, shuffled IL-5R α-chains are screened for improved binding to IL-5.

Tumor necrosis factors (α and β) and their receptors are also suitable targets for modification and use in genetic vaccines. TNF-α, which was originally described as cachectin because of its ability to cause necrosis of tumors, is a 17 kDa protein that is produced in low quantities by almost all cells in the human body following activation. TNF-α acts as an endogenous pyrogen and induces the synthesis of several proinflammatory cytokines, stimulates the production of acute phase proteins, and induces proliferation of fibroblasts. TNF-α plays a major role in the pathogenesis of endotoxin shock. A membrane-bound form of TNF-α (mTNF-α), which is involved in interactions between B- and T-cells, is rapidly upregulated within four hours of T cell activation. mTNF-α plays a role in the polyclonal B cell activation observed in patients infected with HIV. Monoclonal antibodies specific for mTNF-α or the p55 TNF-α receptor strongly inhibit IgE synthesis induced by activated CD4+ T cell clones or their membranes. Mice deficient for p55 TNF-αR are resistant to endotoxic shock, and soluble TNF-AR prevents autoimmune diabetes mellitus in NOD mice. Phase III trials using sTNF-αR in the treatment of rheumatoid arthritis are in progress, after promising results obtained in the phase II trials.

The methods of the invention can be used to, for example, evolve a soluble TNF-αR that has improved affinity, and thus is capable of acting as an antagonist for TNF activity. Nucleic acids that encode TNF-αR and exhibit sequence diversity, such as the natural diversity observed in cDNA libraries from activated T cells of human and other primates, are shuffled. The shuffled nucleic acids are expressed, e.g., on phage, after which mutants are selected that bind to TNF-α with improved affinity. If desired, the improved mutants can be subjected to further assays using biological activity, and the shuffled genes can be subjected to one or more rounds of shuffling and screening.

Another target of interest for application of the methods of the invention is interferon-γ, and the evolution of antagonists of this cytokine. The receptor for IFN-γ consists of a binding component glycoprotein of 90 kD, a 228 amino acid extracellular portion, a transmembrane region, and a 222 amino acid intracellular region. Glycosylation is not required for functional activity. A single chain provides high affinity binding ($10^{-9}$–$10^{-10}$M), but is not sufficient for signaling. Receptor components dimerize upon ligand binding. The mouse IFN-γ receptor is 53% identical to that of mouse at the amino acid level. The human and mouse receptors only bind human and mouse IFN-γ, respectively. Vaccinia, cowpox and camelpox viruses have homologues of sIFN-γR, which have relatively low amino acid sequence similarity (~20%), but are capable of efficient neutralization of IFN-γ in vitro. These homologues bind human, bovine, rat (but not mouse) IFN-γ, and may have in vivo activity as IFN-γ antagonists. All eight cysteines are conserved in human, mouse, myxoma and Shope fibroma virus (6 in vaccinia virus) IFN-γR polypeptides, indicating similar 3-D structures. An extracellular portion of mIFN-γR with a kD of 100-300 μM has been expressed in insect cells. Treatment of NZB/W mice (a mouse model of human SLE) with msIFN-γ receptor (100 mg/three times a week i.p.) inhibits the onset of glomerulonephritis. All mice treated with sIFN-γ or anti-IFN-γ mAbs were alive 4 weeks after the treatment was discontinued, compared with 50% in a placebo group, and 78% of IFN-γ-treated mice died.

The methods of the invention can be used to evolve soluble IFN-γR receptor polypeptides with improved affinity, and to evolve IFN-γ with improved specific activity and improved capacity to activate cellular immune responses. In each case nucleic acids encoding the respective polypeptide, and which exhibit sequence diversity (e.g., that observed in cDNA libraries from activated T cells from human and other primates), are subjected to recombination and screened to identify those recombinant nucleic acids that encode a polypeptide having improved activity. In the case of shuffled IFN-γR, the library of shuffled nucleic acids can be expressed on phage, which are screened to identify mutants that bind to IFN-γ with improved affinity. In the case of IFN-γ, the shuffled library is analyzed for improved specific activity and improved activation of the immune system, for example, by using activation of monocytes/macrophages as an assay. The evolved IFN-γ molecules can improve the efficacy of vaccinations (e.g. when used as adjuvants).

Diseases that can be treated using high-affinity sIFN-γR polypeptides obtained using the methods of the invention include, for example, multiple sclerosis, systemic lupus erythematosus (SLE), organ rejection after treatment, and graft versus host disease. Multiple sclerosis, for example, is characterized by increased expression of IFN-γ in the brain of the patients, and increased production of IFN-γ by patients' T cells in vitro. IFN-γ treatment has been shown to significantly exacerbate the disease (in contrast to EAE in mice).

Transforming growth factor (TGF)-β is another cytokine that can be optimized for use in genetic vaccines using the methods of the invention. TGF-β has growth regulatory activities on essentially all cell types, and it has also been shown to have complex modulatory effects on the cells of the immune system. TGF-β inhibits proliferation of both B and T cells, and it also suppresses development of and differentiation of cytotoxic T cells and NK cells. TGF-β has been shown to direct IgA switching in both murine and human B cells. It was also shown to induce germline a transcription in murine and human B cells, supporting the conclusion that TGF-β can specifically induce IgA switching.

Due to its capacity to direct IgA switching, TGF-β is useful as a component of DNA vaccines which aim at inducing potent mucosal immunity, e.g. vaccines for diarrhea. Also, because of its potent anti-proliferative effects TGF-β is useful as a component of therapeutical cancer vaccines. TGF-β with improved specific activity and/or with improved expression levels/kinetics will have increased beneficial effects compared to the wild-type TGF-β.

Cytokines that can be optimized using the methods of the invention also include granulocyte colony stimulating factor (G-CSF) and granulocyte/macrophage colony stimulating factor (GM-CSF). These cytokines induce differentiation of bone marrow stem cell into granulocytes/macrophages. Administration of G-CSF and GM-CSF significantly improve recovery from bone marrow (BM) transplantation and radiotherapy, reducing infections and time the patients have to spend in hospitals. GM-CSF enhances antibody production following DNA vaccination. G-CSF is a 175 amino acid protein, while GM-CSF has 127 amino acids. Human G-CSF is 73% identical at the amino acid level to murine G-CSF and the two proteins show species cross-reactivity. G-CSF has a homodimeric receptor (dimeric with kD of ~200 μM, monomeric ~2-4 nM), and the receptor for GM-CSF is a three subunit complex. Cell lines transfected with cDNA encoding G-CSF R proliferate in response to G-CSF. Cell lines dependent of GM-CSF available (such as TF-1). G-CSF is nontoxic and is presently working very well as a drug. However, the treatment is expensive, and more potent G-CSF might reduce the cost for patients and to the health care. Treatments with these cytokines are typically short-lasting and the patients are likely to never need the same treatment again reducing likelihood of problems with immunogenicity.

The methods of the invention are useful for evolving G-CSF and/or GM-CSF which have improved specific activity, as well as other polypeptides that have G-CSF and/or GM-CSF activity. G-CSF and/or GM-CSF nucleic acids having sequence diversity, e.g., those obtained from cDNA libraries from diverse species, are shuffled to create a library of shuffled G-CSF and/or GM-CSF genes. These libraries can be screened by, for example, picking colonies, transfecting the plasmids into a suitable host cell (e.g., CHO cells), and assaying the supernatants using receptor-positive cell lines. Alternatively, phage display or related techniques can be used, again using receptor-positive cell lines. Yet another screening method involves transfecting the shuffled genes into G-CSF/GM-CSF-dependent cell lines. The cells are grown one cell per well and/or at very low density in large flasks, and the cells that grow fastest are selected. Shuffled genes from these cells are isolated; if desired, these genes can be used for additional rounds of shuffling and selection.

Ciliary neurotrophic factor (CNTF) is another suitable target for application of the methods of the invention. CNTF has 200 amino acids which exhibit 80% sequence identity between rat and rabbit CNTF polypeptides. CNTF has IL-6-like inflammatory effects, and induces synthesis of acute phase proteins. CNTF is a cytosolic protein which belongs to the IL-6/IL-11/LIF/oncostatin M-family, and becomes biologically active only after becoming available either by cellular lesion or by an unknown release mechanism. CNTF is expressed by myelinating Schwann cells, astrocytes and sciatic nerves. Structurally, CNTF is a dimeric protein, with a novel anti-parallel arrangement of the subunits. Each subunit adopts a double crossover four-helix bundle fold, in which two helices contribute to the dimer interface. Lys-155 mutants lose activity, and some Glu-153 mutants have 5-10 higher biological activity. The receptor for CNTF consists of a specific CNTF receptor chain, gp130, and a LIF-β receptor. The CNTFR α-chain lacks a transmembrane domain portion, instead being GPI-anchored. At high concentration, CNTF can mediate CNTFR-independent responses. Soluble CNTFR binds CNTF and thereafter can bind to LIFR and induce signaling through gp130. CNTF enhances survival of several types of neurons, and protects neurons in an animal model of Huntington disease (in contrast to NGF, neurotrophic factor, and neurotrophin-3). CNTF receptor knockout mice have severe motor neuron deficits at birth, and CNTF knockout mice exhibit such deficits postnatally. CNTF also reduces obesity in mouse models. Decreased expression of CNTF is sometimes observed in psychiatric patients. Phase I studies in patients with ALS (annual incidence ~1/100 000, 5% familiar cases, 90% die within 6 years) found significant side effects after doses higher than 5 mg/kg/day subcutaneously (including anorexia, weight loss, reactivation of herpes simplex virus (HSV1), cough, increased oral secretions). Antibodies against CNTF were detected in almost all patients, thus illustrating the need for alternative CNTF with different immunological properties.

The recombination and screening methods of the invention can be used to obtain modified CNTF polypeptides that exhibit decreased immunogenicity in vivo; higher specific activity is also obtainable using the methods. Shuffling is conducted using nucleic acids encoding CNTF. In a preferred embodiment, an IL-6/LIF/(CNTF) hybrid is obtained by shuffling using an excess of oligonucleotides that encode to the receptor binding sites of CNTF. Phage display can then be used to test for lack of binding to the IL-6/LIF receptor. This initial screen is followed by a test for high affinity binding to the CNTF receptor, and, if desired, functional assays using CNTF responsive cell lines. The shuffled CNTF polypeptides can be tested to identify those that exhibit reduced immunogenicity upon administration to a mammal.

Another way in which the recombination and screening methods of the invention can be used to optimize CNTF is to improve secretion of the polypeptide. When a CNTF cDNA is operably linked to a leader sequence of hNGF, only 35-40 percent of the total CNTF produced is secreted.

Target diseases for treatment with optimized CNTF, using either the shuffled gene in an expression vector as in DNA vaccines, or a purified protein, include obesity, amyotrophic lateral sclerosis (ALS, Lou Gehrig's disease), diabetic neuropathy, stroke, and brain surgery.

Polynucleotides that encode chemokines can also be optimized using the methods of the invention and included in a genetic vaccine vector. At least three classes of chemokines are known, based on structure: C chemokines (such as lymphotactin), C—C chemokines (such as MCP-1, MCP-2, MCP-3, MCP-4, MIP-1a, MIP-1b, RANTES), C—X—C chemokines (such as IL-8, SDF-1, ELR, Mig, IP10) (Premack and Schall (1996) *Nature Med.* 2: 1174). Chemokines can attract other cells that mediate immune and inflammatory functions, thereby potentiating the immune response. Cells that are attracted by different types of chemokines include, for example, lymphocytes, monocytes and neutrophils. Generally, C—X—C chemokines are chemoattractants for neutrophils but not for monocytes, C—C chemokines attract monocytes and lymphocytes but not neutrophils, C chemokine attracts lymphocytes.

Genetic vaccine vectors can also include optimized recombinant polynucleotides that encode surface-bound accessory molecules, such as those that are involved in modulation and potentiation of immune responses. These molecules, which include, for example, B7-1 (CD80), B7-2 (CD86), CD40, ligand for CD40, CTLA-4, CD28, and CD150 (SLAM), can be subjected to DNA shuffling to obtain variants have altered and/or improved activities.

Optimized recombinant polynucleotides that encode CD1 molecules are also useful in a genetic vaccine vector for certain applications. CD1 are nonpolymorphic molecules that are structurally and functionally related to MHC molecules. Importantly, CD 1 has MHC-like activities, and it can function as an antigen presenting molecule (Porcelli (1995) *Adv. Immunol.* 59: 1). CD1 is highly-expressed on dendritic cells, which are very efficient antigen presenting cells. Simultaneous transfection of target cells with DNA vaccine vectors encoding CD1 and an antigen of interest is likely to boost the immune response. Because CD1 cells, in contrast to MHC molecules, exhibit limited allelic diversity in an outbred population (Porcelli, supra.), large populations of individuals with different genetic backgrounds can be vaccinated with one CD1 allele. The functional properties of CD1 molecules can be improved by the DNA shuffling methods of the invention.

Optimized recombinant TAP genes and/or gene products can also be included in a genetic vaccine vector. TAP genes and their optimization for various purposes are discussed in more detail below. Moreover, heat shock proteins (HSP), such as HSP70, can also be evolved for improved presentation and processing of antigens. HSP70 has been shown to act as adjuvant for induction of $CD8^+$ T cell activation and it enhances immunogenicity of specific antigenic peptides (Blachere et al. (1997) *J. Exp. Med.* 186:1315-22). When HSP70 is encoded by a genetic vaccine vector, it is likely to enhance presentation and processing of antigenic peptides and thereby improve the efficacy of the genetic vaccines. DNA shuffling can be used to further improve the properties, including adjuvant activity, of heat shock proteins, such as HSP70.

Recombinantly produced cytokine, chemokine, and accessory molecule polypeptides, as well as antagonists of these molecules, can be used to influence the type of immune response to a given stimulus. However, the administration of polypeptides sometimes has shortcomings, including short half life, high expense, difficult to store (must be stored at 4° C.), and a requirement for large volumes. Also, bolus injections can sometimes cause side effects. Administration of polynucleotides that encode the recombinant cytokines or other molecules overcomes most or all of these problems. DNA, for example, can be prepared in high purity, is stable, temperature resistant, noninfectious, easy to manufacture. In addition, polynucleotide-mediated administration of cytokines can provide long-lasting, consistent expression, and administration of polynucleotides in general is regarded as being safe.

The functions of cytokines, chemokines and accessory molecules are redundant and pleiotropic, and therefore can be difficult to determine which cytokines or cytokine combinations are the most potent in inducing and enhancing antigen specific immune responses following vaccination. Furthermore, the most useful combination of cytokines and accessory molecules is typically different depending on the type of immune response that is desired following vaccination. As an example, IL-4 has been shown to direct differentiation of $T_H2$ cells (which produce high levels of IL-4, IL-5 and IL-13, and mediate allergic immune responses), whereas IFN-γ and IL-12 direct differentiation of $T_H1$ cells (which produce high levels of IL-2 and IFN-γ), and mediate delayed type immune responses. Moreover, the most useful combination of cytokines and accessory molecules is also likely to depend on the antigen used in the vaccination. The invention provides a solution to this problem of obtaining an optimized genetic vaccine cocktail. Different combinations of cytokines, chemokines and accessory molecules are assembled into vectors using the methods described herein. These vectors are then screened for their capacity to induce immune responses in vivo and in vitro.

Large libraries of vectors, generated by gene shuffling and combinatorial molecular biology, are screened for maximal capacity to direct immune responses towards, for example, a $T_H1$ or $T_H2$ phenotype, as desired. A library of different vectors can be generated by assembling different evolved promoters, (evolved) cytokines, (evolved) cytokine antagonists, (evolved) chemokines, (evolved) accessory molecules and immunostimulatory sequences, each of which can be prepared using methods described herein. DNA sequences and compounds that facilitate the transfection and expression can be included. If the pathogen(s) is known, specific DNA sequences encoding immunogenic antigens from the pathogen can be incorporated into these vectors providing protective immunity against the pathogen(s) (as in genetic vaccines).

Initial screening is preferably carried out in vitro. For example, the library can be introduced into cells which are tested for ability to induce differentiation of T cells capable of producing cytokines that are indicative of the type of immune response desired. For a $T_H1$ response, for example, the library is screened to identify recombinant polynucleotides that are capable of inducing T cells to produce IL-2 and IFN-γ, while screening for induction of T cell production of IL-4, IL-5, and IL-13 is performed to identify recombinant polynucleotides that favor a $T_H2$ response.

Screening can also be conducted in vivo, using animal models. For example, vectors produced using the methods of the invention can be tested for ability to protect against a lethal infection. Another screening method involves injection of *Leishmania major* parasites into footpads of BALB/c mice (nonhealer). Pools of plasmids are injected i.v., i.p. or into footpads of these mice and the size of the footpad swelling is followed. Yet another in vivo screening method involves detection of IgE levels after infection with *Nippostrongylus brasiliensis*. High levels indicate a $T_H2$ response, while low levels of IgE indicate a $T_H1$ response.

Successful results in animal models are easy to verify in humans. In vitro screening can be conducted to test for human $T_H1$ or $T_H2$ phenotype, or for other desired immune response. Vectors can also be tested for ability to induce protection against infection in humans.

Because the principles of immune functions are similar in a wide variety of infections, immunostimulating DNA vaccine vectors may not only be useful in the treatment of a number of infectious diseases but also in prevention of the infections, when the vectors are delivered to the sites of the entry of the pathogen (e.g., the lung or gut).

3. Agonists or Antagonists of Cellular Receptors

The invention also provides methods for obtaining optimized recombinant polynucleotides that encode a peptide or polypeptide that can interact with a cellular receptor that is involved in mediating an immune response. The optimized recombinant polynucleotides can act as an agonist or an antagonist of the receptor.

Cytokine antagonists can be used as components of genetic vaccine cocktails. Blocking immunosuppressive cytokines, rather than adding single proinflammatory cytokines, is likely to potentiate the immune response in a more general manner, because several pathways are potentiated at the same time. By appropriate choice of antagonist, one can tailor the immune response induced by a genetic vaccine in order to obtain the response that is most effective in achieving the desired effect.

Antagonists against any cytokine can be used as appropriate; particular cytokines of interest for blocking include, for example, IL-4, IL-13, IL-10, and the like.

The invention provides methods of obtaining cytokine antagonists that exhibit greater effectiveness in blocking the action of the respective cytokine. Polynucleotides that encode improved cytokine antagonists can be obtained by using gene shuffling to generate a recombinant library of polynucleotides which are then screened to identify those that encode an improved antagonist. As substrates for the DNA shuffling, one can use, for example, polynucleotides that encode receptors for the respective cytokine. At least two forms of the substrate will be present in the recombination reaction, with each form differing from the other in at least one nucleotide position. In a preferred embodiment, the different forms of the polynucleotide are homologous cytokine receptor genes from different organisms. The resulting library of recombinant polynucleotides is then screened to identify those that encode cytokine antagonists with the desired affinity and biological activity.

As one example of the type of effect that one can achieve by including a cytokine antagonist in a genetic vaccine cocktail, as well as how the effect can be improved using the DNA shuffling methods of the invention, IL-10 is discussed. The same rationale can be applied to obtaining and using antagonists of other cytokines. Interleukin-10 (IL-10) is perhaps the most potent anti-inflammatory cytokine known to date. IL-10 inhibits a number of pathways that potentiate inflammatory responses. The biological activities of IL-10 include inhibition of MHC class II expression on monocytes, inhibition of production of IL-1, IL-6, IL-12, TNF-α by monocytes/macrophages, and inhibition of proliferation and IL-2 production by T lymphocytes. The significance of IL-10 as a regulatory molecule of immune and inflammatory responses was clearly demonstrated in IL-10 deficient mice. These mice are growth-retarded, anemic and spontaneously develop an inflammatory bowel disease (Kuhn et al. (1993) *Cell* 75: 263). In addition, both innate and acquired immunity to *Listeria monocytogenes* were shown to be elevated in IL-10 deficient mice (Dai et al. (1997) *J. Immunol.* 158: 2259). It has also been suggested that genetic differences in the levels of IL-10 production may affect the risk of patients to die from complications meningococcal infection. Families with high IL-10 production had 20-fold increased risk of fatal outcome of meningococcal disease (Westendorp et al. (1997) *Lancet* 349: 170).

IL-10 has been shown to activate normal and malignant B cells in vitro, but it does not appear to be a major growth promoting cytokine for normal B cells in vivo, because IL-10 deficient mice have normal levels of B lymphocytes and Ig in their circulation. In fact, there is evidence that IL-10 can indirectly downregulate B cell function through inhibition of the accessory cell function of monocytes. However, IL-10 appears to play a role in the growth and expansion of malignant B cells. Anti-IL-10 monoclonal antibodies and IL-10 antisense oligonucleotides have been shown to inhibit transformation of B cells by EBV in vitro. In addition, B cell lymphomas are associated with EBV and most $EBV^+$ lymphomas produce high levels of IL-10, which is derived both from the human gene and the homologue of IL-10 encoded by EBV. AIDS-related B cell lymphomas also secrete high levels of IL-10. Furthermore, patients with detectable serum IL-10 at the time of diagnosis of intermediate/high-grade non-Hodgkin's lymphoma have short survival, further suggesting a role for IL-10 in the pathogenesis of B cell malignancies.

Antagonizing IL-10 in vivo can be beneficial in several infectious and malignant diseases, and in vaccination. The effect of blocking of IL-10 is an enhancement of immune responses that is independent of the specificity of the response. This is useful in vaccinations and in the treatment of serious infectious diseases. Moreover, an IL-10 antagonist is useful in the treatment of B cell malignancies which exhibit overproduction of IL-10 and viral IL-10, and it may also be useful in boosting general anti-tumor immune response in cancer patients. Combining an IL-10 antagonist with gene therapy vectors may be useful in gene therapy of tumor cells in order to obtain maximal immune response against the tumor cells. If shuffling of IL-10 results in IL-10 with improved specific activity, this IL-10 molecule would have potential in the treatment of autoimmune diseases and inflammatory bowel diseases. IL-10 with improved specific activity may also be useful as a component of gene therapy vectors in reducing the immune response against vectors which are recognized by memory cells and it may also reduce the immunogenicity of these vectors.

An antagonist of IL-10 has been made by generating a soluble form of IL-10 receptor (sIL-1 OR; Tan et al. (1995) *J. Biol. Chem.* 270: 12906). However, sIL-10R binds IL-10 with Kd of 560 pM, whereas the wild-type, surface-bound receptor has affinity of 35-200 pM. Consequently, 150-fold molar excess of sIL-10R is required for half-maximal inhibition of biological function of IL-10. Moreover, affinity of viral IL-10 (IL-10 homologue encoded by Epstein-Barr virus) to sIL-10R is more than 1000 fold less than that of hIL-10, and in some situations, such as when treating EBV-associated B cell malignancies, it may be beneficial if one can also block the function of viral IL-10. Taken together, this soluble form of IL-10R is unlikely to be effective in antagonizing IL-10 in vivo.

To obtain an IL-10 antagonist that has sufficient affinity and antagonistic activity to function in vivo, DNA shuffling can be performed using polynucleotides that encode IL-10 receptor. IL-10 receptor with higher than normal affinity will function as an IL-10 antagonist, because it strongly reduces the amount of IL-10 available for binding to functional, wild-type IL-10R. In a preferred embodiment, IL-10R is shuffled using homologous cDNAs encoding IL-10R derived from human and other mammalian species. An alignment of human and mouse IL-10 receptor sequences is shown in FIG. 14 to illustrate the feasibility of family DNA shuffling when evolving IL-10 receptors with improved affinity. A phage library of IL-10 receptor recombinants can be screened for improved binding of shuffled IL-10R to human or viral IL-10. Wild-type IL-10 and/or viral IL-10 are added at increasing concentrations to demand for higher affinity. Phage bound to IL-10 can be recovered using anti-IL-10 monoclonal antibodies. If desired, the shuffling can be repeated one or more times, after which the evolved soluble IL-10R is analyzed in functional assays for its capacity to neutralize the biological activities of IL-10/viral IL-10. More specifically, evolved soluble IL-10R is studied for its capacity to block the inhibitory effects of IL-10 on cytokine synthesis and MHC class II expression by monocytes, proliferation by T cells, and for its capacity to inhibit the enhancing effects of IL-10 on proliferation of B cells activated by anti-CD40 monoclonal antibodies.

An IL-10 antagonist can also be generated by evolving IL-10 to obtain variants that bind to IL-10R with higher than wild-type affinity, but without receptor activation. The advantage of this approach is that one can evolve an IL-10 molecule with improved specific activity using the same methods. In a preferred embodiment, IL-10 is shuffled using homologous cDNAs encoding IL-10 derived from human and other mammalian species. In addition, a gene encoding viral IL-10 can be included in the shuffling. A library of IL-10 recombinants is screened for improved binding to human IL-10 receptor.

Library members bound to IL-10R can be recovered by anti-IL-10R monoclonal antibodies. This screening protocol is likely to result in IL-10 molecules with both antagonistic and agonistic activities. Because initial screen demands for higher affinity, a proportion of the agonists are likely to have improved specific activity when compared to wild-type human IL-10. The functional properties of the mutant IL-10 molecules are determined in biological assays similar to those described above for ultrahigh-affinity IL-10 receptors (cytokine synthesis and MHC class II expression by monocytes, proliferation of B and T cells). An antagonistic IL-4 mutant has been previously generated illustrating the general feasibility of the approach (Kruse et al. (1992) EMBO J. 11: 3237-3244). One amino acid mutation in IL-4 resulted in a molecule that efficiently binds to IL-4R α-chain but has minimal IL-4-like agonistic activity.

Another example of an IL-10 antagonist is IL-20/mda-7, which is a 206 amino acid secreted protein. This protein was originally characterized as mda-7, which is a melanoma cell-derived negative regulator of tumor cell growth (Jiang et al. (1995) Oncogene 11: 2477; (1996) Proc. Nat'l. Acad. Sci. USA 93: 9160). IL-20/mda-7 is structurally related to IL-10, and it antagonizes several functions of IL-10 (Abstract of the 13th European Immunology Meeting, Amsterdam, 22-25 Jun. 1997). In contrast to IL-10, IL-20/mda-7 enhances expression of CD80 (B7-1) and CD86 (B7-2) on human monocytes and it upregulates production of TNF-α and IL-6. IL-20/mda-7 also enhances production of IFN-γ by PHA-activated PBMC. The invention provides methods of improving genetic vaccines by incorporation of IL-20/mda-7 genes into the genetic vaccine vectors. The methods of the invention can be used to obtain IL-20/mda-7 variants that exhibit improved ability to antagonize IL-10 activity.

When a cytokine antagonist is used as a component of DNA vaccine or gene therapy vectors, maximal local effect is desirable. Therefore, in addition to a soluble form of a cytokine antagonist, a transmembrane form of the antagonist can be generated. The soluble form can be given in purified polypeptide form to patients by, for example, intravenous injection. Alternatively, a polynucleotide encoding the cytokine antagonist can be used as a component as a component of a genetic vaccine or a gene therapy vector. In this case, either or both of the soluble and transmembrane forms can be used. Where both soluble and transmembrane forms of the antagonist are encoded by the same vector, the target cells express both forms, resulting in maximal inhibition of cytokine function on the target cell surface and in their immediate vicinity.

The peptides or polypeptides obtained using these methods can substitute for the natural ligands of the receptors, such as cytokines or other costimulatory molecules in their ability to exert an effect on the immune system via the receptor. A potential disadvantage of administering cytokines or other costimulatory molecules themselves is that an autoimmune reaction could be induced against the natural molecule, either due to breaking tolerance (if using a natural cytokine or other molecule) or by inducing cross-reactive immunity (humoral or cellular) when using related but distinct molecules. Through using the methods of the invention, one can obtain agonists or antagonists that avoid these potential drawbacks. For example, one can use relatively small peptides as agonists that can mimic the activity of the natural immunomodulator, or antagonize the activity, without inducing cross-reactive immunity to the natural molecule. In a presently preferred embodiment, the optimized agonist or antagonist obtained using the methods of the invention is about 50 amino acids or length or less, more preferably about 30 amino acids or less, and most preferably is about 20 amino acids in length, or less.

The agonist or antagonist peptide is preferably at least about 4 amino acids in length, and more preferably at least about 8 amino acids in length. Polynucleotides that flank the coding sequence of the mimetic peptide can also be optimized using the methods of the invention in order to optimize the expression, conformation, or activity of the mimetic peptide.

The optimized agonist or antagonist peptides or polypeptides are obtained by generating a library of recombinant polynucleotides and screening the library to identify those that encode a peptide or polypeptide that exhibits an enhanced ability to modulate an immune response. The library can be produced using methods such as DNA shuffling or other methods described herein or otherwise known to those of skill in the art. Screening is conveniently conducted by expressing the peptides encoded by the library members on the surface of a population of replicable genetic packages and identifying those members that bind to a target of interest, e.g., a receptor.

The optimized recombinant polynucleotides that are obtained using the methods of the invention can be used in several ways. For example, the polynucleotide can be placed in a genetic vaccine vector, under the control of appropriate expression control sequences, so that the mimetic peptide is expressed upon introduction of the vector into a mammal. If desired, the polynucleotide can be placed in the vector embedded in the coding sequence of the surface protein (e.g., geneIII or geneVIII) in order to preserve the conformation of the mimetic. Alternatively, the mimetic-encoding polynucleotide can be inserted directly into the antigen-encoding sequence of the genetic vaccine to form a coding sequence for a "mimotope-on-antigen" structure. The polynucleotide that encodes the mimotope-on-antigen structure can be used within a genetic vaccine, or can be used to express a protein that is itself administered as a vaccine. As one example of this type of application, a coding sequence of a mimetic peptide is introduced into a polynucleotide that encodes the "M-loop" of the hepatitis B surface antigen (HBsAg) protein. The M-loop is a six amino acid peptide sequence bounded by cysteine residues, which is found at amino acids 139-147 (numbering within the S protein sequence). The M-loop in the natural HBsAg protein is recognized by the monoclonal antibody RFHB7 (Chen et al., Proc. Nat'l. Acad. Sci. USA, 93: 1997-2001 (1996)). According to Chen et al., the M-loop forms an epitope of the HBsAg that is non-overlapping and separate from at least four other HBsAg epitopes.

Because of the probable Cys-Cys disulfide bond in this hydrophilic part of the protein, amino acids 139-147 are likely in a cyclic conformation. This structure is therefore similar to that found in the regions of the filamentous phage proteins pIII and pVIII where mimotope sequences are placed. Therefore, one can insert a mimotope obtained using the methods of the invention into this region of the HBsAg amino acid sequence.

The chemokine receptor CCR6 is an example of a suitable target for a peptide mimetic obtained using the methods. The CCR6 receptor is a 7-transmembrane domain protein (Dieu et al., Biochem. Biophys. Res. Comm. 236: 212-217 (1997) and J. Biol. Chem. 272: 14893-14898 (1997)) that is involved in the chemoattraction of immature dendritic cells, which are found in the blood and migrate to sites of antigen uptake (Dieu et al., J. Exp. Med. 188: 373-386 (1998)). CCR6 binds the chemokine MIP-3α, so a mimetic peptide that is capable of activating CCR6 can provide a further chemoattractant function to a given antigen and thus promote uptake by dendritic cells after immunization with the antigen antigen-mimetic fusion or a DNA vector that expresses the antigen.

Another application of this, method of the invention is to obtain molecules that can act as an agonist for the macrophage scavenger receptor (MSR; see, Wloch et al., *Hum. Gene Ther.* 9: 1439-1447 (1998)). The MSR is involved in mediating the effects of various immunomodulators. Among these are bacterial DNA, including the plasmids used in DNA vaccination, and oligonucleotides, which are often potent immunostimulators. Oligonucleotides of certain chemical structure (e.g., phosphothio-oligonucleotides) are particularly potent, while bacterial or plasmid DNA must be used in relatively large quantities to produce an effect. Also mediated by the MSR is the ability of oligonucleotides that contain dG residues to stimulate B cells and enhance the activity of immunostimulatory CpG motifs, and of lipopolysaccharides to activate macrophages. Some of these activities are toxic. Each of these immunomodulators, along with a variety of polyanionic ligands, binds to the MSR. The methods of the invention can be used to obtain mimetics of one or more of these immunomodulators that bind to the MSR with high affinity but are devoid of toxic properties. Such mimetic peptides are useful as immunostimulators or adjuvants.

The MSR is a trimeric integral membrane glycoprotein. The three extracellular C-terminal cysteine-rich regions are connected to the transmembrane domain by a fibrous region that is composed of an $\alpha$-helical coil and a collagen-like triple helix (see, Kodama et al., *Nature* 343: 531-535 (1990)). Therefore, screening of the library of recombinant polynucleotides can be accomplished by expressing the extracellular receptor structure and artificially attaching it to plastic surfaces. The libraries can be expressed, e.g., by phage display, and screened to identify those that bind to the receptors with high affinity. The optimized recombinant polynucleotides identified by this method can be incorporated into antigen-encoding sequences to evaluate their modulatory effect on the immune response.

4. Costimulatory Molecules Capable of Inhibiting or Enhancing Activation, Differentiation, or Anergy of Antigen-Specific T Cells Also provided are methods of obtaining optimized recombinant polynucleotides that, when expressed, are capable of inhibiting or enhancing the activation, differentiation, or anergy of antigen-specific T cells. T cell activation is initiated when T cells recognize their specific antigenic peptides in the context of MHC molecules on the plasma membrane of antigen presenting cells (APC), such as monocytes, dendritic cells (DC), Langerhans cells or B cells. Activation of $CD4^+$ T cells requires recognition by the T cell receptor (TCR) of an antigenic peptide in the context of MHC class II molecules, whereas $CD8^+$ T cells recognize peptides in the context of MHC class I molecules. Importantly, however, recognition of the antigenic peptides is not sufficient for induction of T cell proliferation and cytokine synthesis. An additional costimulatory signal, "the second signal", is required. The costimulatory signal is mediated via CD28, which binds to its ligands B7-1 (CD80) or B7-2 (CD86), typically expressed on the antigen presenting cells. In the absence of the costimulatory signal, no T cell activation occurs, or T cells are rendered anergic. In addition to CD28, CTLA-4 (CD152) also functions as a ligand for B7-1 and B7-2. However, in contrast to CD28, CTLA-4 mediates a negative regulatory signal to T cells and/or to induce anergy and tolerance (Walunas et al. (1994) *Immunity* 1: 405; Karandikar et al. (1996) *J. Exp. Med.* 184: 783).

B7-1 and B7-2 have been shown to be able to regulate several immunological responses, and they have been implicated to be of importance in the immune regulation in vaccinations, allergy, autoimmunity and cancer. Gene therapy and genetic vaccine vectors expressing B7-1 and/or B7-2 have also been shown to have therapeutic potential in the treatment of the above mentioned diseases and in improving the efficacy of genetic vaccines.

Figure 10:
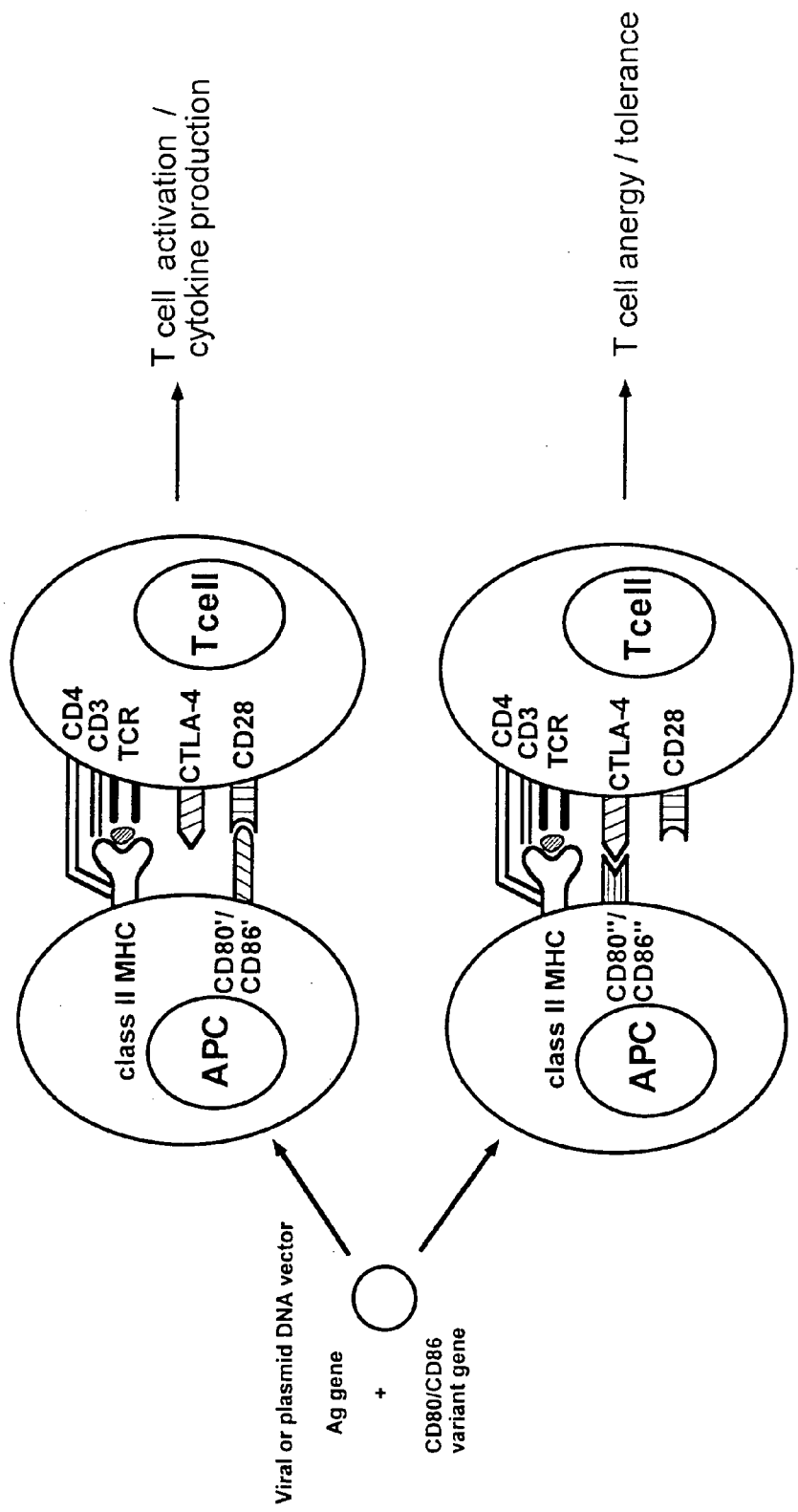

FIG. 10 illustrates interaction of APC and $CD4^+$ T cells, but the same principle is true with $CD8^+$ T cells, with the exception that the T cells recognize the antigenic peptides in the context of MHC class I molecules. Both B7-1 and B7-2 bind to CD28 and CTLA-4, even though the sequence similarities between these four molecules are very limited (20-30%). It is desirable to obtain mutations in B7-1 and B7-2 that only influence binding to one ligand but not to the other, or improve activity through one ligand while decreasing the activity through the other. Moreover, because the affinities of B7 molecules to their ligands appear to be relatively low, it would also be desirable to find mutations that improve/alter the activities of the molecules. However, rational design does not enable predictions of useful mutations because of the complexity of the molecules.

The invention provides methods of overcoming these difficulties, enabling one to generate and identify functionally different B7 molecules with altered relative capacities to induce T cell activation, differentiation, cytokine production, anergy and/or tolerance. Through use of the methods of the invention, one can find mutations in B7-1 and B7-2 that only influence binding to one ligand but not to the other, or that improve activity through one ligand while decreasing the activity through the other. DNA shuffling is likely to be the most powerful method in discovering new B7 variants with altered relative binding capacities to CD28 and CTLA-4. B7 variants which act through CD28 with improved activity (and with decreased activity through CTLA-4) are expected to have improved capacity to induce activation of T cells. In contrast, B7 variants which bind and act through CTLA-4 with improved activity (and with decreased activity through CD28) are expected to be potent negative regulators of T cell functions and to induce tolerance and anergy.

DNA shuffling or other recombination method is used to generate B7 (e.g., B7-1/CD80 and B7-2/CD86) variants which have altered relative capacity to act through CD28 and CTLA-4 when compared to wild-type B7 molecules. In a preferred embodiment, the different forms of substrate used in the recombination reaction are B7 cDNAs from various species. Such cDNAs can be obtained by methods known to those of skill in the art, including RT-PCR.

Figure 11:
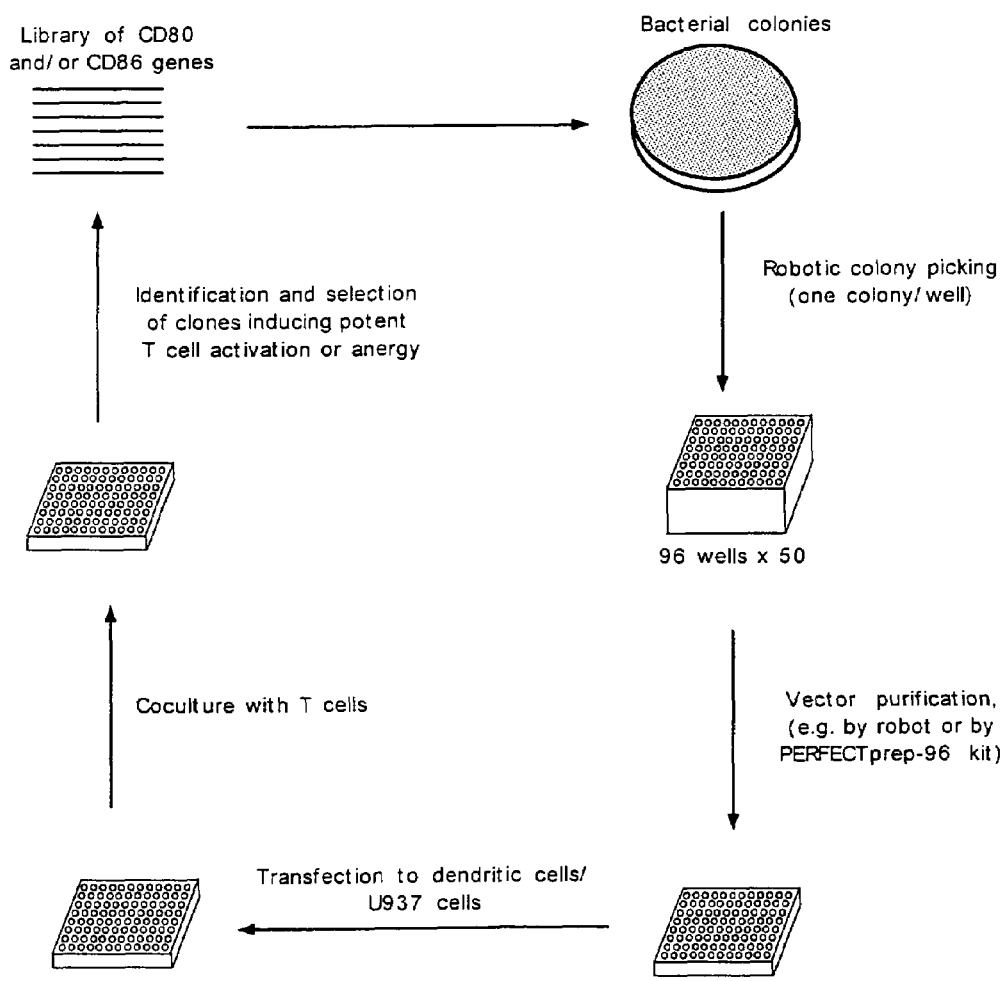
Figure 12:
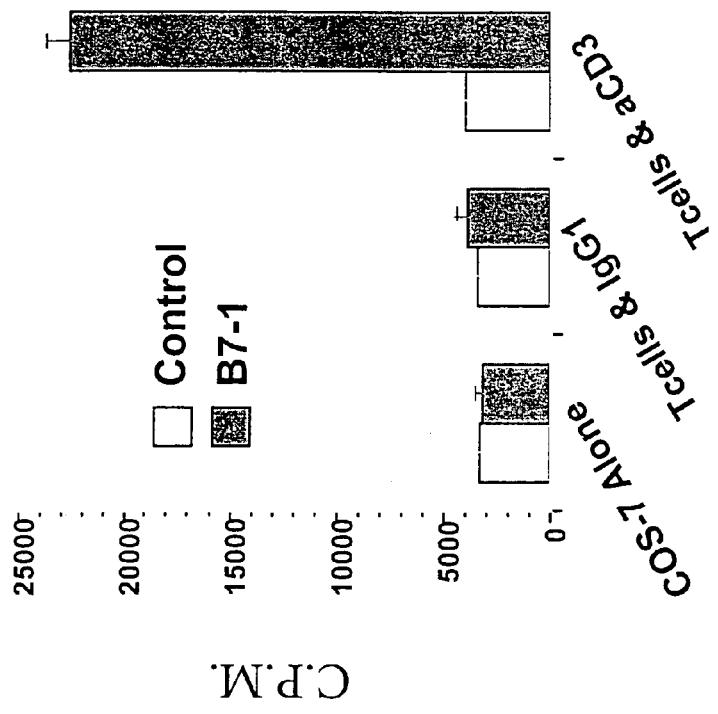

Typically, genes encoding these variant B7 molecules are incorporated into genetic vaccine vectors encoding an antigen, so that one the vectors can be used to modify antigen-specific T cell responses. Vectors that harbor B7 genes that efficiently act through CD28 are useful in inducing, for example, protective immune responses, whereas vectors that harbor genes encoding B7 genes that efficiently act through CTLA-4 are useful in inducing, for example, tolerance and anergy of allergen- or autoantigen-specific T cells. In some situations, such as in tumor cells or cells inducing autoimmune reactions, the antigen may already be present on the surface of the target cell, and the variant B7 molecules may be transfected in the absence of additional exogenous antigen gene. FIG. 11 illustrates a screening protocol that one can use to identify B7-1 (CD80) and/or B7-2 (CD86) variants that have increased capacity to induce T cell activation or anergy, and the application of this strategy is described in more detail in Example 1.

Several approaches for screening of the variants can be taken. For example, one can use a flow cytometry-based selection systems. The library of B7-1 and B7-2 molecules is transfected into cells that normally do not express these molecules (e.g., COS-7 cells or any cell line from a different species with limited or no cross-reactivity with man regarding B7 ligand binding). An internal marker gene can be incorporated in order to analyze the copy number per cell. Soluble CTLA-4 and CD28 molecules can be generated to for use in the flow cytometry experiments. Typically, these will be fused with the Fc portion of IgG molecule to improve the stability of the molecules and to enable easy staining by labeled anti-IgG mAbs, as described by van der Merwe et al. (J. Exp. Med. 185: 393, 1997). The cells transfected with the library of B7 molecules are then stained with the soluble CTLA-4 and CD28 molecules. Cells demonstrating increased or decreased CTLA-4/CD28 binding ratio will be sorted. The plasmids are then recovered and the shuffled B7 variant-encoding sequences identified. These selected B7 variants can then be subjected to new rounds of shuffling and selection, and/or they can be further analyzed using functional assays as described below.

The B7 variants can also be directly selected based on their functional properties. For in vivo studies, the B7 molecules can also be evolved to function on mouse cells. Bacterial colonies with plasmids with mutant B7 molecules are picked and the plasmids are isolated. These plasmids are then transfected into antigen presenting cells, such as dendritic cells, and the capacities of these mutants to activate T cells is analyzed. One of the advantages of this approach is that no assumptions on the binding affinities or specificities to the known ligands are made, and possibly new activities through yet to be identified ligands can be found. In addition to dendritic cells, other cells that are relatively easy to transfect (e.g., U937 or COS-7) can be used in the screening, provided that the "first T cell signal" is induced by, for example, anti-CD3 monoclonal antibodies. T cell activation can be analyzed by methods known to those of skill in the art, including, for example, measuring proliferation, cytokine production, CTL activity or expression of activation antigens such as IL-2 receptor, CD69 or HLA-DR molecules. Usage of antigen-specific T cell clones, such as T cells specific for house dust mite antigen Der p I, will allow analysis of antigen-specific T cell activation (Yssel et al. (1992) *J. Immunol.* 148: 738-745). Mutants are identified that can enhance or inhibit T cell proliferation or enhance or inhibit CTL responses. Similarly variants that have altered capacity to induce cytokine production or expression of activation antigens as measured by, for example, cytokine-specific ELISAs or flow cytometry can be identified.

The B7 variants are useful in modulating immune responses in autoimmune diseases, allergy, cancer, infectious disease and vaccination. B7 variants which act through CD28 with improved activity (and with decreased activity through CTLA-4) will have improved capacity to induce activation of T cells. In contrast, B7 variants which bind and act through CTLA-4 with improved activity (and with decreased activity through CD28) will be potent negative regulators of T cell functions and to induce tolerance and anergy. Thus, by incorporating genes encoding these variant B7 molecules into genetic vaccine vectors encoding an antigen, it is possible to modify antigen-specific T cell responses. Vectors that harbor B7 genes that efficiently act through CD28 are useful in inducing, for example, protective immune responses, whereas vectors that harbor genes encoding B7 genes that efficiently act through CTLA-4 are useful in inducing, for example, tolerance and anergy of allergen- or autoantigen-specific T cells. In some situations, such as in tumor cells or cells inducing autoimmune reactions, the antigen may already be present on the surface of the target cell, and the variant B7 molecules may be transfected in the absence of additional exogenous antigen gene.

The methods of the invention are also useful for obtaining B7 variants that have increased effectiveness in directing either $T_H1$ or $T_H2$ cell differentiation. Differential roles have been observed for B7-1 and B7-2 molecules in the regulation of T helper ($T_H$) cell differentiation (Freeman et al. (1995) *Immunity* 2: 523; Kuchroo et al. (1995) *Cell* 80: 707). $T_H$ cell differentiation can be measured by analyzing the cytokine production profiles induced by each particular variant. High levels of IL-4, IL-5 and/or IL-13 are an indication of efficient $T_H2$ cell differentiation whereas high levels of IFN-γ or IL-2 production can be used as a marker of $T_H1$ cell differentiation. B7 variants with altered capacity to induce $T_H1$ or $T_H2$ cell differentiation are useful, for example, in the treatment of allergic, malignant, autoimmune and infectious diseases and in vaccination.

Also provided by the invention are methods of obtaining B7 variants that have enhanced capacity to induce IL-10 production by antigen-specific T cells. Elevated production of IL-10 is a characteristic of regulatory T cells, which can suppress proliferation of antigen-specific CD4+ T cells (Groux et al. (1997) *Nature* 389: 737). DNA shuffling is performed as described above, after which recombinant nucleic acids encoding B7 variants having enhanced capability of inducing IL-10 can be identified by, for example, ELISA or flow cytometry using intracytoplasmic cytokine staining. The variants that induce high levels of IL-10 production are useful in the treatment of allergic and autoimmune diseases.

D. Optimization of Transport and Presentation of Antigens

The invention also provides methods of obtaining genetic vaccines and accessory molecules that can improve the transport and presentation of antigenic peptides. A library of recombinant polynucleotides is created and screened to identify those that encode molecules that have improved properties compared to the wild-type counterparts. The polynucleotides themselves can be used in genetic vaccines, or the gene products of the polynucleotides can be utilized for therapeutic or prophylactic applications.

1. Proteasomes

The class I peptides presented on major histocompatibility complex molecules are generated by cellular proteasomes. Interferon-gamma can stimulate antigen presentation, and part of the mechanism of action of interferon may be due to induction of the proteasome beta-subunits LMP2 and LMP7, which replace the homologous beta-subunits Y (delta) and X (epsilon). Such a replacement changes the peptide cleavage specificity of the proteasome and can enhance class I epitope immunogenicity. The Y (delta) and X (epsilon) subunits, as well as other recently discovered proteasome subunits such as the MECL-1 homologue MC14, are characteristic of cells which are not specialized in antigen presentation. Thus, the incorporation into cells by DNA transfer of LMP2, LMP7, MECL-1 and/or other epitope presentation-specific and potentially interferon-inducible subunits can enhance epitope presentation. It is likely that the peptides generated by the proteasome containing the interferon-inducible subunits are transported to the endoplasmic reticulum by the TAP molecules.

The invention provides methods of obtaining proteasomes that exhibit increased or decreased ability to specifically process MHC class I epitopes. According to the methods, DNA shuffling is used to obtain evolved proteins that can either have new specificities which might enhance the immunogenicity of some proteins and/or enhance the activity of the subunits once they are bound to the proteasome. Because the transition from a non-specific proteasome to a class I epitope-specific proteasome can pass through several states (in which some but not all of the interferon-inducible subunits are associated with the proteasome), many different proteolytic specificities can potentially be achieved. Evolving the specific LMP-like subunits can therefore create new proteasome compositions which have enhanced functionality for the presentation of epitopes.

The methods involve performing DNA shuffling using as substrates two or more forms of polynucleotides which encode proteasome components, where the forms of polynucleotides differ in at least one nucleotide. Shuffling is performed as described herein, using polynucleotides that encode any one or more of the various proteasome components, including, for example, LMP2, LMP7, MECL-1 and other individual proteasome components that are specifically involved in class I epitope presentation. Examples of suitable substrates are described in, e.g., Stohwasser et al. (1997) *Eur. J. Immunol.* 27: 1182-1187 and Gaczynska et al. (1996) *J. Biol. Chem.* 271: 17275-17280. In a preferred embodiment, family shuffling is used, in which the different substrates are proteasome component-encoding polynucleotides from different species.

After the recombination reaction is completed, the resulting library of recombinant polynucleotides is screened to identify those which encode proteasome components having the desired effect on class I epitope production. For example, the recombinant polynucleotides can be introduced into a genetic vaccine vector which also encodes a particular antigen of interest. The library of vectors can then be introduced into mammalian cells which are then screened to identify cells which exhibit increased antigen-specific immunogenicity. Methods of analyzing proteasome activity are described in, for example, Groettrup et al. (1997) *Proc. Nat.'l. Acad. Sci. USA* 94: 8970-8975 and Groettrup et al. (1997) *Eur. J. Immunol.* 26: 863-869.

Alternatively, one can use the methods of the invention to evolve proteins which bind strongly to the proteasome but have decreased or no activity, thus antagonizing the proteasome activity and diminishing a cells ability to present class I molecules. Such molecules can be applied to gene therapy protocols in which it is desirable to lower the immunogenicity of exogenous proteins expressed in the cells as a result of the gene therapy, and which would otherwise be processed for class I presentation allowing the cell to be recognized by the immune system. Such high-affinity low-activity LMP-like subunits will demonstrate immunosuppressive effects which are also of use in other therapeutic protocols where cells expressing a non-self protein need to be protected from an immune response.

The specificity of the proteasome and the TAP molecules (discussed below) may have co-evolved naturally. Thus it may be important that the two pathways of the class I processing system be functionally matched. A further aspect of the invention involves performing DNA shuffling simultaneously on the two gene families followed by random combinations of the two in order to discover appropriate matched proteolytic and transport specificities.

2. Antigen Transport

The invention provides methods of improving transport of antigenic peptides from the cytosolic compartment to the endoplasmic reticulum and thereby to the cell surface in the context of MHC class I molecules. Enhanced expression of antigenic peptides results in enhanced immune response, particularly in improved activation of $CD8^+$ cytotoxic lymphocytes. This is useful in the development of DNA vaccines and in gene therapy.

In one embodiment, the invention involves evolving TAP-genes (transporters associated with antigen processing) to obtain genes that exhibit improved antigen presentation. TAP genes are members of ATP-binding cassette family of membrane translocators. These proteins transport antigenic peptides to MHC class I molecules and are involved in the expression and stability of MHC class I molecules on the cell surface. Two TAP genes, TAP1 and TAP2, have been cloned to date (Powis et al. (1996) *Proc. Nat'l. Acad. Sci. USA* 89: 1463-1467; Koopman et al. (1997) *Curr. Opin. Immunol.* 9: 80-88; Monaco (1995) *J. Leukocyte Biol.* 57: 543-57). TAP1 and TAP2 form a heterodimer and these genes are required for transport of peptides into the endoplasmic reticulum, where they bind to MHC class I molecules. The essential role of TAP gene products in presentation of antigenic peptides was demonstrated in mice with disrupted TAP genes. TAP1-deficient mice have drastically reduced levels of surface expression of MHC class I, and positive selection of $CD8^+$ T cells in the thymus is strongly reduced. Therefore, the number of $CD8^+$ T lymphocytes in the periphery of TAP-deficient mice is extremely low. Transfection of TAP genes back into these cells restores the level of MHC class I expression.

TAP genes are a good target for gene shuffling because of natural polymorphism and because these genes of several mammalian species have been cloned and sequenced, including human (Beck et al. (1992) *J. Mol. Biol.* 228: 433-441; Genbank Accession No. Y13582; Powis et al., supra.), gorilla TAP1 (Laud et al. (1996) *Human Immunol.* 50: 91-102), mouse (Reiser et al. (1988) Proc. Nat'l. Acad. Sci. USA 85: 2255-2259; Marusina et al. (1997) *J. Immuno* 158: 5251-5256, TAP1: Genbank Accession Nos. U60018, U60019, U60020, U60021, U60022, and L76468-L67470; TAP2: Genbank Accession Nos. U60087, U60088, U6089, U60090, U60091 and U60092), hamster (TAP1, Genbank Accession Nos. AF001154 and AF001157; TAP2, Genbank Accession Nos. AF001156 and AF001155). Furthermore, it has been shown that point mutations in TAP genes may result in altered peptide specificity and peptide presentation. Also, functional differences in TAP genes derived from different species have been observed. For example, human TAP and rat TAP containing the rTAP2a allele are rather promiscuous, whereas mouse TAP is restrictive and select against peptides with C-terminal small polar/hydrophobic or positively charged amino acids. The basis for this selectivity is unknown.

The methods of the invention involve performing DNA shuffling of TAP1 and TAP2 genes using as substrates at least two forms of TAP1 and/or TAP2 polynucleotide sequences which differ in at least one nucleotide position. In a preferred embodiment, TAP sequences derived from several mammalian species are used as the substrates for shuffling. Natural polymorphism of the genes can provide additional diversity of substrate. If desired, optimized TAP genes obtained from one round of shuffling and screening can be subjected to additional shuffling/screening rounds to obtain further optimized TAP-encoding polynucleotides.

To identify optimized TAP-encoding polynucleotides from a library of recombinant TAP genes, the genes can be expressed on the same plasmid as a target antigen of interest. If this step is limiting the extent of antigen presentation, then enhanced presentation to $CD8^+$ CTL will result. Mutants of TAPs may act selectively to increase expression of a particular antigen peptide fragment for which levels of expression are otherwise limiting, or to cause transport of a peptide that would normally never be transferred into the RER and made available to bind to MHC Class I.

When used in the context of gene therapy vectors in cancer treatment, evolved TAP genes provide a means to enhance expression of MHC class I molecules on tumor cells and obtain efficient presentation of antigenic tumor-specific peptides. Thus, vectors that contain the evolved TAP genes can induce potent immune responses against the malignant cells. Shuffled TAP genes can be transfected into malignant cell lines that express low levels of MHC class I molecules using retroviral vectors or electroporation. Transfection efficiency can be monitored using marker genes, such as green fluorescent protein, encoded by the same vector as the TAP genes. Cells expressing equal levels of green fluorescent protein but the highest levels of MHC class I molecules, as a marker of efficient TAP genes, are then sorted using flow cytometry, and the evolved TAP genes are then recovered from these cells by, for example, PCR or by recovering the entire vectors. These sequences can then subjected into new rounds of shuffling, selection and recovery, if further optimization is desired.

Molecular evolution of TAP genes can be combined with simultaneous evolution of the desired antigen. Simultaneous evolution of the desired antigen can further improve the efficacy of presentation of antigenic peptides following DNA vaccination. The antigen can be evolved, using gene shuffling, to contain structures that allow optimal presentation of desired antigenic peptides when optimal TAP genes are expressed. TAP genes that are optimal for presentation of antigenic peptides of one given antigen may be different from TAP genes that are optimal for presentation of antigenic peptide of another antigen. Gene shuffling technique is ideal, and perhaps the only, method to solve this type of problems. Efficient presentation of desired antigenic peptides can be analyzed using specific cytotoxic T lymphocytes, for example, by measuring the cytokine production or CTL activity of the T lymphocytes using methods known to those of skill in the art.

3. Cytotoxic T-Cell Inducing Sequences And Immunogenic Agonist Sequences

Certain proteins are better able than others to carry MHC class I epitopes because they are more readily used by the cellular machinery involved in the necessary processing for class I epitope presentation. The invention provides methods of identifying expressed polypeptides that are particularly efficient in traversing the various biosynthetic and degradative steps leading to class I epitope presentation and the use of these polypeptides to enhance presentation of CTL epitopes from other proteins.

In one embodiment, the invention provides Cytotoxic T-cell Inducing Sequences (CTIS), which can be used to carry heterologous class I epitopes for the purpose of vaccinating against the pathogen from which the heterologous epitopes are derived. One example of a CTIS is obtained from the hepatitis B surface antigen (HBsAg), which has been shown to be an effective carrier for its own CTL epitopes when delivered as a protein under certain conditions. DNA immunization with plasmids expressing the HBsAg also induces high levels of CTL activity. The invention provides a shorter, truncated fragment of the HBsAg polypeptide which functions very efficiently in inducing CTL activity, and attains CTL induction levels that are higher than with the HBsAg protein or with the plasmids encoding the full-length HBsAg polypeptide. Synthesis of a CTIS derived from HBsAg is described in Example 3; and a diagram of a CTIS is shown in FIG. 1.

The ER localization of the truncated polypeptide may be important in achieving suitable proteolytic liberation of the peptide(s) containing the CTL epitopes (see Cresswell & Hughes (1997) *Curr. Biol.* 7: R552—R555; Craiu et al. (1997) *Proc. Nat'l. Acad. Sci. USA* 94: 10850-10855). The preS2 region and the transmembrane region provide T-helper epitopes which may be important for the induction of a strong cytotoxic immune response. Because the truncated CTIS polypeptide has a simple structure (see FIG. 1), it is possible to attach one or more heterologous class I epitope sequences to the C-terminal end of the polypeptide without having to maintain any specific protein conformation. Such sequences are then available to the class I epitope processing mechanisms. The size of the polypeptide is not subject to the normal constraints of the native HBsAg structure. Therefore the length of the heterologous sequence and thus the number of included CTL epitopes is flexible. This is shown schematically in FIG. 2. The ability to include a long sequence containing either multiple and distinct class I sequences, or alternatively different variations of a single CTL sequence, allows DNA shuffling methodology to be applied.

The invention also provides methods of obtaining Immunogenic Agonist Sequences (IAS) which induce CTLs capable of specific lysis of cells expressing the natural epitope sequence. In some cases, the reactivity is greater than if the CTL response is induced by the natural epitope (see, Example 3 and FIG. 3). Such IAS-induced CTL may be drawn from a T-cell repertoire different from that induced by the natural sequence. In this way, poor responsiveness to a given epitope can be overcome by recruiting T cells from a larger pool. In order to discover such IAS, the amino acid at each position of a CTL-inducing peptide (excluding perhaps the positions of the so-called anchor residues) can be varied over the range of the 19 amino acids not normally present at the position. DNA shuffling methodology can be used to scan a large range of sequence possibilities.

A synthetic gene segment containing multiple copies of the original epitope sequence can be prepared such that each copy possesses a small number of nucleotide changes. The gene segment can be shuffled to create a diverse range of CTL epitope sequences, some of which should function as IAS. This process is illustrated in FIG. 4.

In practice, oligonucleotides are typically constructed in accordance with the above design and polymerized enzymatically to form the synthetic gene segment of the concatenated epitopes. Restriction sites can be incorporated into a fraction of the oligonucleotides to allow for cleavage and selection of given size ranges of the concatenated epitopes, most of which will have different sequences and thus will be potential IAS. The epitope-containing gene segment can be joined by appropriate cloning methods to a CTIS, such as that of HBsAg. The resulting plasmid constructions can be used for DNA-based immunization and CTL induction.

E. Genetic Vaccine Pharmaceutical Compositions and Methods of Administration

The improved immunomodulatory polynucleotides and polypeptides of the invention are useful for treating and/or preventing the various diseases and conditions with which the respective antigens are associated. For example, genetic vaccines that employ the reagents obtained according to the methods of the invention are useful in both prophylaxis and therapy of infectious diseases, including those caused by any bacterial, fungal, viral, or other pathogens of mammals. The reagents obtained using the invention can also be used for treatment of autoimmune diseases including, for example, rheumatoid arthritis, SLE, diabetes mellitus, myasthenia gravis, reactive arthritis, ankylosing spondylitis, and multiple sclerosis. These and other inflammatory conditions, including IBD, psoriasis, pancreatitis, and various immunodeficiencies, can be treated using genetic vaccines that include vectors and other components obtained using the methods of the invention. Genetic vaccine vectors and other reagents obtained using the methods of the invention can be used to treat allergies and asthma. Moreover, the use of genetic vaccines have great promise for the treatment of cancer and prevention of metastasis. By inducing an immune response against cancerous cells, the body's immune system can be enlisted to reduce or eliminate cancer.

In presently preferred embodiments, the reagents obtained using the invention are used in conjunction with a genetic vaccine vector. The choice of vector and components can also be optimized for the particular purpose of treating allergy or other conditions. For example, an antigen associated with treating a particular condition can be optimized using recombination and selection methods analogous to those described herein. Such methods, and antigens appropriate for various conditions, are described in copending, commonly assigned U.S. patent application Ser. No. 09/247,890, now U.S. Pat. No. 6,541,011, entitled "Antigen Library Immunization," which was filed on Feb. 10, 1999. The polynucleotide that encodes the recombinant antigenic polypeptide can be placed under the control of a promoter, e.g., a high activity or tissue-specific promoter. The promoter used to express the antigenic polypeptide can itself be optimized using recombination and selection methods analogous to those described herein, as described in International Application No. PCT/US97/17300 (International Publication No. WO 98/13487). The reagents obtained using the methods of the invention can also be used in conjunction with multicomponent genetic vaccines, which are capable of tailoring an immune response as is most appropriate to achieve a desired effect (see, e.g., copending, commonly assigned U.S. patent application Ser. No. 09/247,888, now abandoned, entitled "Genetic Vaccine Vector Engineering," filed on Feb. 10, 1999. It is sometimes advantageous to employ a genetic vaccine that is targeted for a particular target cell type (e.g., an antigen presenting cell or an antigen processing cell); suitable targeting methods are described in copending, commonly assigned U.S. patent application Ser. No. 09/247,886 entitled "Targeting of Genetic Vaccine Vectors," filed on Feb. 10, 1999.

Genetic vaccine vectors that include the optimized recombinant polynucleotides obtained as described herein can be delivered to a mammal (including humans) to induce a therapeutic or prophylactic immune response. Vaccine delivery vehicles can be delivered in vivo by administration to an individual patient, typically by systemic administration (e.g., intravenous, intraperitoneal, intramuscular, subdermal, intracranial, anal, vaginal, oral, buccal route or they can be inhaled) or they can be administered by topical application. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

A large number of delivery methods are well known to those of skill in the art. Such methods include, for example liposome-based gene delivery (Debs and Zhu (1993) WO 93/24640; Mannino and Gould-Fogerite (1988) *BioTechniques* 6(7): 682-691; Rose U.S. Pat. No. 5,279,833; Brigham (1991) WO 91/06309; and Felgner et al. (1987) *Proc. Natl. Acad. Sci. USA* 84: 7413-7414), as well as use of viral vectors (e.g., adenoviral (see, e.g., Berns et al. (1995) Ann. NY Acad. Sci. 772: 95-104; Ali et al. (1994) *Gene Ther.* 1: 367-384; and Haddada et al. (1995) *Curr. Top. Microbiol. Immunol.* 199 (Pt 3): 297-306 for review), papillomaviral; retroviral (see, e.g., Buchscher et al. (1992) *J. Virol.* 66(5) 2731-2739; Johann et al. (1992) *J. Virol.* 66 (5):1635-1640 (1992); Sommerfelt et al., (1990) *Virol.* 176:58-59; Wilson et al. (1989) *J. Virol.* 63:2374-2378; Miller et al., *J. Virol.* 65:2220-2224 (1991); Wong-Staal et al., PCT/US94/05700, and Rosenburg and Fauci (1993) in *Fundamental Immunology, Third Edition* Paul (ed) Raven Press, Ltd., New York and the references therein, and Yu et al., *Gene Therapy* (1994) supra.), and adeno-associated viral vectors (see, West et al. (1987) *Virology* 160:38-47; Carter et al. (1989) U.S. Pat. No. 4,797,368; Carter et al. WO 93/24641 (1993); Kotin (1994) *Human Gene Therapy* 5:793-801; Muzyczka (1994) *J. Clin. Invst.* 94:1351 and Samulski (supra) for an overview of AAV vectors; see also, Lebkowski, U.S. Pat. No. 5,173,414; Tratschin et al. (1985) *Mol. Cell. Biol.* 5(11):3251-3260; Tratschin, et al. (1984) *Mol. Cell. Biol.*, 4:2072-2081; Hermonat and Muzyczka (1984) *Proc. Natl. Acad. Sci. USA*, 81:6466-6470; McLaughlin et al. (1988) and Samulski et al. (1989) *J. Virol.*, 63:03822-3828), and the like.

"Naked" DNA and/or RNA that comprises a genetic vaccine can be introduced directly into a tissue, such as muscle. See, e.g., U.S. Pat. No. 5,580,859. Other methods such as "biolistic" or particle-mediated transformation (see, e.g., Sanford et al., U.S. Pat. No. 4,945,050; U.S. Pat. No. 5,036,006) are also suitable for introduction of genetic vaccines into cells of a mammal according to the invention. These methods are useful not only for in vivo introduction of DNA into a mammal, but also for ex vivo modification of cells for reintroduction into a mammal. As for other methods of delivering genetic vaccines, if necessary, vaccine administration is repeated in order to maintain the desired level of immunomodulation.

Genetic vaccine vectors (e.g., adenoviruses, liposomes, papillomaviruses, retroviruses, etc.) can be administered directly to the mammal for transduction of cells in vivo. The genetic vaccines obtained using the methods of the invention can be formulated as pharmaceutical compositions for administration in any suitable manner, including parenteral (e.g., subcutaneous, intramuscular, intradermal, or intravenous), topical, oral, rectal, intrathecal, buccal (e.g., sublingual), or local administration, such as by aerosol or transdermally, for prophylactic and/or therapeutic treatment. Pretreatment of skin, for example, by use of hair-removing agents, may be useful in transdermal delivery. Suitable methods of administering such packaged nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of genetic vaccine vector in these formulations can vary widely, and will be selected primarily based on fluid volumes, viscosities, body weight and the like in accordance with the particular mode of administration selected and the patient's needs.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art. It is recognized that the genetic vaccines, when administered orally, must be protected from digestion. This is typically accomplished either by complexing the vaccine vector with a composition to render it resistant to acidic and enzymatic hydrolysis or by packaging the vector in an appropriately resistant carrier such as a liposome. Means of protecting vectors from digestion are well known in the art. The pharmaceutical compositions can be encapsulated, e.g., in liposomes, or in a formulation that provides for slow release of the active ingredient.

The packaged nucleic acids, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the packaged nucleic acid with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of packaged nucleic acid can be presented in unit-dose or multi-dose sealed containers, such as ampoules and vials.

Injection solutions and suspensions can be prepared from sterile powders, granules, and tablets of the kind previously described. Cells transduced by the packaged nucleic acid can also be administered intravenously or parenterally.

The dose administered to a patient, in the context of the present invention should be sufficient to effect a beneficial therapeutic response in the patient over time. The dose will be determined by the efficacy of the particular vector employed and the condition of the patient, as well as the body weight or vascular surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of an infection or other condition, the physician evaluates vector toxicities, progression of the disease, and the production of anti-vector antibodies, if any. In general, the dose equivalent of a naked nucleic acid from a vector is from about 1 µg to 1 mg for a typical 70 kilogram patient, and doses of vectors used to deliver the nucleic acid are calculated to yield an equivalent amount of therapeutic nucleic acid. Administration can be accomplished via single or divided doses.

In therapeutic applications, compositions are administered to a patient suffering from a disease (e.g., an infectious disease or autoimmune disorder) in an amount sufficient to cure or at least partially arrest the disease and its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the proteins of this invention to effectively treat the patient.

In prophylactic applications, compositions are administered to a human or other mammal to induce an immune response that can help protect against the establishment of an infectious disease or other condition.

The toxicity and therapeutic efficacy of the genetic vaccine vectors provided by the invention are determined using standard pharmaceutical procedures in cell cultures or experimental animals. One can determine the $LD_{50}$ (the dose lethal to ~50% of the population) and the $ED_{50}$ (the dose therapeutically effective in 50% of the population) using procedures presented herein and those otherwise known to those of skill in the art.

A typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Substantially higher dosages are possible in topical administration. Actual methods for preparing parenterally administrable compositions will be known or apparent to those skilled in the art and are described in more detail in such publications as *Remington's Pharmaceutical Science*, 15th ed., Mack Publishing Company, Easton, Pa. (1980).

The multivalent antigenic polypeptides of the invention, and genetic vaccines that express the polypeptides, can be packaged in packs, dispenser devices, and kits for administering genetic vaccines to a mammal. For example, packs or dispenser devices that contain one or more unit dosage forms are provided. Typically, instructions for administration of the compounds will be provided with the packaging, along with a suitable indication on the label that the compound is suitable for treatment of an indicated condition. For example, the label may state that the active compound within the packaging is useful for treating a particular infectious disease, autoimmune disorder, tumor, or for preventing or treating other diseases or conditions that are mediated by, or potentially susceptible to, a mammalian immune response.

EXAMPLES

The following examples are offered to illustrate, but not to limit the present invention.

Example 1

Altered Ligand Specificity of B7-1 (CD80) and/or B7-2 (CD86) by DNA Shuffling This Example describes the use of the DNA shuffling methods of the invention to obtain B7-1 and B7-2 polypeptides that have altered biological activities.

DNA Shuffling

DNA shuffling is used to generate a library of B7 (B7-1/CD80 and B7-2/CD86) variants that have altered relative capacity to act through CD28 and CTLA-4 when compared to wild-type B7 molecules. Typically, B7 cDNAs from various species are generated by RT-PCR, and these sequences are shuffled using family DNA shuffling. Alignments of human, rhesus monkey and rabbit B7-1 nucleotide sequences are shown in FIG. 15, demonstrating that family DNA shuffling is a feasible approach when evolving B7 molecules.

Screening of B7 Variants

The library is then screened to identify those variants that are useful in modulating immune responses in autoimmune diseases, allergy, cancer, infectious disease and vaccination. Any of several approaches for screening of the variants can be used:

A. Flow Cytometry-Based Selection System.

The library of B7-1 and B7-2 molecules is transfected into cells that normally do not express these molecules (e.g., COS-7 cells or any cell line from different species with limited or no cross-reactivity with man regarding B7 ligand binding). An internal marker gene can be incorporated in order to analyze the copy number per cell.

Soluble CTLA-4 and CD28 molecules are generated to facilitate the flow cytometry experiments. Typically, these soluble polypeptides are fused with the Fc portion of IgG molecule to improve the stability of the molecules and to enable easy staining by labeled anti-IgG monoclonal antibodies, as described by van der Merwe et al. ((1997) *J. Exp. Med.* 185: 393). The cells transfected with the library of B7 molecules are then stained with the soluble CTLA-4 and CD28 molecules. Cells demonstrating increased or decreased CTLA-4/CD28 binding ratio are sorted. The plasmids are then recovered and the shuffled sequences identified. These selected B7 variants can then be subjected to new rounds of shuffling and selection, and can be further analyzed using functional assays as described below.

B. Selection Based on Functional Properties.

Bacterial colonies that contain plasmids that include mutant B7 molecules are picked and the plasmids are isolated. These plasmids are then transfected into antigen presenting cells, such as dendritic cells, and the capacities of these mutants to activate T cells is analyzed. One of the advantages of this approach is that no assumptions are made as to the binding affinities or specificities to the known ligands, and possibly new activities through yet to be identified ligands can be found.

Figure 13:
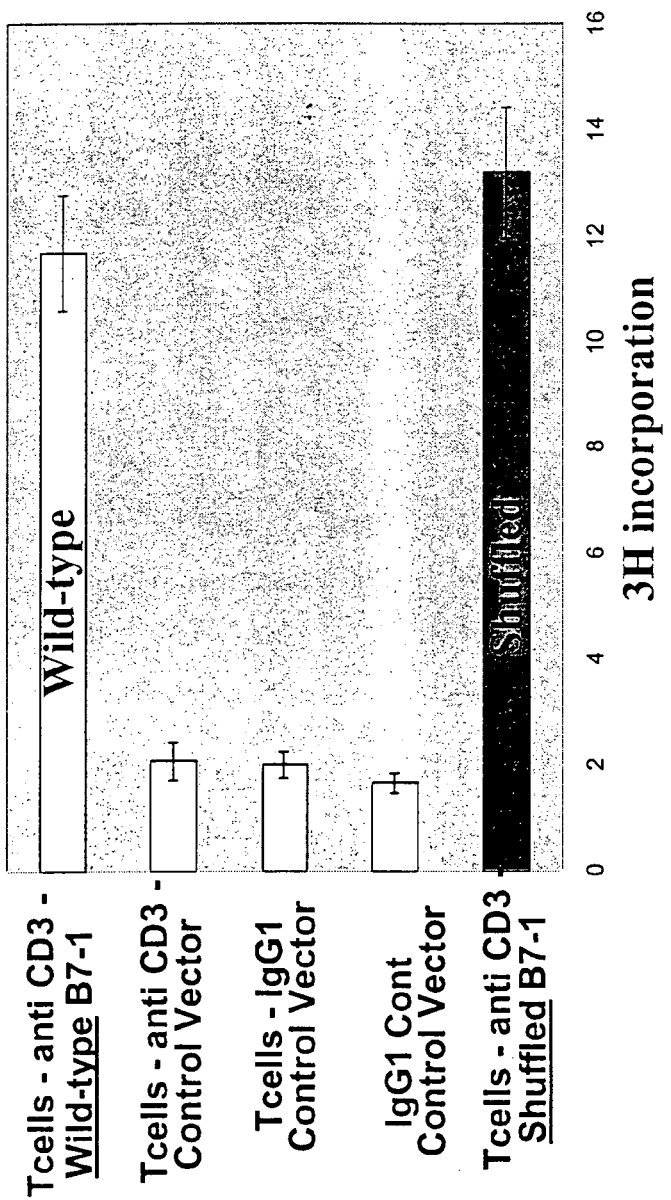

T cell activation can be analyzed by measuring proliferation, cytokine production, CTL activity or expression of activation antigens such as IL-2 receptor, CD69 or HLA-DR molecules. Usage of antigen-specific T cell clones, such as T cells specific for house dust mite antigen Der p I, allows analysis of antigen-specific T cell activation. Mutants are identified that can enhance or inhibit T cell proliferation or enhance or inhibit CTL responses. Similarly variants that have altered capacity to induce cytokine production or expression of activation antigens as measured by, for example, cytokine-specific ELISAs or flow cytometry can be selected. Results obtained using a proliferation-based assay is shown are shown in FIG. 13.

C. Ability to Direct Either $T_H1$ or $T_H2$ Cell Differentiation.

Because differential roles for B7-1 and B7-2 molecules in the regulation of T helper cell differentiation have been identified (Freeman et al. (1995) *Immunity* 2: 523; Kuchroo et al. (1995) *Cell* 80: 707), one can screen for B7 variants that are the most effective in directing either $T_H1$ or $T_H2$ cell differentiation. $T_H$ cell differentiation can be measured by analyzing the cytokine production profiles induced by each particular variant. High levels of IL-4, IL-5 and/or IL-13 are an indication of efficient $T_H2$ cell differentiation whereas high levels of IFN-γ or IL-2 production can be used as a marker of $T_H1$ cell differentiation. B7 variants that altered capacity to induce $T_H1$ or $T_H2$ cell differentiation are likely to be useful in the treatment of allergic, malignant, autoimmune and infectious diseases and in vaccination.

D. Enhanced IL-10 Production.

Elevated production of IL-10 is a characteristic of regulatory T cells, which can suppress proliferation of antigen-specific CD4$^+$ T cells (Groux et al. (1997) *Nature* 389: 0.737). Therefore, B7 variants can be screened to identify those that have enhanced capacity to induce IL-10 production by antigen-specific T cells. IL-10 production can be measured, for example, by ELISA or flow cytometry using intracytoplasmic cytokine stainings. The variants that induce high levels of IL-10 production are useful in the treatment of allergic and autoimmune diseases.

Example 2

Evolution of Cytokines for Improved Specific Activity and/or Improved Expression Levels This example describes a method to evolve a cytokine for improved specific activity and/or improved expression levels when the genetic vaccine is transfected into mammalian cells. IL-12 is the most potent cytokine directing $T_H1$ responses, and it improves the efficacy of genetic vaccinations. Evolved IL-12 molecules are useful as components of genetic vaccines. IL-12 is a heterodimeric cytokine composed of a 35 kD light chain (p35) and a 40 kD heavy chain (p40) (Kobayashi et al. (1989) *J. Exp. Med.* 170: 827; Stem et al. (1990) *Proc. Nat'l. Acad. Sci. USA* 87: 6808). Recently Lieschke et al. (*Nature Biotechnol.* (1997) 15: 35) demonstrated that a fusion between p35 and p40 genes results in a single gene that has activity comparable to that of the two genes expressed separately. Accordingly, an IL-12 gene is shuffled as one entity that encodes both subunits, which is beneficial in designing the shuffling protocol. The subunits of IL-12 can also be expressed separately in the same expression vector, or the subunits can be expressed separately and screened using cotransfections of the two vectors, providing additional shuffling strategies.

IL-12 plays several roles in the regulation of allergic responses. For example, IL-12 induces $T_H1$ cell differentiation and downregulates the $T_H2$ response. IL-12 inhibits IgE synthesis both in vivo and in vitro, and also induces IFN-γ production. Accordingly, it is desirable to obtain an optimized IL-12 that better able to carry out these functions upon administration to a mammal.

Cytokine genes, including IL-12 genes, from humans and nonhuman primates are generally 93-99% homologous (Villinger et al. (1995) *J. Immunol.* 155:3946-3954), providing a good starting point for family shuffling. A library of shuffled IL-12 genes was obtained by shuffling p35 and p40 subunits derived from human, rhesus monkey, cat, dog, cow, pig, and goat, and incorporated into vectors and the supernatants of these transfectants are analyzed for biological activity as shown in FIG. 6. Because of its T cell growth promoting activities, it is possible to use normal human peripheral blood T cells in the selection of the most active IL-12 genes, enabling directly to select IL-12 mutants with the most potent activities on human T cells.

As shown in FIG. 7, a functional screening assay has been successfully established. In this assay, COS-7 cells were first transfected with vectors encoding IL-12 subunits. Forty-eight hours after transfection, the capacity of these culture supernatants to induce proliferation of activated human peripheral blood T cells was studied. FIG. 8 indicates the consistency of the level of T cell proliferation induced in this assay, indicating that the assay can be used to distinguish the activities between supernatants that have different capacities to induce T cell activation. In other words, the assay provides means to screen for improved IL-12-like activities in culture supernatants of transfected cells. A vector with an optimized IL-12-encoding polynucleotide was tested for ability to induce human T cell activation. Results, shown in FIG. 9, show that the shuffled IL-12 has an significantly increased ability to induce T cell activation compared to wild-type IL-12.

FIG. 6 illustrates a general strategy for screening of evolved cytokine genes. The specific example is given for IL-12 but similar approach applies to all cytokines when using cell types sensitive for each cytokine. For example, GM-CSF can be evolved by the same approach by using the GM-CSF sensitive cell line TF-1 in the screening. In addition, although in this example the vectors are transfected into CHO cells, any mammalian cell that can be transfected in vitro can be used as host cells. In addition to CHO cell, other good host cells include cell lines WI-26, COS-1, COS-7, 293, U937 and freshly isolated human antigen presenting cells, such as monocytes, B cells and dendritic cells.

Example 3

Cytotoxic T-Cell Inducing Sequences Derived from Hepatitis B Surface Antigen and Strongly Immunogenic Agonistic T Cell Epitopes This Example describes the preparation of a polypeptide sequence capable of efficient presentation of T cell epitopes and a strategy for the application of DNA shuffling to discover strongly immunogenic agonistic T cell epitopes.

The HBsAg polypeptide (PreS2 plus S regions) was truncated by the introduction of a stop codon at amino acid position 103 (counting from the beginning of the PreS2 initiator methionine), transforming a cysteine codon TGT into the Stop codon TGA. The amino acid sequence of the truncated protein was therefore:

MQWNSTTFHQTLQDPRVRGLYF-PAGGSSSGTVNPVLTTASPLSSIFS-RIGDPALNMENITSGF LGPLLVLQAGFFLLTRILT-IPQSLDSWWTSLNFLGGTTV* (SEQ ID NO:6)

where the standard single-letter code for amino acids is used. The methionine residues at the start of the PreS2 and S regions are underlined, and the mouse $L^d$-restricted CTL epitope is double-underlined; the asterisk (*) represents the artificially introduced Stop codon.

A likely structure for this truncated polypeptide is shown in FIG. 1. During protein biosynthesis, the N-terminal region of the HBsAg polypeptide is transported through the membrane of the endoplasmic reticulum (ER). The first part of the S region is a transmembrane structure which locks the polypeptide into the ER. The remaining C-terminal region of the polypeptide is located in the cytoplasmic compartment where it can be accessed by the epitope processing mechanism of the cell. This structure forms what is referred to as the Cytotoxic T-cell Inducing Sequence (CTIS).

A CTIS is preferably used in conjunction with an immunogenic agonistic sequence (IAS). As an example of an IAS, each position of a 12 amino acid $L^d$-restricted class I epitope from HBsAg was replaced with an alanine-encoding codon in the DNA sequence of the epitope. The results demonstrate that, in some cases, the reactivity is greater than if the CTL response is induced by the natural epitope (FIG. 3).

Example 4

Treatment of Obesity, Anorexia, and Cachexia using Optimized Immunomodulatory Molecules Optimized immunomodulatory molecules that are obtained using the methods of the invention find use in a wide variety of applications, in addition to use in vaccination. For example, there is increasing evidence that certain forms of obesity are associated with dysfunction of the immune system, and that molecules which regulate immune responses, e.g. cytokines, can induce or inhibit obesity. The invention provides methods of optimizing immune regulatory molecules for the treatment of obesity, anorexia and cachexia.

Leptin and ciliary neurotrophic factor (CNTF) are examples of cytokines that have been shown to play a role in the development of obesity. Congenital leptin deficiency results in severe early-onset obesity in human (Montague et al. (1997) *Nature* 387: 903-908), and CNTF has been shown to correct obesity and diabetes associated with leptin deficiency and resistance (Gloaguen et al. (1997) *Proc. Nat.'l. Acad. Sci. USA* 94: 6456-6461). Antagonists of CNTF and/or leptin may be useful in the treatment of anorexia and/or cachexia.

The methods of the invention are used to generate leptin and/or CNTF molecules that have improved specific activity. The methods are also useful for obtaining improved cytokines that exhibit reduced immunogenicity in vivo; immunogenicity is a particular concern for CNTF, because the wild-type CNTF is highly antigenic, which results in the production of high levels of anti-CNTF antibodies when administered to a human. Improved cytokine molecules prepared using the methods of the invention are administered as polypeptides, or the shuffled nucleic acids that encode improved leptin and/or CNTF polypeptides are used in genetic vaccine vectors. The invention also provides methods of generating vectors that induce production of increased levels of leptin and/or CNTF.

The methods of the invention can also be used to obtain reagents that are useful for the treatment of anorexia, cachexia, and related disorders. In this embodiment, antagonists of leptin and/or CNTF are evolved using the DNA shuffling methods. For example, a leptin receptor can be evolved to obtain a soluble form that has an enhanced affinity for leptin. The receptor for leptin in mice is found in the hypothalamus (Mercer et al. (1996) *FEBS Lett.* 387: 113), a region known to be involved in maintenance of energy balance, and in the choroid plexus and leptomeninges, which form part of the blood/brain barrier.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method for obtaining an optimized immunomodulatory polynucleotide, comprising:

(a) creating a library of mutant polynucleotides from at least two nucleic acids, wherein each nucleic acid encodes a B7-1 (CD80) protein and the nucleic acids differ from each other in at least two nucleotides;

(b) introducing the library of mutant polynucleotides into a genetic vaccine vector that encodes an antigen to form a library of vectors;

(c) introducing the library of vectors into cells;

(d) expressing the library of vectors in the cells;

(e) screening the library to identify at least one optimized mutant polynucleotide encoding a mutant B7-1 protein that is a costimulator having an improved ability to activate a T cell response induced by the genetic vaccine vector and exhibiting an increased activity through CD28 and a decreased activity through CTLA-4 compared to a B7-1 protein encoded by a nucleic acid from which the library was created;

(f) recombining at least one optimized mutant polynucleotide from (e) with at least one further mutant polynucleotide from (a) to produce a further library of mutant polynucleotides;

(g) screening the further library of mutant polynucleotides of (f) to identify at least one further optimized mutant polynucleotide encoding a mutant B7-1 protein that is a costimulator having an improved ability to activate a T cell response induced by the genetic vaccine vector and exhibiting an increased activity through CD28 and a decreased activity through CTLA-4 compared to a B7-1 protein encoded by a nucleic acid from which the further library was created; and (h) repeating (f) and (g), if necessary, to identify at least one further optimized mutant polynucleotide encoding a mutant B7-1 protein that is a costimulator having an improved ability to activate a T cell response induced by the genetic vaccine vector and exhibiting an increased activity through CD28 and a decreased activity through CTLA-4 compared to a B7-1 protein encoded by a nucleic acid from which the further library was created.

2. A method for obtaining an optimized immunomodulatory polynucleotide, comprising:

(a) creating a library of mutant polynucleotides from at least two nucleic acids, wherein each nucleic acid encodes a B7-2 (CD86) protein and the nucleic acids differ from each other in at least two nucleotides;

(b) introducing the library of mutant polynucleotides into a genetic vaccine vector that encodes an antigen to form a library of vectors;

(c) introducing the library of vectors into cells;

(d) expressing the library of vectors in the cells;

(e) screening the library to identify at least one optimized mutant polynucleotide encoding a mutant B7-2 protein that is a costimulator having an improved ability to activate a T cell response induced by the genetic vaccine vector and exhibiting an increased activity through CD28 and a decreased activity through CTLA-4 compared to a B7-2 protein encoded by a nucleic acid from which the library was created;

(f) recombining at least one optimized mutant polynucleotide from (e) with at least one further mutant polynucleotide from (a) to produce a further library of mutant polynucleotides;

(g) screening the further library of mutant polynucleotides of (f) to identify at least one further optimized mutant polynucleotide encoding a mutant B7-2 protein that is a costimulator having an improved ability to activate a T cell response induced by the genetic vaccine vector and exhibiting an increased activity through CD28 and a decreased activity through CTLA-4 compared to a B7-2 protein encoded by a nucleic acid from which the further library was created; and (h) repeating (f) and (g), if necessary, to identify at least one further optimized mutant polynucleotide encoding a mutant B7-2 protein that is a costimulator having an improved ability to activate a T cell response induced by the genetic vaccine vector and exhibiting an increased activity through CD28 and a decreased activity through CTLA-4 compared to a B7-2 protein encoded by a nucleic acid from which the further library was created.

3. A method for obtaining an optimized immunomodulatory polynucleotide, comprising:
  (a) creating a library of mutant polynucleotides from at least two nucleic acids, wherein each nucleic acid encodes a B7-1 (CD80) protein and the nucleic acids differ from each other in at least two nucleotides;
  (b) introducing the library of mutant polynucleotides into cells in conjunction with a genetic vaccine vector that encodes an antigen;
  (c) expressing the antigen and the library of mutant polynucleotides in the cells;
  (d) screening the library of mutant polynucleotides to identify at least one optimized mutant polynucleotide encoding a mutant B7-1 protein that is a costimulator having an improved ability to activate a T cell response induced by the genetic vaccine vector and exhibiting an increased activity through CD28 and a decreased activity through CTLA-4 compared to a B7-1 protein encoded by a nucleic acid from which the library was created;
  (e) recombining at least one optimized mutant polynucleotide from (d) with at least one further mutant polynucleotide from (a) to produce a further library of mutant polynucleotides;
  (f) screening the further library of mutant polynucleotides of (e) to identify at least one further optimized mutant polynucleotide encoding a mutant B7-1 protein that is a costimulator having an improved ability to activate a T cell response induced by the genetic vaccine vector and exhibiting an increased activity through CD28 and a decreased activity through CTLA-4 compared to a B7-1 protein encoded by a nucleic acid from which the further library was created; and
  (g) repeating (e) and (f), if necessary, to identify at least one further optimized mutant polynucleotide encoding a mutant B7-1 protein that is a costimulator having an improved ability to activate a T cell response induced by the genetic vaccine vector and exhibiting an increased activity through CD28 and a decreased activity through CTLA-4 compared to a B7-1 protein encoded by a nucleic acid from which the further library was created.

4. A method for obtaining an optimized immunomodulatory polynucleotide, comprising:
  (a) creating a library of mutant polynucleotides from at least two nucleic acids, wherein each nucleic acid encodes a B7-2 (CD80) protein and the nucleic acids differ from each other in at least two nucleotides;
  (b) introducing the library of mutant polynucleotides into cells in conjunction with a genetic vaccine vector that encodes an antigen;
  (c) expressing the antigen and the library of mutant polynucleotides in the cells;
  (d) screening the library of mutant polynucleotides to identify at least one optimized mutant polynucleotide encoding a mutant B7-2 protein that is a costimulator having an improved ability to activate a T cell response induced by the genetic vaccine vector and exhibiting an increased activity through CD28 and a decreased activity through CTLA-4 compared to a B7-2 protein encoded by a nucleic acid from which the library was created;
  (e) recombining at least one optimized mutant polynucleotide from (d) with at least one further mutant polynucleotide from (a) to produce a further library of mutant polynucleotides;
  (f) screening the further library of mutant polynucleotides of (e) to identify at least one further optimized mutant polynucleotide encoding a mutant B7-2 protein that is a costimulator having an improved ability to activate a T cell response induced by the genetic vaccine vector and exhibiting an increased activity through CD28 and a decreased activity through CTLA-4 compared to a B7-2 protein encoded by a nucleic acid from which the further library was created; and
  (g) repeating (e) and (f), if necessary, to identify at least one further optimized mutant polynucleotide encoding a mutant B7-2 protein that is a costimulator having an improved ability to activate a T cell response induced by the genetic vaccine vector and exhibiting an increased activity through CD28 and a decreased activity through CTLA-4 compared to a B7-2 protein encoded by a nucleic acid from which the further library was created.

* * * * *

SEQUENCE LISTING

<160> NUMBER OF SEQ ID NOS: 6

<210> SEQ ID NO 1
<211> LENGTH: 3632
<212> TYPE: DNA
<213> ORGANISM: Homo sapiens
<220> FEATURE:
<223> OTHER INFORMATION: human interleukin 10 receptor (IL-10R)

<400> SEQUENCE: 1

```
aaagagctgg aggcgcgcag gccggctccg ctccggcccc ggacgatgcg gcgcgcccag      60
gatgctgccg tgcctcgtag tgctgctggc ggcgctcctc agcctccgtc ttggctcaga     120
cgctcatggg acagagctgc ccagccctcc gtctgtgtgg tttgaagcag aattttccca     180
ccacatcctc cactggacac ccatcccaaa tcagtctgaa agtacctgct atgaagtggc     240
gctcctgagg tatggaatag agtcctggaa ctccatctcc aactgtagcc agaccctgtc     300
ctatgacctt accgcagtga ccttggacct gtaccacagc aatggctacc gggccagagt     360
gcgggctgtg gacggcagcc ggcactccaa ctggaccgtc accaacaccc gcttctctgt     420
ggatgaagtg actctgacag ttggcagtgt gaacctagag atccacaatg gcttcatcct     480
cgggaagatt cagctaccca ggcccaagat ggccccgcg aatgacacat atgaaagcat     540
cttcagtcac ttccgagagt atgagattgc cattcgcaag gtgccgggaa acttcacgtt     600
cacacacaag aaagtaaaac atgaaaactt cagcctccta acctctggag aagtgggaga     660
gttctgtgtc caggtgaaac catctgtcgc ttcccgaagt aacaagggga tgtggtctaa     720
agaggagtgc atctccctca ccaggcagta tttcaccgtg accaacgtca tcatcttctt     780
tgcctttgtc ctgctgctct ccggagccct cgcctactgc ctggccctcc agctgtatgt     840
gcggcgccga aagaagctac ccagtgtcct gctcttcaag aagcccagcc ccttcatctt     900
catcagccag cgtccctccc agagaccca agacaccatc cacccgcttg atgaggaggc     960 cttttgaag gtgtccccag agctgaagaa cttggacctg cacggcagca cagacagtgg    1020
ctttggcagc accaagccat ccctgcagac tgaagagccc cagttcctcc tccctgaccc    1080
tcacccccag gctgacagaa cgctgggaaa cggggagccc cctgtgctgg gggacagctg    1140
cagtagtggc agcagcaata gcacagacag cgggatctgc ctgcaggagc ccagcctgag    1200
ccccagcaca gggcccacct gggagcaaca ggtggggagc aacagcaggg gccaggatga    1260
cagtggcatt gacttagttc aaaactctga gggccgggct ggggacacac agggtggctc    1320
ggccttgggc caccacagtc cccggagcc tgaggtgcct ggggaagaag acccagctgc    1380
tgtggcattc cagggttacc tgaggcagac cagatgtgct gaagagaagg caaccaagac    1440
aggctgcctg gaggaagaat cgccttgac agatggcctt ggccccaaat cgggagatg    1500 cctggttgat gaggcaggct tgcatccacc agccctggcc aagggctatt tgaaacagga    1560
tcctctagaa atgactctgg cttcctcagg ggcccaacg ggacagtgga accagcccac    1620
tgaggaatgg tcactcctgg ccttgagcag ctgcagtgac ctgggaatat ctgactggag    1680
cttgccccat gaccttgccc ctctaggctg tgtggcagcc ccaggtggtc tcctgggcag    1740
ctttaactca gacctggtca ccctgccct catctctagc ctgcagtcaa gtgagtgact    1800
```

-continued

```
cgggctgaga ggctgctttt gattttagcc atgcctgctc ctctgcctgg accaggagga      1860
gggccctggg gcagaagtta ggcacgaggc agtctgggca cttttctgca agtccactgg      1920
ggctggccca gccaggctgc agggctggtc agggtgtctg gggcaggagg aggccaactc      1980
actgaactag tgcagggtat gtgggtggca ctgacctgtt ctgttgactg gggccctgca      2040
gactctggca gagctgagaa gggcaggggac cttctccctc ctaggaactc tttcctgtat      2100
cataaaggat tatttgctca ggggaaccat ggggctttct ggagttgtgg tgaggccacc      2160
aggctgaagt cagctcagac ccagacctcc ctgcttaggc cactcgagca tcagagcttc      2220
cagcaggagg aagggctgta ggaatggaag cttcagggcc ttgctgctgg ggtcattttt      2280
agggaaaaaa ggaggatatg atggtcacat ggggaaccct ccctcatcgg gcctctgggg      2340
caggaagctt gtcactggaa gatcttaagg tatatatttt ctggacactc aaacacatca      2400
taatggattc actgagggga gacaaaggga gccgagaccc tggatggggc ttccagctca      2460
gaacccatcc ctctggtggg tacctctggc acccatctgc aaatatctcc ctctctccaa      2520
caaatggagt agcatccccc tggggcactt gctgaggcca agccactcac atcctcactt      2580
tgctgcccca ccatcttgct gacaacttcc agagaagcca tggttttttg tattggtcat      2640
aactcagccc tttgggcggc ctctgggctt gggcaccagc tcatgccagc cccagagggt      2700
cagggttgga ggcctgtgct tgtgtttgct gctaatgtcc agctacagac ccagaggata      2760
agccactggg cactgggctg gggtccctgc cttgttggtg ttcagctgtg tgattttgga      2820
ctagccactt gtcagagggc ctcaatctcc catctgtgaa ataaggactc cacctttagg      2880
ggaccctcca tgtttgctgg gtattagcca agctggtcct gggagaatgc agatactgtc      2940
cgtggactac caagctggct tgtttcttat gccagaggcc aacagatcca atgggagtcc      3000
atggtgtcat gccaagacag tatcagacac agccccagaa gggggcatta tgggccctgc      3060
ctccccatag gccatttgga ctctgccttc aaacaaaggc agttcagtcc acaggcatgg      3120
aagctgtgag gggacaggcc tgtgcgtgcc atccagagtc atctcagccc tgcctttctc      3180
tggagcattc tgaaaacaga tattctggcc caggaatcc agccatgacc ccacccctc      3240
tgccaaagta ctcttaggtg ccagtctggt aactgaactc cctctggagg caggcttgag      3300
ggaggattcc tcagggttcc cttgaaagct ttatttattt attttgttca tttatttatt      3360
ggagaggcag cattgcacag tgaaagaatt ctggatatct caggagcccc gaaattctag      3420
ctctgacttt gctgtttcca gtggtatgac cttggagaag tcacttatcc tcttggagcc      3480
tcagtttcct catctgcaga taatgactg acttgtctaa ttcataggga tgtgaggttc      3540
tgctgaggaa atgggtatga atgtgccttg aacacaaagc tctgtcaata agtgatacat      3600
gttttttatt ccaataaatt gtcaagacca ca                                   3632
```

<210> SEQ ID NO 2
<211> LENGTH: 3497
<212> TYPE: DNA
<213> ORGANISM: Mus musculus
<220> FEATURE:
<223> OTHER INFORMATION: mouse interleukin 10 receptor (IL-10R)

<400> SEQUENCE: 2

```
ccattgtgct ggaaagcagg acgcgccggc cggaggcgta aaggccggct ccagtggacg       60
atgccgctgt cgcccaggaa tgttgtcgcg tttgctccca ttcctcgtca cgatctccag      120
cctgagccta gaattcattg catacgggac agaactgcca agcccttcct atgtgtggtt      180
```

```
tgaagccaga ttttccagc acatcctcca ctggaaacct atcccaaacc agtctgagag    240
cacctactat gaagtggccc tcaaacagta cggaaactca acctggaatg acatccatat    300
ctgtagaaag gctcaggcat tgtcctgtga tctcacaacg ttcaccctgg atctgtatca    360
ccgaagctat ggctaccggg ccagagtccg ggcagtggac aacagtcagt actccaactg    420
gaccaccact gagactcgct tcacagtgga tgaagtgatt ctgacagtgg atagcgtgac    480
tctgaaagca atggacggca tcatctatgg gacaatccat cccccaggc ccacgataac    540 ccctgcaggg gatgagtacg aacaagtctt caaggatctc cgagtttaca agatttccat    600
ccggaagttc tcagaactaa agaatgcaac caagagagtg aaacaggaaa ccttcaccct    660
cacggtcccc atagggtga aaagttttg tgtcaaggtg ctgccccgct ggaatcccg    720 aattaacaag gcagagtggt cggaggagca gtgtttactt atcacgacgg agcagtattt    780
cactgtgacc aacctgagca tcttagtcat atctatgctg ctattctgtg gaatcctggt    840
ctgtctggtt ctccagtggt acatccggca cccggggaag ttgcctacag tcctggtctt    900
caagaagcct cacgacttct tcccagccaa ccctctctgc cagaaactc ccgatgccat    960 tcacatcgtg gacctggagg tttccaaa ggtgtcacta gagctgagag actcagtcct   1020
gcatggcagc accgacagtg gctttggcag tggtaaacca tcacttcaga ctgaagagtc   1080
ccaattcctc ctccctggct cccaccccca gatacagggg actctgggaa agaagagtc   1140 tccagggcta caggccacct gtgggacaa cacggacagt gggatctgcc tgcaggagcc   1200
cggcttacac tccagcatgg ggcccgcctg gaagcagcag cttggatata cccatcagga   1260
ccaggatgac agtgacgtta acctagtcca gaactctcca gggcagccta agtacacaca   1320
ggatgcatct gccttgggcc atgtctgtct cctagaacct aaagccctg aggagaaga   1380 ccaagtcatg gtgacattcc agggctacca gaaacagacc agatggaagg cagaggcagc   1440
aggcccagca gaatgcttgg acgaagagat tcccttgaca gatgcctttg atcctgaact   1500
tggggtacac ctgcaggatg atttggcttg gcctccacca gctctggccg caggttattt   1560
gaaacaggag tctcaaggga tggcttctgc tccaccaggg acaccaagta gacagtggaa   1620
tcaactgacc gaagagtggt cactcctggg tgtggttagc tgtgaagatc taagcataga   1680
aagttggagg tttgcccata aacttgaccc tctggactgt ggggcagccc ctggtggcct   1740
cctggatagc cttggctcta acctggtcac cctgccgttg atctccagcc tgcaggtaga   1800
agaatgacag cggctaagag ttatttgtat tccagccatg cctgctcccc tccctgtacc   1860
tgggaggctc aggagtcaaa gaaatatgtg gtccttttc tgcagaccta ctgtgaccag   1920
ctagccaggc tccacggggc aaggaaaggc atcttgata cacgagtgtc aggtacatga   1980
gaggttgtgg ctagtctgct gagtgagggt ctgtagatac cagcagagct gagcaggatt   2040
gacagagacc tcctcatgcc tcagggctgg ctcctacact ggaaggacct gtgtttgggt   2100
gtaacctcag ggctttctgg atgtggtaag actgtaggtc tgaagtcagc tgagcctgga   2160
tgtctgcgga ggtgttggag tggctagcct gctacaggat aaagggaagg ctcaagagat   2220
agaagggcag agcatgagcc aggtttaatt ttgtcctgta gagatggtcc ccagccagga   2280
tgggttactt gtggctggga gatcttgggg tatacaccac cctgaatgat cagccagtca   2340
attcagagct gtgtggcaaa agggactgag acccagaatt tctgttcctc ttgtgaggtg   2400
tctctgctac ccatctgcag acagacatct tcatctttt actatggctg tgtcccctga   2460
attaccagca gtgccaagc cattactccc tgctgctcac tgttgtgacg tcagaccaga   2520
ccagacgctg tctgtctgtg ttagtacact accctttagg tggcctttgg gcttgagcac   2580
```

-continued

```
tggcccaggc ttaggactta tgtctgcttt tgctgctaat ctctaactgc agacccagag    2640
aacagggtgc tgggctgaca cctccgtgtt cagctgtgtg acctccgacc agcagcttcc    2700
tcaggggact aaaataatga ctaggtcatt cagaagtccc tcatgctgaa tgttaaccaa    2760
ggtgcccctg gggtgatagt ttaggtcctg caacctctgg gttggaagga agtggactac    2820
ggaagccatc tgtcccsctg gggagcttcc acctcatgcc agtgtttcag agatcttgtg    2880
ggagcctagg gccttgtgcc aagggagctg ctagtccctg gggtctaggg ctggtccctg    2940
cctccctata ctgcgtttga acctgtcttc caaatggagg cagtttgcag cccctaagca    3000
aggatgctga gagaagcagc aaggctgctg atccctgagc ccagagtttc tctgaagctt    3060
tccaaataca gactgtgtga cggggtgagg ccagccatga actttggcat cctgccgaga    3120
aggtcatgac cctaatctgg tacgagagct ccttctggaa ctgggcaagc tctttgagac    3180
ccccctggaa cctttattta tttatttgct cacttattta ttgaggaagc agcgtggcac    3240
aggcgcaagg ctctgggtct ctcaggaggt ctagatttgc ctgccctgtt tctagctgtg    3300
tgaccttggg caagtcacgt ttcctcgtgg agcctcagtt ttcctgtctg tatgcaaagc    3360
ttggaaattg aaatgtacct gacgtgctcc atccctagga gtgctgagtc ccactgagaa    3420
agcgggcaca gacgcctcaa atggaaccac aagtggtgtg tgttttcatc ctaataaaaa    3480
gtcaggtgtt ttgtgga                                                  3497

<210> SEQ ID NO 3
<211> LENGTH: 867
<212> TYPE: DNA
<213> ORGANISM: Homo sapiens
<220> FEATURE:
<223> OTHER INFORMATION: human B7-1 (CD80)

<400> SEQUENCE: 3
atgggccaca cacggaggca gggaacatca ccatccaagt gtccatacct caatttcttt      60
cagctcttgg tgctggctgg tctttctcac ttctgttcag gtgttatcca cgtgaccaag    120
gaagtgaaag aagtggcaac gctgtcctgt ggtcacaatg tttctgttga agagctggca    180
caaactcgca tctactggca aaaggagaag aaaatggtgc tgactatgat gtctggggac    240
atgaatatat ggcccgagta caagaaccgg accatctttg atatcactaa taacctctcc    300
attgtgatcc tggctctgcg cccatctgac gagggcacat acgagtgtgt tgttctgaag    360
tatgaaaaag acgctttcaa gcgggaacac ctggctgaag tgacgttatc agtcaaagct    420
gacttcccta cacctagtat atctgacttt gaaattccaa cttctaatat tagaaggata    480
atttgctcaa cctctggagg ttttccagag cctcacctct cctggttgga aaatggagaa    540
gaattaaatg ccatcaacac aacagtttcc caagatcctg aaactgagct ctatgctgtt    600
agcagcaaac tggattttaa tatgacaacc aaccacagct tcatgtgtct catcaagtat    660
ggacatttaa gagtgaatca gaccttcaac tggaatacaa ccaagcaaga gcattttcct    720
gataacctgc tcccatcctg gccattacc ttaatctcag taaatggaat ttttgtgata    780
tgctgcctga cctactgctt tgccccaaga tgcagagaga aaggaggaa tgagagattg    840 agaagggaaa gtgtacgccc tgtataa                                        867

<210> SEQ ID NO 4
<211> LENGTH: 867
<212> TYPE: DNA
<213> ORGANISM: Macaca mulatta
<220> FEATURE:
```

<223> OTHER INFORMATION: rhesus monkey B7-1 (CD80)

<400> SEQUENCE: 4

| | | | | | |
|---|---|---|---|---|---|
| atgggccaca | cacggaggca | ggaaatatca | ccatccaagt | gtccatacct | caagttcttt | 60 |
| cagctcttgg | tgctggcttg | tctttctcat | ttctgttcag | gtgttatcca | cgtgaccaag | 120 |
| gaagtgaaag | aagtggcaac | gctgtcctgt | ggtcacaatg | tttctgttga | agagctggca | 180 |
| caaactcgca | tctactggca | aaaggagaag | aaaatggtgc | tgactatgat | gtctggggac | 240 |
| atgaatatat | ggcccgagta | caagaaccgg | accatctttg | atatcacaaa | taacctctcc | 300 |
| attgtgattc | tggctctgcg | cccatctgac | gagggcacat | acgagtgtgt | tgttctgaag | 360 |
| tatgaaaaag | atgctttcaa | gcgggaacac | ctggctgaag | tgatgttatc | cgtcaaagct | 420 |
| gacttcccta | cacctagtat | aactgactct | gaaattccac | cttctaacat | tagaaggata | 480 |
| atttgctcaa | actctggagg | ttttccagag | cctcacctct | cctggttgga | aaatggagaa | 540 |
| gaattaaatg | ccatcagcac | aacagtttcc | caagatcctg | aaactgagct | ctatactgtt | 600 |
| agcagcaaac | tggatttcaa | tatgacaacc | aatcacagtt | tcatgtgtct | catcaagtat | 660 |
| ggacatttaa | gagtgaatca | gaccttcaac | tggaacacac | caagcaaga | gcattttcct | 720 |
| gataacctgc | tcccatcctg | ggccattatc | ctaatctcag | taaatggaat | ttttgtgata | 780 |
| tgctgcctga | cctactgttt | tgccccaagg | tgcagagaga | aagaaggaa | tgagacattg | 840 |
| agaagggaaa | gtgtacgccc | tgtatga | | | | 867 |

<210> SEQ ID NO 5
<211> LENGTH: 900
<212> TYPE: DNA
<213> ORGANISM: Rabbit (genus and species unknown)
<220> FEATURE:
<223> OTHER INFORMATION: rabbit B7-1 (CD80)

<400> SEQUENCE: 5

| | | | | | |
|---|---|---|---|---|---|
| atgggccaca | cgctgaggcc | gggaactcca | ctgcccaggt | gtctacacct | caagctctgc | 60 |
| ctgctcttgg | cgctggcggg | tctccacttc | tcttcaggta | tcagccaggt | caccaagtcg | 120 |
| gtgaaagaaa | tggcagcact | gtcctgtgat | acaacatttt | ctatcgatga | actggcgaga | 180 |
| atgcgcatat | actggcagaa | ggaccaacag | atggtgctga | gcatcatctc | tgggcaagtg | 240 |
| gaagtgtggc | ctgagtacaa | gaaccgcacc | ttccccgaca | tcattaacaa | cctctccctt | 300 |
| atgatcctgg | cactgcgcct | gtcggacaag | ggcacctaca | cctgcgtggt | tcagaagaat | 360 |
| gagaacgggt | ctttcagacg | ggagcacctg | acctccgtga | cactgtccat | cagagctgac | 420 |
| ttccctgtcc | ctagcataac | tgacattgga | catcccgacc | ctaatgtgaa | aaggataaga | 480 |
| tgctccgcct | ctggaggttt | tccagagcct | cgcctcgcct | ggatggaaga | tggagaagaa | 540 |
| ctaaacgccg | tcaacacgac | ggttgaccag | gatttggaca | cggagctcta | cagcgtcagc | 600 |
| agtgaactga | atttcaatgt | gacaaataac | acacagcatcg | tgtgtctcat | caaatacggg | 660 |
| gagctgtcgg | tgtcacagat | cttcccttgg | agcaaaccca | agcaggagcc | tcccattgat | 720 |
| cagcttccat | tctgggtcat | tatcccagta | agtggtgctt | tggtgctcac | tgcggtagtt | 780 |
| ctctactgcc | tggcctgcag | acatgttgcg | aggtggaaaa | gaacaagaag | gaatgaagag | 840 |
| acagtgggaa | ctgaaaggct | gtccctatc | tacttaggct | ctgcgcaatc | ctcgggctga | 900 |

<210> SEQ ID NO 6
<211> LENGTH: 102
<212> TYPE: PRT
<213> ORGANISM: Artificial Sequence -continued

```
<220> FEATURE:
<223> OTHER INFORMATION: Description of Artificial Sequence:truncated
      hepatitis B surface antigen (HBsAg) (PreS2 plus S
      regions)

<400> SEQUENCE: 6

Met Gln Trp Asn Ser Thr Thr Phe His Gln Thr Leu Gln Asp Pro Arg
  1               5                  10                  15

Val Arg Gly Leu Tyr Phe Pro Ala Gly Gly Ser Ser Ser Gly Thr Val
             20                  25                  30

Asn Pro Val Leu Thr Thr Ala Ser Pro Leu Ser Ser Ile Phe Ser Arg
         35                  40                  45

Ile Gly Asp Pro Ala Leu Asn Met Glu Asn Ile Thr Ser Gly Phe Leu
     50                  55                  60

Gly Pro Leu Leu Val Leu Gln Ala Gly Phe Phe Leu Leu Thr Arg Ile
 65                  70                  75                  80

Leu Thr Ile Pro Gln Ser Leu Asp Ser Trp Trp Thr Ser Leu Asn Phe
                 85                  90                  95

Leu Gly Gly Thr Thr Val
            100
```